(12) United States Patent
Kohara et al.

(10) Patent No.: US 8,609,403 B2
(45) Date of Patent: Dec. 17, 2013

(54) POLYNUCLEOTIDE DERIVED FROM NOVEL HEPATITIS C VIRUS STRAIN AND USE THEREOF

(75) Inventors: Michinori Kohara, Tokyo (JP); Masaaki Arai, Osaka (JP); Chise Mukaidani, Higashi Hiroshima (JP)

(73) Assignees: Tokyo Metropolitan Institute of Medical Science, Tokyo (JP); Phoenixbio Co., Ltd., Hiroshima (JP)

( * ) Notice: Subject to any disclaimer, the term of this patent is extended or adjusted under 35 U.S.C. 154(b) by 21 days.

(21) Appl. No.: 13/388,382

(22) PCT Filed: Aug. 25, 2010

(86) PCT No.: PCT/JP2010/064417
§ 371 (c)(1),
(2), (4) Date: Feb. 1, 2012

(87) PCT Pub. No.: WO2011/024875
PCT Pub. Date: Mar. 3, 2011

(65) Prior Publication Data
US 2012/0204279 A1    Aug. 9, 2012

(30) Foreign Application Priority Data

Aug. 28, 2009  (JP) .................................. 2009-197923

(51) Int. Cl.
*C12N 15/00*  (2006.01)
*C12N 15/09*  (2006.01)
*C12N 15/11*  (2006.01)

(52) U.S. Cl.
USPC .................................. 435/320.1; 435/235.1

(58) Field of Classification Search
None
See application file for complete search history.

(56) References Cited

U.S. PATENT DOCUMENTS

| | | | |
|---|---|---|---|
| 5,667,992 A | 9/1997 | Casey et al. | |
| 6,630,343 B1 | 10/2003 | Bartenschlager | |
| 2003/0073080 A1* | 4/2003 | Rice et al. | 435/6 |
| 2004/0067486 A1* | 4/2004 | Paonessa et al. | 435/5 |
| 2004/0101827 A1* | 5/2004 | Kohara et al. | 435/5 |
| 2006/0174354 A1 | 8/2006 | Kohara et al. | |
| 2009/0035747 A1 | 2/2009 | Wakita et al. | |

FOREIGN PATENT DOCUMENTS

| | | |
|---|---|---|
| JP | 07-503614 | 4/1995 |
| JP | 2001-017187 | 1/2001 |
| JP | 2002-171978 | 6/2002 |
| WO | 02/28174 | 4/2002 |
| WO | 03/037081 | 5/2003 |
| WO | 2005/028652 | 3/2005 |

OTHER PUBLICATIONS

Donlin et al, Database DDBJ/EMBL/GenBank [online], Accession No. EF407439, <http://www.ncbi.nlm.nih.gov/nuccore/EF407439>, uploaded on Jan. 2, 2008, [retrieved on Nov. 14, 2012] Definition: Hepatitis C virus isolate 8003 polyprotein gene, complete cds.*
Krieger et al, Journal of Virology, 2001, 75:4614-4624.*
Reed et al, J Biol Chem, 1999, 274:28011-28018.*
Bhattacharyya et al, Database DDBJ-EMBL-GenBank [online], Accession No. AY344042, <http://www.ncbi.nlm.nih.gov/nucleotide/37790681?report=genbank&log$=nucltop&blast_rank=11&RID=ADDN7U6R01R>, uploaded on Apr. 23, 2004, [retrieved on Nov. 16, 2012] Definition: Hepatitis C virus isolate UT-S4 5'UTR.*
Tsuchihara et al, Database DDBJ/EMBL/GenBank [online], Accession No. AB001040, <http://www.ncbi.nlm.nih.gov/nucleotide/2653427?report=genbank&log$=nuclalign&blast_rank=2&RID=ABPKXUAW01R>, uploaded on Feb. 13, 1999, [retrieved on Nov. 16, 2012] Definition: Hepatitis C virus (subtype:1b) genomic RNA for polyprotein and 3'UTR, partial cds.*
International Preliminary Report on Patentability for PCT/JP2010/064417, mailed Mar. 22, 2012.
Donlin et al., "Pretreatment Sequence Diversity Differences in the Full-Length Hepatitis C Virus Open Reading Frame Correlate with Early Response to Therapy", Journal of Virology, Aug. 2007, pp. 8211-8224.
Database DDBJ/EMBL/GenBank [online], Accession No. EF407427, Donlin, M.J. et al., Definition: Hepatitis C virus isolate 6025 polyprotein gene, complete cds, uploaded on Jan. 2, 2008.
Database DDBJ/EMBL/GenBank [online], Accession No. EF407439, Donlin, M.J. et al., Definition: Hepatitis C virus isolate 8003 polyprotein gene, complete cds, uploaded on Jan. 2, 2008.
Database DDBJ/EMBL/GenBank [online], Accession No. EU781810, Kuntzen, T. et al., Definition: Hepatitis C virus subtype 1a isolate 03P, complete genome, uploaded on May 31, 2009.
Database DDBJ/EMBL/GenBank [online], Accession No. EU781759, Timm, J. et al., Definition: Hepatitis C virus subtype 1a isolate L8168, complete genome, uploaded on May 31, 2009.
Mori et al., "A New Type of Hepatitis C Virus in Patients in Thailand", Biochem. Biophis. Res. Commun., Feb. 28, 1992, pp. 334-342.
Blight et al., "Efficient Replication of Hepatitis C Virus Genome 1a RNAs in Cell Culture", Journal of Virology, Mar. 2003, pp. 3181-3190.
Lohmann et al., "Replication of Subgenonmic Hepatitis C Virus RNAs in a Hepatoma Cell Line", Science, Jul. 2, 1999, pp. 110-113.
Blight et al., "Efficient Initiation of HCV RNA Replication in Cell Culture", Science, Dec. 8, 2000, pp. 1972-1974.

(Continued)

*Primary Examiner* — Valarie Bertoglio
*Assistant Examiner* — Chi-Feng Hsu
(74) *Attorney, Agent, or Firm* — Greenblum & Bernstein, P.L.C.

(57) ABSTRACT

A polynucleotide encoding the amino acid shown in SEQ ID NO:2 or SEQ ID NO: 5, or encoding an amino acid sequence having not less than 98% identity thereto; preferably a polynucleotide comprising replacement of the amino acid corresponding to glutamic acid at position 1202 of SEQ ID NO:2 (position 177 of SEQ ID NO:5) with glycine, replacement of the amino acid corresponding to glutamic acid at position 1056 (position 31 of SEQ ID NO:5) with valine, and replacement of the amino acid corresponding to alanine at position 2199 (position 1174 of SEQ ID NO:5) with threonine.

10 Claims, 4 Drawing Sheets

(56) References Cited

OTHER PUBLICATIONS

Ikeda et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells", Journal of Virology, Mar. 2002, pp. 2997-3006.

Dusheiko et al., "Hepatitis C Virus Genotypes: An Investigation of Type-specific Differences in Geographic Origin and Disease", Hepatology, 1994, pp. 13-18.

Search report from International Application No. PCT/JP2010/064417, mail date is Nov. 30, 2010.

Extended European Search Report for patent family member EP Application No. 10811924 9, mailed Feb. 8, 2013.

Database UniProt [Online], "Hepatitis C virus subtype 1a," XP002690171, Database accession No. B3TKQ0_9HEPC, Sep. 2, 2008.

Database UniProt [Online], "Hepatitis C virus subtype 1a," XP002690172, Database accession No. B3TKQ1_9HEPC, Sep. 2, 2008.

* cited by examiner

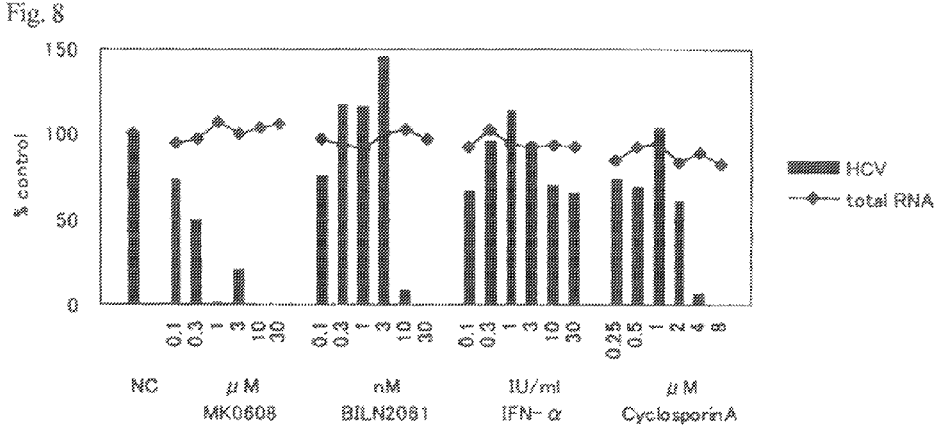
Fig. 8
Fig. 9
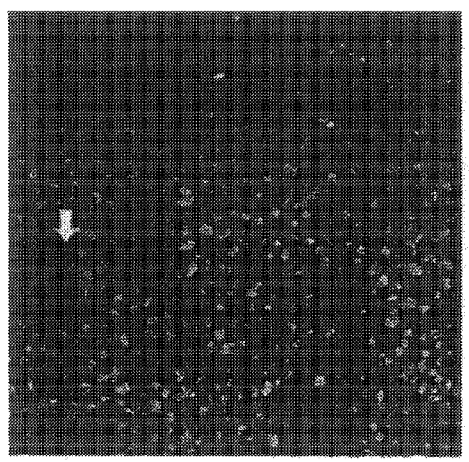
Huh7 infected with #11 cell culture supernatant
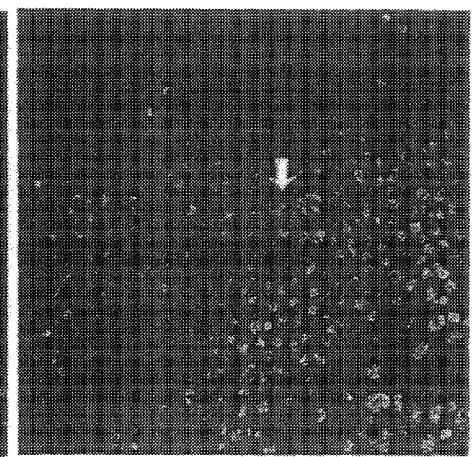
Huh7 infected with concentrated #11 cell culture supernatant

POLYNUCLEOTIDE DERIVED FROM NOVEL HEPATITIS C VIRUS STRAIN AND USE THEREOF

SEQUENCE LISTING

The instant application contains a Sequence Listing which has been submitted in ASCII format via EFS-Web and is hereby incorporated by reference in its entirety. Said ASCII copy, created on Apr. 17, 2012, is named P41504.txt and is 130,531 bytes in size.

TECHNICAL FIELD

The present invention relates to a polynucleotide derived from a novel strain of hepatitis C virus, a cell and a non-human mammal to which the polynucleotide has been introduced, and a replicon RNA prepared using the polynucleotide.

BACKGROUND ART

Hepatitis C virus (hereinafter referred to as HCV) is a virus which belongs to Flaviviridae and has a genome of a single-stranded (+)-strand sense RNA, and known to cause hepatitis C. Recent studies have revealed that HCV can be divided into many types based on the genotype or the serotype. According to a phylogenetic analysis by Simmonds et al. using nucleotide sequences of HCV strains, HCV can be divided into 6 types, that is, the genotype 1a, genotype 1b, genotype 2a, genotype 2b, genotype 3a and genotype 3b, each of which can be further divided into several subtypes (Non-patent Document 1).

At present, therapy for hepatitis C is carried out mainly with interferon-α or interferon-β, or by a combination therapy using interferon-α and a purine nucleoside-derivative ribavirin. However, even in cases where these therapies are carried out, a therapeutic effect can be observed in only about 60% of the overall patients, and, even in cases where the effect was observed in patients, recurrence occurs in more than half of the patients if the therapy was discontinued. The therapeutic effect of interferon is known to be correlated with the genotype of HCV, and it is said that the effect is low against the genotype 1b while the effect is high against the genotype 2a (Non-patent Document 2).

Therefore, in order to evaluate the effect of an agent, it is important to establish a system which allows infection with, and growth of, each type of the virus, and to thereby investigate the effect of the agent against each type of the virus.

Until recently, growing of HCV in a cell culture system and infection of cultured cells with HCV had been difficult, and the only animal which can be infected with HCV and can be used in experiments was chimpanzee, so that research on the replication mechanism of HCV and on its infection mechanism had been difficult. However, recently, HCV subgenomic RNA replicons were prepared as HCV-derived RNAs having self-replication capacity (Patent Document 1; Non-patent Document 3; Non-patent Document 4; Non-patent Document 5), and analysis of the replication mechanism of HCV using cultured cells became possible. These HCV subgenomic RNA replicons were prepared by replacing structural proteins existing in the downstream of HCV IRES in the 5'-untranslated region of the HCV genomic RNA of the clone called Con1, which belongs to the genotype 1b, with a neomycin resistance gene and EMCV-IRES linked to the downstream thereof. It has been demonstrated that introduction of the RNA replicons into Huh7 human liver cancer cells followed by culturing of the cells in the presence of neomycin allows self-replication of the replicons in the Huh7 cells. It is considered that the systems for evaluation of replication of HCV using this RNA replicon system can be a powerful tool for development of anti-HCV drugs However, since encoded viral proteins are different among HCVs having different genotypes, sufficient elucidation of the replication mechanism of HCV is difficult by only analyzing a subgenomic RNA replicon derived from HCV of the genotype 1b. Therefore, it is thought that preparation of HCV RNA replicons of many genotypes is necessary for research on the replication mechanism of HCV and anti-HCV drugs.

In Patent Document 2, identification of the virus and the genomic sequence are disclosed for the JFH-1 strain, which belongs to the 2a type. Further, in Patent Document 3, the JFH 2.1 strain and 2.2 strain, which similarly belong to the 2a type, and preparation of replicon RNAs using them are disclosed. On the other hand, in terms of the 1a type, there is a report on the H77 strain (Non-patent Document 6), but a recombinant virus obtained from this strain does not have a sufficient replication efficiency. Further, although a replicon was successfully prepared by introduction of 5 types of mutations which were predicted based on the 1b type, this replicon could be replicated only in a special cell.

PRIOR ART DOCUMENTS

Patent Documents

[Patent Document 1] JP 2001-17187 A
[Patent Document 2] JP 2002-171978 A
[Patent Document 3] WO 2005/028652

Non-Patent Documents

[Non-patent Document 1] Hepatorigy (1994) 10, p 1321-1324
[Non-patent Document 2] Biochem. Biophis. Res. Commun., (1992) 183, 334-342
[Non-patent Document 3] Science, (1999) 285, 110-113
[Non-patent Document 4] Science, (2000) 290, 1972-1974
[Non-patent Document 5] J. Virol., (2002) 76 2997-3006
[Non-patent Document 6] J. Virol. (2003) 77 3181-3190

DISCLOSURE OF THE INVENTION

The present invention aims to provide a polynucleotide derived from a novel strain of HCV, and to use this for providing an HCV replicon RNA having high replication efficiency and HCV replicon cells with which continuous mass production of an HCV protein is possible.

The inventors of the present invention intensively studied to solve the above problems, and, as a result, a novel RMT strain, which is grouped into the 1a type of HCV, was isolated from the serum of a hepatitis C patient; the nucleotide sequence of the strain was determined; and it was discovered that the virus has high infection efficiency. The inventors of the present invention then succeeded in preparing replicon RNAs having high replication efficiency using this virus, thereby completed the present invention. That is, the present invention provides the followings.

(1) A polynucleotide which encodes the amino acid sequence shown in SEQ ID NO:2 or an amino acid sequence having not less than 98% identity thereto, wherein said polynucleotide can express nonstructural proteins and structural proteins of hepatitis C virus (HCV).

(2) The polynucleotide according to (1), wherein said amino acid sequence shown in SEQ ID NO:2 or an amino acid sequence having not less than 98% identity thereto comprises replacement of the amino acid corresponding to glutamic acid at position 1202 of SEQ ID NO:2 with glycine.

(3) The polynucleotide according to (1), wherein said amino acid sequence shown in SEQ ID NO:2 or an amino acid sequence having not less than 98% identity thereto comprises replacement of the amino acid corresponding to glutamic acid at position 1202 of SEQ ID NO:2 with glycine, replacement of the amino acid corresponding to glutamic acid at position 1056 with valine, and replacement of the amino acid corresponding to alanine at position 2199 with threonine.

(4) The polynucleotide according to (2) or (3), wherein said amino acid sequence shown in SEQ ID NO:2 or an amino acid sequence having not less than 98% identity thereto further comprises replacement of the amino acid corresponding to serine at position 2321 of SEQ ID NO:2 with proline and/or replacement of the amino acid corresponding to leucine at position 2889 with phenylalanine (5) The polynucleotide according to any one of (1) to (4), wherein said polynucleotide comprises the nucleotide sequence shown in SEQ ID NO:1 or a nucleotide sequence having not less than 95% homology thereto, and wherein, in cases where the polynucleotide is RNA, the nucleotide "t" in SEQ ID NO:1 is read as "u".

(6) A hepatitis C virus particle comprising the polynucleotide according to any one of (1) to (5).

(7) A non-human mammal to which the polynucleotide according to any one of (1) to (5) has been introduced and which produces a recombinant HCV.

(8) The non-human mammal according to (7), wherein said non-human mammal is a human hepatocyte chimeric mouse.

(9) A cell to which the polynucleotide according to any one of (1) to (5) has been introduced and which produces a recombinant HCV.

(10) A method of screening or evaluating a drug candidate substance which inhibits replication or protein translation of HCV, said method comprising administering or adding said drug candidate substance to the non-human mammal according to (7) or (8) or to the cell according to (9) and evaluating replication capacity of HCV or capacity of translation of HCV protein.

(11) A polynucleotide which encodes the amino acid sequence shown in SEQ ID NO:5 or an amino acid sequence having not less than 98% identity thereto, and wherein said polynucleotide can express nonstructural proteins of HCV.

(12) The polynucleotide according to (11), wherein said amino acid sequence shown in SEQ ID NO: 5 or an amino acid sequence having not less than 98% identity thereto comprises replacement of the amino acid corresponding to glutamic acid at position 177 of SEQ ID NO:5 with valine.

(13) The polynucleotide according to (11), wherein said amino acid sequence shown in SEQ ID NO: 5 or an amino acid sequence having not less than 98% identity thereto comprises replacement of the amino acid corresponding to glutamic acid at position 177 of SEQ ID NO:5 with valine, replacement of the amino acid corresponding to glutamic acid at position 31 with glycine, and replacement of the amino acid corresponding to alanine at position 1174 with threonine.

(14) The polynucleotide according to (12) or (13), wherein said amino acid sequence shown in SEQ ID NO:5 or an amino acid sequence having not less than 98% identity thereto further comprises replacement of the amino acid corresponding to serine at position 1296 of SEQ ID NO:5 with proline and/or replacement of the amino acid corresponding to leucine at position 1864 with phenylalanine.

(15) The polynucleotide according to any one of (11) to (14), further comprising an IRES sequence.

(16) The polynucleotide according to any one of (11) to (15), further comprising a selection marker gene or a reporter gene.

(17) The polynucleotide according to any one of (11) to (16), wherein said polynucleotide comprises the nucleotide sequence shown in SEQ ID NO:3 or a polynucleotide which is able to hybridize with the complementary sequence of SEQ ID NO:3 under stringent conditions, and wherein, in cases where the polynucleotide is RNA, the nucleotide "t" in SEQ ID NO:3 is read as "u".

(18) The polynucleotide according to (17), wherein said polynucleotide is a replicon RNA.

(19) A replicon-replicating cell prepared by introducing the replicon RNA according to (18).

(20) The replicon-replicating cell according to (19), wherein the cell is a human liver-derived cell, human uterine cervix-derived cell or human fetal kidney-derived cell.

(21) The replicon-replicating cell according to (19) or (20), wherein the cell is a Huh7 cell, HepG2 cell, IMY-N9 cell, HeLa cell or 293 cell.

(22) A method of screening or evaluating a drug candidate substance which inhibits replication or protein translation of HCV, said method comprising adding a drug candidate substance to the replicon-replicating cell according to any one of (19) to (21) and evaluating replication capacity or protein translation of said replicon RNA.

By using a polynucleotide of the novel HCV strain of the present invention, HCV-1a-type-infected model animals and cells can be efficiently obtained.

Further, by using a polynucleotide of the novel HCV strain of the present invention, replicon RNAs and replicon-replicating cells having high replication efficiency can be obtained at a high probability. These replicon-replicating cells can be used as culture systems for continuous production of HCV-derived RNAs and HCV proteins. Further, the replicon-replicating cells can also be used as test systems for screening of various substances that influence replication of HCV or translation of HCV proteins.

BRIEF DESCRIPTION OF THE DRAWINGS

FIG. 1 is a diagram showing results of an experiment on infection of human hepatocyte chimeric mice with the serum derived from a patient suffering from 1a-type hepatitis C.

FIG. 2 is a diagram showing the positions of primers for analysis of the sequence of the RMT strain, which primers were designed based on the sequence of the H77 strain.

FIG. 3 is a diagram showing the structure of an RMT recombinant virus expression vector.

FIG. 4 is a diagram showing results of comparison of the efficiency of infection to human hepatocyte chimeric mice between the RMT strain and the JFH1 strain.

FIG. 5 is a diagram showing the structure of an expression vector for a replicon RNA derived from the RMT strain.

FIG. 6 is a diagram (photographs) showing the colony formation capacities of replicon RNAs having various mutations, in the presence of an agent.

FIG. 7 is a diagram showing the replication efficiencies of RMT recombinant viruses in Huh7 cells.

FIG. 8 is a diagram showing results of investigation of the effects of antiviral agents in Huh7 cells, using an RMT recombinant virus (to which a triple mutation was introduced).

FIG. 9 is a diagram (micrographs) showing results of fluorescent antibody staining of the HCV-core protein in Huh7 cells infected with culture supernatant (A) or concentrated culture supernatant (B) of #11 cells. The arrowheads indicate stained positions.

DESCRIPTION OF THE EMBODIMENTS

Figure 1:
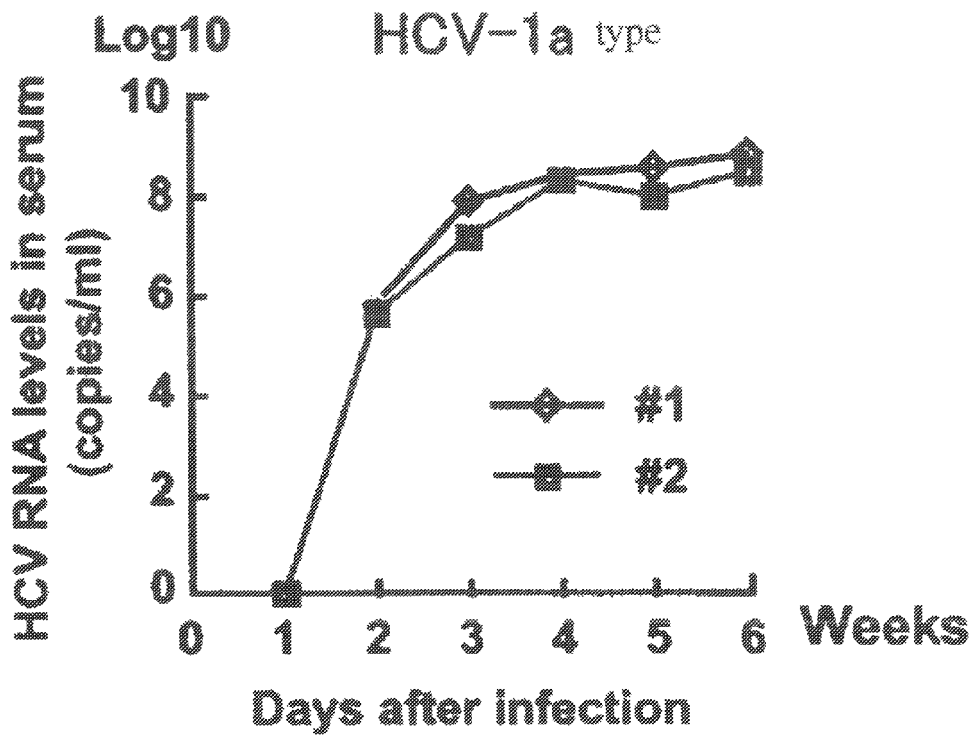

The present invention will be described below in detail.

In the present specification, a "polynucleotide" means either RNA or DNA. That is, a "polynucleotide which can express a viral protein" may be either RNA which can be translated into the protein, or DNA which can be transcribed into RNA, followed by being translated into the protein.

Further, the polynucleotide may be either single-stranded or double-stranded, and may be either naturally occurred or artificially synthesized. Further, the polynucleotide may be partially modified and may be a derivative. It should be noted that each nucleotide sequence in SEQUENCE LISTING is represented as DNA for convenience, but, in cases where the polynucleotide is RNA, the nucleotide symbol "t" is read as "u".

The polynucleotide of the first embodiment of the present invention is a polynucleotide encoding structural proteins and nonstructural proteins of HCV.

Examples of such a polynucleotide include the one encoding the amino acid sequence shown in SEQ ID NO:2.

The amino acid sequence shown in SEQ ID NO:2 is composed of a region comprising structural proteins (Core, E1 and E2) and a region comprising nonstructural proteins (NS2, NS3, NS4A, NS4B, NS5A and NS5B).

Such structural proteins (Core, E1 and E2) and nonstructural proteins (NS2, NS3, NS4A, NS4B, NS5A and NS5B) of HCV are translated as a continuous polyprotein from the translated region and then released by limited hydrolysis by protease. Among these structural proteins and nonstructural proteins (that is, viral proteins of HCV), Core is a core protein, E1 and E2 are envelope proteins, and the nonstructural proteins are proteins involved in replication of the virus itself. Further, it is known that NS2 has a metalloprotease activity and NS3 has a serine protease activity (one third from N-terminus of the whole protein) and a helicase activity (two thirds from C-terminus of the whole protein). Further, it has been reported that NS4A is a cofactor for the protease activity of NS3, and that NS5B has an RNA-dependent RNA polymerase activity.

In the amino acid sequence shown in SEQ ID NO:2, amino acid positions 1 to 191 correspond to the Core protein; amino acid positions 192 to 383 correspond to the E1 protein; amino acid positions 384 to 809 correspond to the E2 protein; amino acid positions 810 to 1026 correspond to the NS2 protein; amino acid positions 1027 to 1657 correspond to the NS3 protein; amino acid positions 1658 to 1711 correspond to the NS4A protein; amino acid positions 1712 to 1972 correspond to the NS4B protein; amino acid positions 1973 to 2420 correspond to the NS5A protein; and amino acid positions 2421 to 3011 correspond to the NS5B protein.

The polynucleotide of the present invention is derived from the RMT strain, and may be derived either from the RMT strain itself or from a derivative of the RMT strain.

That is, in the sequence of the polynucleotide of the first embodiment of the present invention, a substitution(s), deletion(s), addition(s), insertion(s) and/or the like may exist(s) as long as the polynucleotide encodes the respective viral proteins described above which are functional. More particularly, the polynucleotide of the first embodiment of the present invention may be a polynucleotide encoding an amino acid sequence having not less than 98% identity, preferably not less than 99% identity, to the entire amino acid sequence shown in SEQ ID NO:2

Further, the polynucleotide of the first embodiment of the present invention may be a polynucleotide encoding an amino acid sequence which is the same as the amino acid sequence shown in SEQ ID NO:2 except that one or more amino acids, particularly 1 to 50, preferably 1 to 30, more preferably 1 to 10, still more preferably 1 to 5 amino acids are substituted, deleted, added and/or inserted, as long as the polynucleotide encodes the respective viral proteins described above which are functional.

In order to maintain high replication capacity in cultured cells, preferably, the amino acid corresponding to glutamic acid at position 1202 of SEQ ID NO:2 is replaced with glycine, and, more preferably, the amino acid corresponding to glutamic acid at position 1202 is replaced with glycine; the amino acid corresponding to glutamic acid at position 1056 is replaced with valine; and the amino acid corresponding to alanine at position 2199 is replaced with threonine. Further, in addition to the above replacements, the polynucleotide may have replacement of the amino acid corresponding to serine at position 2321 of SEQ ID NO:2 with proline and/or replacement of the amino acid corresponding to leucine at position 2889 with phenylalanine.

The "amino acid corresponding to glutamic acid at position 1202 of SEQ ID NO:2" herein means the amino acid existing at the position of glutamic acid at position 1202 of SEQ ID NO:2 based on comparison of sequences, and, for example, in cases where position 1202 becomes position 1201 due to deletion of an amino acid in the upstream of position 1202, the amino acid at position 1201 is referred to as the "amino acid corresponding to glutamic acid at position 1202 of SEQ ID NO:2".

The polynucleotide of the first embodiment of the present invention encodes the structural proteins and the nonstructural proteins of HCV, and, preferably, the polynucleotide comprises the 5'-untranslated region and the 3'-untranslated region in the upstream and the downstream, respectively, of the proteins, and can produce an HCV having the capacities of infection and self-replication. Examples of such a polynucleotide include viral genomic RNAs, and DNAs that express the RNAs.

Particular examples of such a polynucleotide include the polynucleotide having the nucleotide sequence shown in SEQ ID NO:1.

In the nucleotide sequence shown in SEQ ID NO:1, nucleotide positions 1 to 341 correspond to the "5'-untranslated region (5'-UTR)"; nucleotide positions 342 to 914 correspond to the Core protein-coding region, nucleotide positions 915 to 1490 correspond to the E1 protein-coding region; nucleotide positions 1491 to 2768 correspond to the E2 protein-coding region; nucleotide positions 2769 to 3419 correspond to the NS2 protein-coding region; nucleotide positions 3420 to 5312 correspond to the NS3 protein-coding region; nucleotide positions 5313 to 5474 correspond to the NS4A protein-coding region; nucleotide positions 5475 to 6257 correspond to the NS4B-coding region; nucleotide positions 6258 to 7601 correspond to the NS5A protein-coding region; nucleotide positions 7602 to 9374 correspond to the NS5B protein-coding region; and nucleotide positions 9375 to 9598 correspond to the "3'-untranslated region (3'-UTR)".

The polynucleotide of the first embodiment of the present invention is not restricted to the polynucleotide having the nucleotide sequence of SEQ ID NO:1, and a polynucleotide which is able to hybridize with the complementary strand of SEQ ID NO:1 under stringent conditions is also included in the polynucleotide of the present invention as long as the polynucleotide encodes the respective desired proteins described above. The "stringent conditions" herein means conditions under which the so-called specific hybrid is formed while a non-specific hybrid is not formed, and examples of the stringent conditions include: conditions under which DNAs having a high homology, for example, a not less than 95% homology, to each other hybridize with each other, while DNAs having a lower homology to each other do not hybridize with each other; and conditions under which one time, more preferably 2 or 3 times, of washing is carried out at a salt concentration and a temperature corresponding to those in normal washing conditions for Southern hybridization, such as at 60° C. in 0.1×SSC, 0.1% SDS, more preferably at 68° C. in 0.1×SSC, 0.1% SDS.

By introducing the polynucleotide of the first embodiment of the present invention into a non-human mammal, a 1a-type-HCV-infected model animal can be prepared. Examples of the non-human mammal include mouse, rat, rabbit, dog and chimpanzee, and the non-human mammal is preferably a human hepatocyte chimeric mouse.

A uPA/SCID mouse was prepared by crossing a mouse prepared by gene transfer of the urokinase plasminogen activator (uPA) gene linked to an enhancer and a promoter of albumin (uPA-Tg mouse) with a SCID mouse, and human hepatocytes were transplanted to the resulting mouse, to prepare a human hepatocyte chimeric mouse wherein not less than 70% of the mouse liver was replaced with human hepatocytes. By inoculating HCV to the thus prepared human hepatocyte chimeric mouse, an HCV-persistently-infected chimeric mouse can be prepared.

Such a 1a-type-HCV-infected model animal can be used for research on the control mechanisms of infection and replication of 1a-type HCV, and for evaluation and screening of drug candidate substances.

Further, by introducing the polynucleotide of the first embodiment of the present invention into cultured cells, 1a-type-HCV-producing cells can be obtained. The type of the cells is not restricted, and the cells are preferably mammalian-derived cells, more preferably human liver-derived cells, human uterine cervix-derived cells or human fetal kidney-derived cells. Particular examples of the cells include Huh7 cells, HepG2 cells, IMY-N9 cells, HeLa cells and 293 cells. Such 1a-type-HCV-producing cells can be used for research on the control mechanisms of infection and replication of 1a-type HCV, and for evaluation and screening of drug candidate substances.

The polynucleotide of the second embodiment of the present invention is a polynucleotide encoding nonstructural proteins of HCV.

Examples of such a polynucleotide include the one encoding the amino acid sequence shown in SEQ ID NO:5.

The amino acid sequence shown in SEQ ID NO:5 comprises nonstructural proteins (NS2, NS3, NS4A, NS4B, NS5A and NS5B).

In the amino acid sequence shown in SEQ ID NO:5, amino acid positions 2 to 632 correspond to the NS3 protein; amino acid positions 633 to 686 correspond to the NS4A protein; amino acid positions 687 to 947 correspond to the NS4B protein; amino acid positions 948 to 1395 correspond to the NS5A protein; and amino acid positions 1396 to 1986 correspond to the NS5B protein In the sequence of the polynucleotide of the second embodiment of the present invention, a substitution(s), deletion(s), addition(s), insertion(s) and/or the like may exist as long as the polynucleotide encodes the respective viral proteins described above which are functional. More particularly, the polynucleotide of the second embodiment of the present invention may be a polynucleotide encoding an amino acid sequence having not less than 98% identity, preferably not less than 99% identity, to the entire amino acid sequence shown in SEQ ID NO:5.

In the sequence the polynucleotide of the second embodiment of the present invention, a substitution(s), deletion(s), addition(s), insertion(s) and/or the like may exist(s) as long as the polynucleotide encodes the respective viral proteins described above which are functional. More particularly, the polynucleotide of the second embodiment of the present invention may be a polynucleotide encoding an amino acid sequence which is the same as the amino acid sequence shown in SEQ ID NO:5 except that one or more amino acids, particularly 1 to 30, preferably 1 to 10, more preferably 1 to 5 amino acids are substituted, deleted, added and/or inserted.

The polynucleotide of the second embodiment of the present invention is preferably an RNA having the 5'-untranslated region and the 3'-untranslated region in the upstream and downstream, respectively, of the region encoding the nonstructural proteins, and having the capacity of self-replication in a host cell; or a DNA which can produce the RNA. In the present specification, the RNA having the capacity of self-replication in a host cell is referred to as a "replicon RNA" or "RNA replicon".

One embodiment of the HCV replicon RNA of the present invention is a replicon RNA composed of a nucleotide sequence comprising at least the 5'-untranslated region; a sequence encoding the NS3 protein, NS4A protein, NS4B protein, NS5A protein and NS5B protein; and the 3'-untranslated region, in the genomic RNA of the RMT strain.

The HCV replicon RNA, or the DNA expressing it, of the present invention preferably comprises a mutation(s) which enable(s) its efficient replication in a host cell.

Examples of such a mutation(s) include replacement of the amino acid corresponding to glutamic acid at position 177 of SEQ ID NO:5 (position 1202 of SEQ ID NO:2) with glycine; and the triple mutation by replacement of the amino acid corresponding to glutamic acid at position 177 of SEQ ID NO:5 (position 1202 of SEQ ID NO:2) with glycine, replacement of the amino acid corresponding to glutamic acid at position 31 of SEQ ID NO:5 (position 1056 of SEQ ID NO:2) with valine, and replacement of the amino acid corresponding to alanine at position 1174 of SEQ ID NO:5 (position 2199 of SEQ ID NO:2) with threonine is more preferred. Further, in addition to the above replacements, replacement of the amino acid corresponding to serine at position 1296 of SEQ ID NO:5 with proline and/or replacement of the amino acid corresponding to leucine at position 1864 with phenylalanine may be contained.

The HCV replicon RNA of the present invention may further comprise an IRES sequence, and may still further comprise a selection marker gene or reporter gene.

The selection marker gene or reporter gene may be linked to the upstream of the IRES sequence, or to the upstream or the downstream of the "sequence encoding the NS3 protein, NS4A protein, NS4B protein, NS5A protein and NS5B protein"; or may be inserted into the "sequence encoding the NS3 protein, NS4A protein, NS4B protein, NS5A protein and NS5B protein".

A preferred embodiment of the HCV replicon RNA of the present invention is a replicon RNA composed of a polynucleotide comprising the 5'-untranslated region; at least one selection marker gene or reporter gene; at least one IRES sequence; a nucleotide sequence in the genomic RNA of HCV, encoding the NS3 protein, NS4A protein, NS4B protein, NS5A protein and NS5B protein; and the 3'-untranslated region.

The replicon RNA of the present invention more preferably has the 5'-untranslated region of the genomic RNA of HCV; has a selection marker gene or reporter gene, an IRES sequence, and the "sequence encoding the NS3 protein, NS4A protein, NS4B protein, NS5A protein and NS5B protein", in this order, in the downstream of the 5'-untranslated region; and has the 3'-untranslated region of the genomic RNA of HCV, in the 3'-end.

A more preferred embodiment of the HCV replicon RNA of the present invention is a replicon RNA composed of RNA having the nucleotide sequence shown in SEQ ID NO:3. A nucleic acid which is able to hybridize with the complementary strand of SEQ ID NO:3 under stringent conditions is also included therein. The meaning of the "stringent conditions" is as mentioned above.

In the nucleotide sequence shown in SEQ ID NO:3, nucleotide positions 1 to 341 correspond to the "5'-UTR"; nucleotide positions 342 to 1181 correspond to a neomycin resistance gene; nucleotide positions 1185 to 1764 correspond to EMCV IRES; nucleotide positions 1765 to 7722 correspond to the "nonstructural protein (NS3, NS4A, NS4B, NS5A and NS5B proteins)-coding region"; and nucleotide positions 7723 to 7946 correspond to the "3'-UTR".

Although replicon RNAs were explained above, DNAs that can express the replicon RNAs are also, of course, included in the polynucleotide of the present invention.

In the present invention, "having the capacity of self-replication" means that, in cases where a replicon RNA is introduced to a cell, the replicon RNA can replicate the replicon RNA itself in the cell. The capacity of autonomous replication can be confirmed by, for example, transfection of the replicon RNA into a Huh7 cell and culturing of the Huh7 cell, followed by subjecting RNA extracted from cells in the obtained culture to Northern blot hybridization or RT-PCR using a probe or primer with which the introduced replicon RNA can be specifically detected, to detect the presence of the replicon RNA. The particular operation to confirm the capacity of autonomous replication can be carried out according to descriptions in Examples of the present description, about measurement of the colony forming capacity, confirmation of expression of an HCV protein, detection of a replicon RNA, and the like.

The replicon RNA of the present invention may comprise, in addition to the above-described sequences, an RNA having an arbitrary foreign gene which is to be expressed in the cell to which the replicon RNA is to be introduced. The foreign gene may be linked to the downstream of the 5'-untranslated region; linked to the upstream or the downstream of the selection marker gene or reporter gene; linked to the upstream or the downstream of the "sequence encoding the NS3 protein, NS4A protein, NS4B protein, NS5A protein and NS5B protein"; or inserted into the "sequence encoding the NS3 protein, NS4A protein, NS4B protein, NS5A protein and NS5B protein". The replicon RNA comprising a foreign gene can express the protein encoded by the foreign gene when the replicon RNA is translated in the cell to which the replicon RNA is introduced. Thus, the replicon RNA comprising a foreign gene can be suitably used also in cases where a specific gene product is produced in the cell, such as the cases of gene therapy.

In the present invention, a "selection marker gene" means a gene which can add selectivity to cells such that only cells wherein the gene is expressed can be selected. Common examples of the selection marker gene include antibiotic resistance genes. Examples of selection marker genes suitable in the present invention include the neomycin resistance gene, thymidine kinase gene, kanamycin resistance gene, pyrithiamin resistance gene, adenyltransferase gene, zeocin resistance gene and puromycin resistance gene, among which the neomycin resistance gene and thymidine kinase gene are preferred, and the neomycin resistance gene is more preferred.

In the present invention, a "reporter gene" means a marker gene encoding a gene product which can be used as an index of expression of the gene. Common examples of the reporter gene include structural genes of enzymes that catalyze a luminous reaction or a color reaction. Examples of reporter gene suitable in the present invention include the chloramphenicol acetyltransferase gene, β-galactosidase gene, luciferase gene, green fluorescent protein gene, aequorin gene derived from jerry fish and secreted placental alkaline phosphatase (SEAP) gene.

Either only one or both of the above selection marker gene and reporter gene may be contained in the replicon RNA.

The "IRES sequence" in the present invention means an internal ribosome binding site which can allow a ribosome to bind to the inside of RNA to initiate translation. Suitable examples of the IRES sequence in the present invention include, but are not limited to, EMCV IRES (internal ribosome binding site of encephalomyocarditis virus), FMDV IRES and HCV IRES, among which EMCV IRES and HCV IRES are more preferred, and EMCV IRES is most preferred.

The replicon RNA of the present invention may further comprise a ribozyme. The ribozyme is inserted such that it links the selection marker gene, reporter gene or foreign gene in the 5'-side replicon RNA to the IRES sequence and the "sequence encoding the NS3 protein, NS4A protein, NS4B protein, NS5A protein and NS5B protein" in the 3'-side, to allow their cleavage and separation by the self-cleavage activity of the ribozyme.

In the replicon RNA of the present invention, the above-mentioned selection marker gene; reporter gene; sequence encoding virus proteins in the genomic RNA of hepatitis C virus derived from a patient suffering from fulminant hepatitis; foreign gene, and the like are linked together such that translation occurs in the replicon RNA in the correct reading frame. Among these sequences, sequences encoding proteins may be linked to each other via protease cleavage sites or the like such that these sequences are expressed as a fusion protein with the polyprotein translated from the "sequence encoding the NS3 protein, NS4A protein, NS4B protein, NS5A protein and NS5B protein" of hepatitis C virus and then separated into the respective proteins by protease.

The HCV replicon RNA of the present invention can be prepared using arbitrary genetic engineering techniques which are known to those skilled in the art. For example, the HCV replicon RNA can be prepared by the following method.

First, the NS3 protein, NS4A protein, NS4B protein, NS5A protein and NS5B protein, and DNA corresponding to the RNA in the 3'-untranslated region are inserted into a cloning vector by a conventional method to prepare a DNA clone. On the other hand, the 5'-untranslated region is inserted in the downstream of an RNA promoter, to prepare a DNA clone. The "DNA corresponding to the RNA" means DNA having the nucleotide sequence wherein u (uracil) in the nucleotide sequence of the RNA is replaced with t (thymine). The RNA promoter is preferably one contained in a plasmid clone.

Preferred examples of the RNA promoter include, but are not limited to, a T7 RNA promoter, SP6 RNA promoter and SP3 RNA promoter, among which a T7 RNA promoter is especially preferred.

Subsequently, for example, in the prepared DNA clone of the 5'-untranslated region, a selection marker gene or a reporter gene is inserted into the downstream of the 5'-untranslated region, and an IRES sequence is inserted into the further downstream. Thereafter, by linking the both clones to each other, a DNA for expressing the HCV replicon RNA of the present invention can be obtained.

Subsequently, RNA is synthesized by RNA polymerase using the thus prepared DNA clone as a template. The RNA synthesis can be initiated from the 5'-untranslated region and the IRES sequence by a conventional method. In cases where the template DNA is a plasmid clone, the above-described DNA region linked to the downstream of the RNA promoter may be cleaved out using a restriction enzyme, to synthesize RNA using the DNA fragment as a template. Thus, the replicon RNA of the present invention can be obtained.

By introducing the thus prepared replicon RNA into a cell wherein the replicon RNA is to be replicated, a cell wherein the replicon RNA is continuously replicating can be obtained. In the present specification, the cell wherein the replicon RNA is continuously replicating is referred to as a "replicon-replicating cell".

As the cell to which the replicon RNA is to be introduced, an arbitrary cell can be used as long as the cell can be subcultured, and the cell is preferably a eukaryotic cell, more preferably a human liver-derived cell, human uterine cervix-derived cell or human fetal kidney-derived cell, still more preferably a Huh7 cell, HepG2 cell, IMY-N9 cell, HeLa cell or 293 cell. These cells may be those obtained from a commercial source; may be obtained from a cell depository; or may be those established from an arbitrary cell (e.g., from a cancer cell or stem cell).

The introduction of the replicon RNA into cells may be carried out using an arbitrary technique known to those skilled in the art. Examples of the introduction method include electroporation, the particle gun method, lipofection, the calcium phosphate method, microinjection and the DEAE sepharose method, among which electroporation is especially preferred.

The amount of the replicon RNA to be used for the introduction into cells may be determined depending on the type of the introduction method, and is preferably 1 picogram to 100 micrograms, more preferably 10 picograms to 10 micrograms.

In cases where a replicon RNA comprising a selection marker gene or a reporter gene is used for the introduction into cells, cells to which the replicon RNA was introduced wherein the replicon RNA is continuously replicating can be selected using expression of the selection marker gene or the reporter gene. More particularly, for example, cells subjected to treatment for introduction of such a replicon RNA into the cells may be cultured in a medium wherein selection is possible based on expression of the selection marker gene or the reporter gene.

For example, in cases where a neomycin resistance gene is contained as a selection marker gene in the replicon RNA, cells subjected to treatment for introduction of the replicon RNA into the cells are plated on a culture dish, and the cells are cultured for 16 to 24 hours, followed by addition of G418 (neomycin) to the culture dish at a concentration of 0.05 milligram/milliliter to 3.0 milligrams/milliliter. Thereafter, with replacement of the culture medium twice per week, the culture is continued, and viable cells are stained with crystal violet after preferably 10 days to 40 days, more preferably 14 days to 28 days of culture after the plating. By this, cells to which the replicon RNA was introduced wherein the replicon RNA is replicating continuously can be selected as colonies.

From the formed colonies, cells can be cloned by a conventional method. The thus obtained cell clone wherein the replicon RNA of interest is continuously replicating is referred to as a "replicon-replicating cell clone" in the present specification.

Whether the replicon RNA of interest is actually continuously replicating in the established cell clone is preferably confirmed by detection of the replicon RNA replicated from the introduced replicon RNA in the cell clone, confirmation of incorporation of the selection marker gene or the reporter gene in the introduced replicon RNA into the host genomic DNA, and confirmation of expression of an HCV protein.

The replicon RNA replicated from the introduced replicon RNA in the cell clone (which is referred to as a "replicated replicon RNA" in the present specification, for convenience) may be detected by an arbitrary RNA detection method known to those skilled in the art. For example, the replicated replicon RNA can be detected by subjecting total RNA extracted from the cell clone to Northern hybridization or RT-PCR using a DNA fragment specific to the introduced replicon RNA, as a probe or a primer.

Incorporation of the selection marker gene or the reporter gene in the introduced replicon RNA into the host genomic DNA can be confirmed by, for example, performing PCR to amplify at least a part of the selection marker gene or the reporter gene in the host genomic DNA extracted from the cell clone, thereby confirming the presence/absence of the amplified product.

Expression of an HCV protein can be confirmed by, for example, allowing an antibody against the HCV protein, which should be expressed from the introduced replicon RNA, to react with protein extracted from the cell clone. This method can be carried out by an arbitrary protein detection method known to those skilled in the art, and, more particularly, for example, it can be carried out by blotting a protein sample extracted from the cell clone onto a nitrocellulose membrane and reacting an anti-HCV-protein antibody (e.g., an anti-NS3 specific antibody, or an antiserum collected from a patient suffering from hepatitis C) therewith, followed by detecting the anti-HCV-protein antibody. If the HCV protein is detected in the protein extracted from the cell clone, it can be judged that, in the cell clone, the replicon RNA derived from HCV is continuously replicating and expressing the HCV protein.

Thus, a cell clone (replicon-replicating cell clone) wherein the replicon RNA of interest has been confirmed to be continuously replicating can be obtained.

The replicon-replicating cell of the present invention can be suitably used also for producing an HCV protein. Production of an HCV protein from replicon-replicating cells can be carried out according to a conventional method by those skilled in the art. More particularly, for example, replicon-replicating cells are cultured, and, from the obtained culture (which contains cultured cells and a culture medium), the protein can be obtained by a conventional method.

The replicon RNA-replicating cell of the present invention can be used also as a test system for screening or evaluation of substances that suppress replication of HCV or translation of HCV proteins. More particularly, for example, by culturing replicon-replicating cells in the presence of a drug candidate substance and detecting replication of a replicon RNA in the obtained culture, followed by judging whether the substance suppresses replication of the replicon RNA, a substance that suppresses replication of HCV can be screened. In such a case, the detection of replication of the replicon RNA in the obtained culture may be either detection of the amount or the presence/absence of the replicon RNA in RNA extracted from the replicon RNA-replicating cells, or detection of the amount or the presence/absence of an HCV protein contained in protein in the culture or in the replicon RNA-replicating cells contained in the culture.

Further, by culturing replicon-replicating cells in the presence of a drug candidate substance and detecting a protein derived from the replicon RNA in the obtained culture, followed by judging whether the substance suppresses production of the protein, a substance that suppresses translation of the protein of HCV can be screened.

The drug candidate substance is not restricted, and may be, for example, a low-molecular synthetic compound or a compound contained in a natural product. Further, the drug candidate substance may be a peptide or a nucleic acid. Test substances may be used individually in the screening, or a compound library containing these substances may be used.

EXAMPLES

The present invention will now be described more particularly by way of Examples. However, the present invention is not limited thereto.

Example 1

Cloning of Hepatitis C Virus

1. Origin of Virus

Using a 27-G disposable injection needle, 100 µl of the serum of a patient infected with the genotype 1a (G-52998-035: International Reagents Co., Ltd.) was intravenously inoculated to a human hepatocyte chimeric mouse (Tateno et al. American Journal Pathology 2004, 165:901-912) prepared by PhoenixBio Co., Ltd., at the orbital venous plexus. From the following week of the inoculation, 10 µL of blood was collected once per week under diethyl ether anesthesia at the orbital venous plexus using Intramedic™ Polyethylene Tubing (0.58×0.965 mm, Becton-Dickinson Japan, Tokyo). Immediately after the blood collection, the blood was transferred to a 500-µl at safe-lock microtest tube containing a serum separation agent (Eppendorf Co., Ltd., Tokyo). The blood was left to stand for 5 minutes at room temperature and then centrifuged at 13200×g for 3 minutes to obtain serum, which was then stored at −80° C. From 1 µL of the collected serum, RNA was extracted using SepaGene RV-R (Sanko Junyaku Co., Ltd., Tokyo), and the RNA was dissolved in 10 µL of Nuclease-free water (Ambion, Inc./Applied Biosystems Japan, Tokyo) containing 1 mM DTT (Promega KK, Tokyo) and 4 U/mL ribonuclease inhibitor (TAKARA BIO INC., Shiga). The dissolved RNA was stored at −80±10° C. until quantification of the serum HCV RNA.

When the serum HCV RNA was quantified, HCV RNA synthesized in vitro was used as a copy standard. The quantification limit of the serum HCV RNA level was from $4.0 \times 10^4$ copies/mL to $1.0 \times 10^9$ copies/mL in the serum.

In the PCR reaction solution, 2.5 µL of the stock solution of the dissolved RNA or diluted RNA was used, and PCR was carried out using TaqMan EZ RT-PCR Core Reagents (Applied Biosystems Japan, Tokyo). The PCR reaction was performed at 50° C. for 2 minutes→at 60° C. for 30 minutes→at 95° C. for 5 minutes→(at 95° C. for 20 seconds→at 62° C. for 1 minute)×50 cycles, and the reaction and analysis were carried out using ABI Prism 7700 (Applied Biosystems Japan). The serum HCV RNA level was calculated by averaging the levels measured in 2 wells.

As primers and a probe, the following sequences were used.

```
Forward primer:
                                (SEQ ID NO: 6)
5'-CGGGAGAGCCATAGTGG-3'

Reverse primer:
                                (SEQ ID NO: 7)
5'-AGTACCACAAGGCCTTTCG-3'

Probe:
                                (SEQ ID NO: 8)
5'-CTGCGGAACCGGTGAGTACAC-3'
(5'-end: FAM; 3'-end: TAMRA)
```

The results indicate that infection of HCV was established and the blood virus level was maintained at a high level. The process, and timing of collection of the serum are shown in FIG. 1.

As a result, it was revealed that this virus maintains a high infection/replication efficiency.

2. Preparation of Total RNA of Virus and Synthesis of cDNA

From 10 µl of the chimeric mouse serum obtained in the above-described 1, total RNA was extracted by the AGPC (acid-guanidinium-isothiocyanate-phenol-chloroform) method using ISOGEN-LS (manufactured by Nippon Gene Co., Ltd.), and the extracted total RNA was dissolved in RNase-free water. Using the thus obtained total RNA, reverse transcription was performed with a primer (the antisense sequence from the 9569th nucleotide having a length of 21 nucleotides) prepared based on the sequence of the HCV-H77 strain (accession No: AF011751), using LongRange Reverse Transcriptase (manufactured by Qiagen), at 25° C. for 10 minutes and then at 42° C. for 90 minutes, followed by treatment for inactivation of the reverse transcriptase at 85° C. for 5 minutes, addition of RNase H (manufactured by Invitrogen) and incubation at 37° C. for 20 minutes to digest viral RNA so that only cDNA exists.

3. Determination of Sequence

Figure 2:
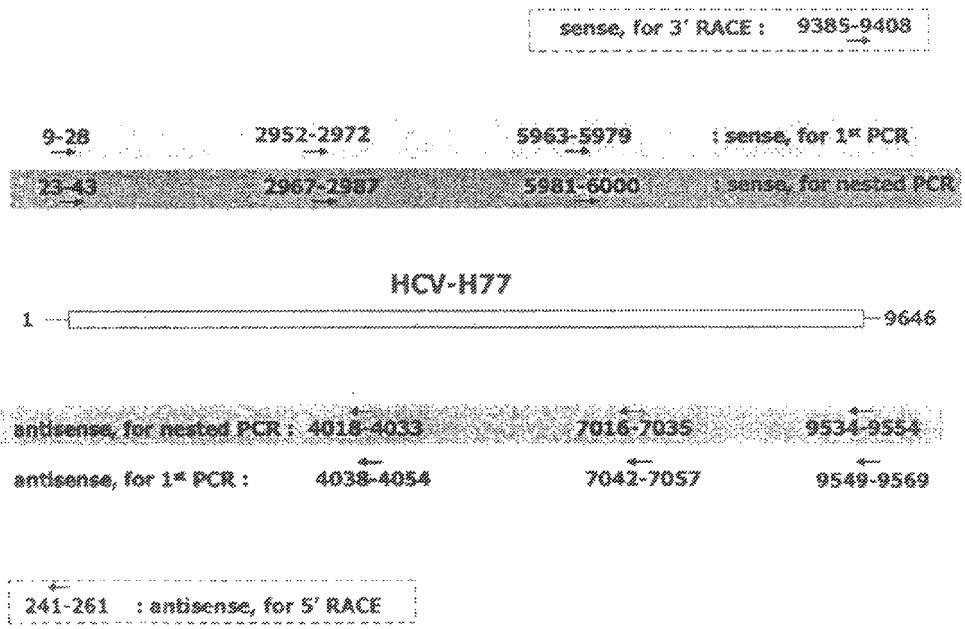

Nested PCR was performed using the synthesized cDNA as a template for PCR. The reaction was carried out by adding the above-described reaction solution at a ratio of 1/10 with respect to the total volume, and using Phusion DNA polymerase (manufactured by Fynnzymes) as the enzyme. PCR primers were designed based on the sequence of HCV-H77 (FIG. 2). Three fragments, that is, those corresponding to nucleotide positions 9 to 4054, 2952 to 7057, and 5963 to 9569, are expected to be amplified in the first PCR reaction. In the second PCR, 3 fragments, that is, those corresponding to nucleotide positions 23-4033, 2967-7035, and 5981-9554, were amplified using the respective reaction solutions as templates. In the first PCR and the second PCR, 20 cycles and 30 cycles, respectively, of the reaction under the conditions of: denaturation at 98° C. for 10 seconds; annealing at 60° C. for 30 seconds; and then at 72° C. for 2.5 minutes were performed. These DNA fragments were separated by agarose electrophoresis and purified using Wizard SV gel and PCR clean-up system (manufactured by Promega), followed by being cloned using TOPO cloning kit (manufactured by Invitrogen). Appeared colonies were picked up and allowed to grow, followed by purification of plasmid DNAs and determination of the sequences of not less than 15 clones for each fragment using Big Dye Terminator Mix and an automated DNA sequencer model 3100 (manufactured by Applied Biosystems). From the obtained sequence information, the most frequent nucleotide at each nucleotide position was determined to obtain a consensus sequence. At each of all the nucleotide positions, not less than 11 clones out of 15 clones shared the same nucleotide.

Subsequently, using the 5'-RACE method and the 3'-RACE method, the nucleotide sequences of the 5'-end and the 3'-end of the viral RNA were determined. For determination of the 5'-end sequence, 5'-end cDNA was synthesized using the 5'-RACE system (manufactured by Invitrogen, Version 2.0) and a primer (the antisense sequence from the 261st nucleotide having a length of 21 nucleotides), and a poly-C sequence was added to the 5'-end of the synthesized cDNA by terminal deoxynucleotidyl transferase. Thereafter, the 5'-end was amplified by nested-PCR.

Further, in order to determine the 3'-end sequence, a poly-A sequence was added to the extracted viral RNA using poly(A) polymerase (manufactured by Takara Shuzo Co., Ltd.), and cDNA was prepared using an oligo d(T) primer, followed by PCR amplification using a specific primer (the sense sequence from the 9385th nucleotide having a length of 24 nucleotides) and the oligo d(T) primer. These DNA fragments were similarly subjected to TOPO cloning, and the sequences of not less than 10 clones were determined, to obtain a consensus sequence. The positions in the HCV-H77 sequence and the lengths of the primers used for the cloning are shown in FIG. 2. Among these, the primers corresponding to the regions 2952 to 2972 and 5981 to 6000 were prepared according to the RMT sequence based on the sequence information preliminarily obtained.

Thus, a consensus sequence of the total viral genome was obtained, and the strain was designated the HCV-RMT strain. The obtained nucleotide sequence, which has a length of 9598 nucleotides, is shown in SEQ ID NO:1. The nucleotide sequence had a long translated region between position 342 and position 9374, which encodes 3011 amino acid residues. The amino acid sequence of the translated region is described in SEQ ID NO:2.

The genomic nucleotide sequence of the RMT strain had a homology of 92.8% in terms of the nucleotide sequence, and 95.1% in terms of the amino acid sequence, to the H77 strain, which similarly belongs to the 1a type Example 2

Confirmation of Infectivity to Chimeric Mouse

1. Construction of Viral RNA Expression Vector

Figure 3:
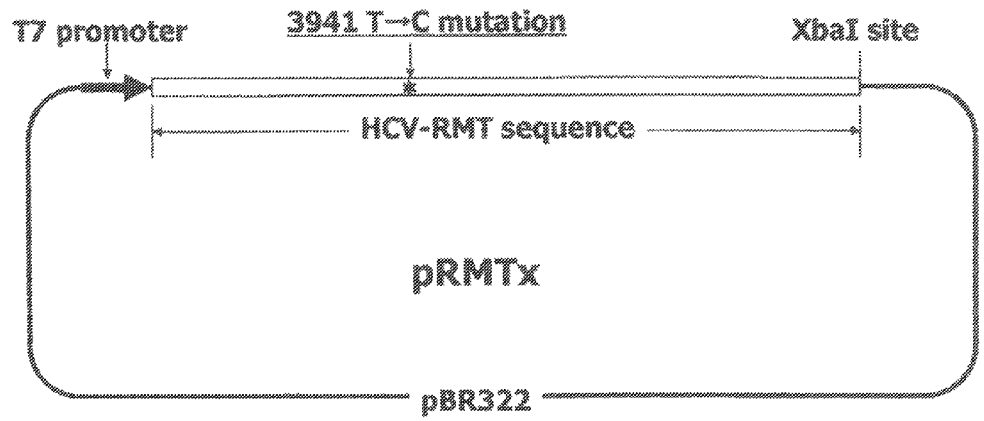

An expression vector was prepared using the HCV-RMT strain sequence obtained in Example 1. A promoter sequence for T7 RNA polymerase was linked to the 5'-end, and a restriction enzyme XbaI-cleavage site was linked to the 3'-end. The resulting fragment was inserted into pBR322. Further, T at nucleotide position 3941 was converted to C, to destroy the XbaI cleavage site in the HCV-RMT sequence, without changing the amino acid sequence. For introduction of the mutation, QuikChangeII Site-Directed Mutagenesis kit (manufactured by Stratagene) was used. Thus, the expression vector was made such that, by digesting the vector with XbaI, removing single-stranded portions with mung bean nuclease and using the resulting DNA fragment as a template for T7 polymerase, RNA having the length of the HCV genome can be synthesized. The prepared expression vector was designated pRMTx, and its structure is shown in FIG. 3.

2. Preparation HCV-RMT Strain RNA and Injection Thereof to Liver of Human Hepatocyte Chimeric Mouse pRMTx was sufficiently digested with XbaI, and single-stranded portions after the XbaI digestion were removed with Mung bean nuclease. Subsequently, using this DNA fragment, RNA was synthesized using RiboMAX (manufactured by Promega KK). After reaction at 37° C. for 90 minutes, DNase treatment was carried out at 37° C. for 30 minutes, and the synthesized RNA was purified through a microspin-G25 column (manufactured by GE HealthCare), followed by being subjected to phenol extraction and ethanol precipitation. A part of the thus obtained RNA was subjected to agarose electrophoresis to confirm that RNA having the desired size was produced.

A human hepatocyte chimeric mouse of 10 to 14 weeks old which had human albumin in the mouse blood at a concentration of not less than 6 mg/ml was subjected to celiotomy, and 400 µL/75 µg of this RNA was injected to the liver directly using an injector. From the following week of the inoculation, 10 µL of blood was collected once per week under diethyl ether anesthesia at the orbital venous plexus using Intramedic™ Polyethylene Tubing, and the copy number of the HCV-RNA in the serum was measured in the same manner as described above. Further, pRMTx-E1202G, which was prepared by introducing E1202G (a mutation replacing glutamic acid at position 1202 of SEQ ID NO:2 with glycine) to pRMTx, was also subjected to a similar experiment.

Figure 4:
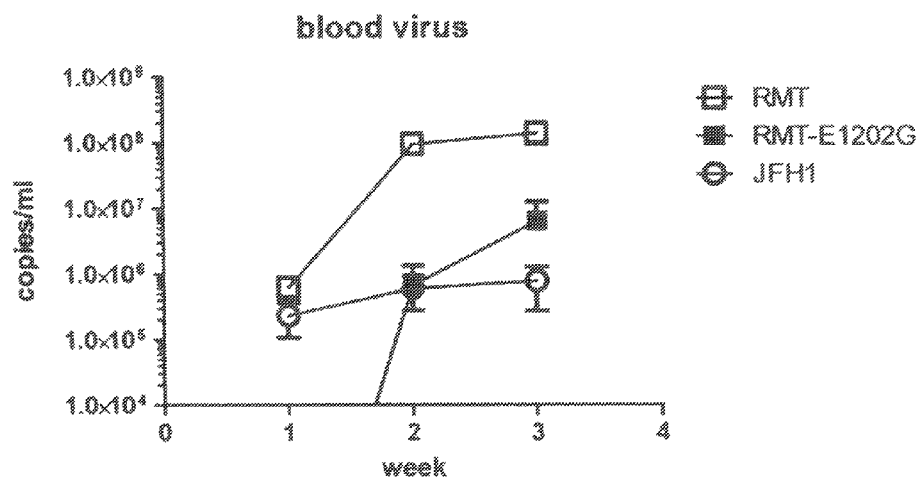

As a result, as shown in FIG. 4, in the case of the HCV-RMT strain, a higher copy number of the HCV RNA was detected in the chimeric mouse serum, compared to the JFH1 strain used as a control. Thus, it was revealed that the HCV-RMT strain has a high replication capacity in the chimeric mouse. Further, also in the case of the HCV-RMT-E1202G strain, a higher HCV RNA copy number was detected 3 weeks later, compared to the JFH1 strain.

Example 3

Figure 5:
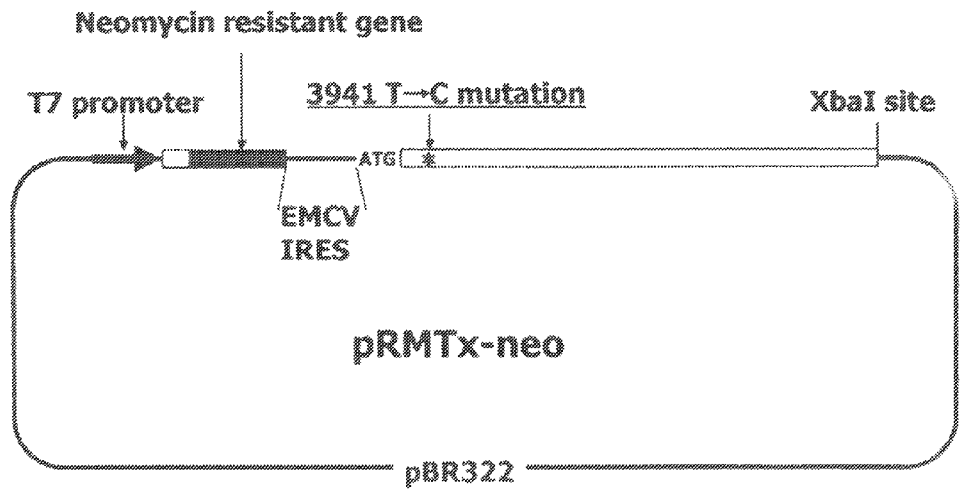

Confirmation of Replicon-Replicating Capacity and Identification of Acclimation Mutations 1. Construction of Replicon RNA Expression Vector According to a conventional method (Lohman et al., Science, 1999), nucleotide positions 391 to 3419 of the HCV-RMT sequence in the pRMTx vector were deleted, and, instead, a sequence for a neomycin resistance protein and, subsequently, an EMCV-IRES sequence and an initiation codon were inserted. The prepared expression vector was designated pRMTx-neo, and its structure is shown in FIG. 5; the nucleotide sequence of the replicon RNA prepared from the expression vector is shown in SEQ ID NO:5; and the amino acid sequences of the proteins produced by translation are shown in SEQ ID NOs:6 (neomycin resistance protein) and 7 (nonstructural protein).

2. Preparation of Replicon RNA pRMTx-neo was sufficiently digested with XbaI, and single-stranded portions after the XbaI digestion were removed with Mung bean nuclease. Subsequently, using this DNA fragment, RNA was synthesized using RiboMAX (manufactured by Promega KK). After reaction at 37° C. for 90 minutes, DNase treatment was carried out at 37° C. for 30 minutes, and the synthesized RNA was purified through a microspin-G25 column (manufactured by GE HealthCare), followed by being subjected to phenol extraction and ethanol precipitation. A part of the thus obtained RNA was subjected to agarose electrophoresis to confirm that RNA having the desired size was produced.

3. Establishment of Replicon-Replicating Cell Clone and Identification of Replicon Sequence Mutations To Huh7 cells, 30 µg of the synthesized replicon RNA prepared in the above 2 was introduced by electroporation. The Huh7 cell to which the RNA was introduced was plated on a culture dish, and, after 16 hours of culture, G418 (neomycin) was added to the culture dish at a concentration of 300 µg/ml. Thereafter, the culture was continued, with the culture medium being replaced 3 times per week. As a result, 2 colonies were formed 21 days after the plating. These colonies were cloned and the culture was continued, after which one strain of a replicon-replicating clone maintaining stable replication was successfully established. From the established clone, total RNA was prepared, and PCR amplification was carried out to determine a consensus sequence. As a result, 3 mutations, that is, change from glutamic acid to valine at amino acid position 1056 (E1056V), change from glutamic acid to glycine at amino acid position 1202 (E1202G) and change from alanine to threonine at amino acid position 2199 (A2199T) were confirmed.

4. Elucidation of Usefulness of Replicon Sequence Mutations

Figure 6:
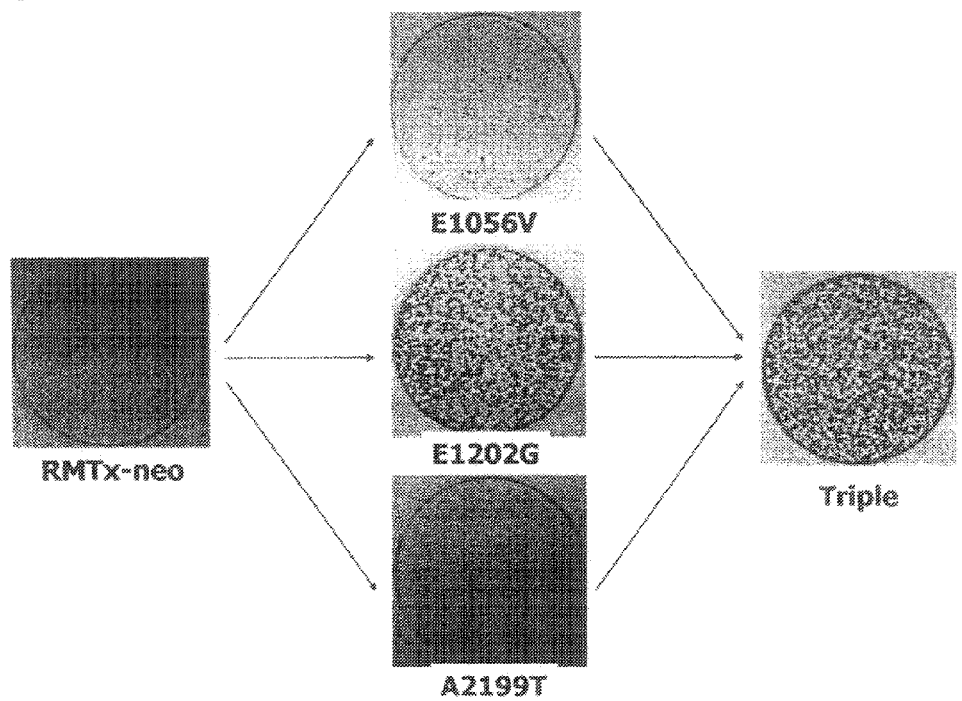

The 3 mutations confirmed in the replicon-replicating clone were introduced to pRMTx-neo individually or in combination. From the vectors to which the mutations were introduced, replicon RNAs were prepared, and 5 µg each of these replicon RNAs were introduced to Huh7 cells by electroporation in the same manner as in the above-described 3. After 21 days of G418 selection, viable cells were stained with crystal violet, and, as a result, colony formation was confirmed as shown in FIG. 6.

Based on these results obtained by comparison among the 3 mutations, the degree of enhancement of the growth capacity in the Huh7 cells was highest in E1202G, followed by E1056V and A2199T in this order. Further, it was revealed that the clone to which all the 3 mutations were introduced has a higher growth capacity (replication capacity) than any of the clones to which the mutations were introduced alone.

Example 4

Figure 7:
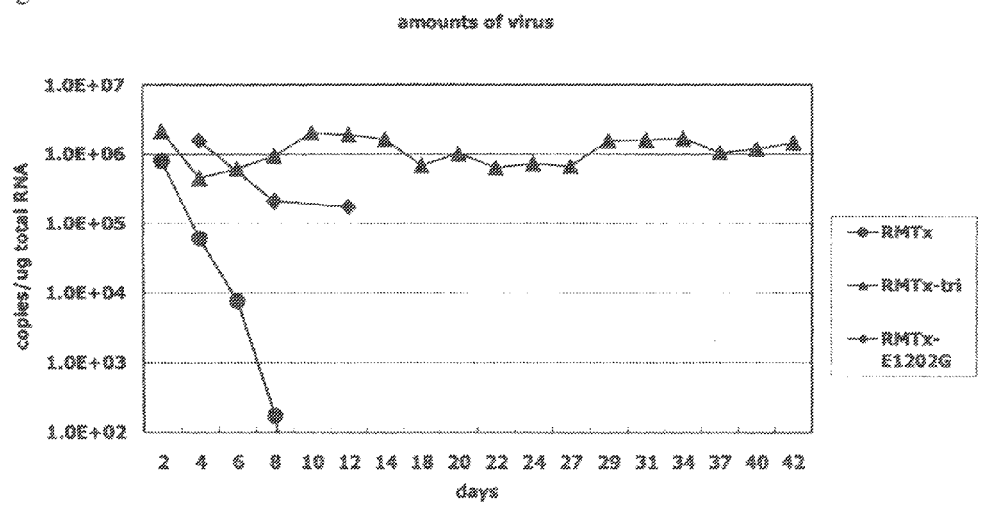

Confirmation of Growth Capacity of Acclimation Mutation-Introduced HCV-RMT Strain in Cultured Cells E1202G or the 3 acclimation mutations (E1202G, E1056V and A2199T) was/were introduced to pRMTx, and the obtained vectors were designated pRMTx-E1202G and pRMTx-tri, respectively. From pRMTx, pRMTx-E1202G and pRMTx-tri, viral genomic RNAs were prepared (RMT, RMT-E1202G and RMT-tri, respectively), and 30 µg each of the prepared genomic RNAs were introduced to Huh7 cells by electroporation. The cells were plated on a culture dish and subcultured 3 to 4 times per week, during which the cell were sampled. From the sampled cells, total RNA was purified by the AGPC method, and the copy number of the HCV genome per 1 µg of the total RNA was quantified according to a conventional method (Takeuchi et al., Gastroenterology, 1999) by reverse transcription real-time PCR using Quanti-Tect Multiplex PCR kit (manufactured by Qiagen). Daily changes in the copy number of the HCV genome in the cells to which RMT-RNA, RMT-E1202G-RNA and RMT-tri-RNA were respectively introduced are shown in FIG. 7. It was revealed that, while RMT-RNA, which has no acclimation mutation, quickly disappears, RMT-tri-RNA maintains a viral genomic amount of about $1\times10^6$ copies/µg for not less than 1 month. Further, it was revealed that RMT-E1202G-RNA also maintains a viral genomic amount of not less than $1\times10^5$ copies/µg even on Day 12.

Further, 10 days after the introduction of the genome, the cells in the state where the HCV genome was maintained were plated on a 96-well plate, and an agent was added thereto 16 hours later, followed by purification of total RNA 48 hours later from each well using ABI prizm 6100 and a purification kit (manufactured by Applied Biosystems). The HCV amount in the RNA, which was obtained by the above real-time PCR, and the total RNA amount quantified using an absorption spectrophotometer are shown in FIG. 8. As anti-HCV agents, an HCV polymerase inhibitor (MK0608), HCV protease inhibitor (BILN2061), IFN-α and cyclophilin inhibitor (cyclosporin A) were used. For all the anti-HCV agents, growth inhibition capacities against HCV, whose levels were almost the same as those described in documents were observed, and it was thereby confirmed that the cells wherein the HCV-RMT strain is continuously growing are useful as an evaluation system for anti-HCV agents.

Example 5

Confirmation of Production of Infectious Virus from Cells Wherein Acclimation Mutation-Introduced HCV-RMT Strain is Continuously Growing The RMT-tri-introduced cells, wherein the growth was confirmed in Example 4, single cell culture was carried out by the limiting dilution method. Selection was carried out among clones using as an index the amount of the intracellular virus, and the #11 clone, wherein expression of the HCV-core protein could be confirmed in all the cells by the fluorescent antibody method and the intracellular HCV genomic amount was $1\times10^8$ copies/µg, was obtained. By treating uninfected Huh7 cells with the culture supernatant of the clone after filtration through a 0.22 µm-filter, infected cells were confirmed by the fluorescent antibody method applied to the core protein (FIG. 9). By reducing the total volume of the culture supernatant to about one seventieth using an ultrafiltration membrane, the HCV copies were 40-fold concentrated. The concentrated culture supernatant showed a 45 times higher infectivity titer compared to the culture supernatant before the concentration.

The HCV sequence in the #11 cells was determined and, as a result, it was revealed that, compared to the RMT strain, all the 10 clones sequenced had the mutation at amino acid position 2321 from serine to proline (S2321P) and the mutation at amino acid position 2889 from leucine to phenylalanine (L2889F). These mutations were suggested to be contributing to the infectivity and the growth capacity of the RMT strain.

Industrial Applicability

By using the polynucleotide of the present invention derived from the HCV-RMT strain, which belongs to the genotype 1a, and the identified acclimation mutations, an HCV replicon RNA and the HCV genomic RNA of the genotype 1 showing good replication efficiency can be prepared at a high probability. Replicon-replicating cells to which the replicon RNA was introduced, and HCV-growing cells to which the HCV genomic RNA was introduced can be used as culture systems for continuous production of an RNA derived from HCV, or an HCV protein. Further, the replicon-replicating cells and the HCV-growing cells can be used as test systems for screening various substances that influence replication of HCV and/or translation of HCV proteins.

[Description of Sequence Listing]
1. Nucleotide sequence of entire genome of HCV-RMT strain
2. Amino acid sequence encoded by HCV-RMT strain
3. Nucleotide sequence of replicon derived from HCV-RMT strain
4. Amino acid sequence of neomycin resistance protein
5. Amino acid sequence of nonstructural protein encoded by HCV-RMT strain
6. Nucleotide sequence of Forward Primer
7. Nucleotide sequence of Reverse Primer
8. Nucleotide sequence of probe

The invention claimed is:

1. A recombinant polynucleotide encoding an amino acid sequence having at least 99% identity to the entire sequence set forth in SEQ ID NO: 2, wherein said amino acid sequence comprises a glutamic acid to glycine substitution at position 1202 of SEQ ID NO: 2.

2. The recombinant polynucleotide of claim 1, wherein the encoded amino acid sequence further comprises a serine to proline substitution at position 2321 and a leucine to phenylalanine substitution at position 2889 of SEQ ID NO: 2.

3. The recombinant polynucleotide of claim 1, wherein said polynucleotide comprises a nucleotide sequence at least 97% identical to the entire sequence set forth in SEQ ID NO: 1, and wherein, in cases where the polynucleotide is RNA, the nucleotide "t" in said sequence is replaced with a "u".

4. A functional recombinant hepatitis C virus (HCV) particle comprising the recombinant polynucleotide of claim 1.

5. An isolated cell to which the recombinant polynucleotide of claim 1 has been introduced and which produces a functional recombinant HCV.

6. A recombinant polynucleotide encoding an amino acid sequence having at least 98% identity to the entire sequence set forth in SEQ ID NO: 2, wherein said amino acid sequence comprises a glutamic acid to glycine substitution at position 1202, a glutamic acid to valine substitution at position 1056, and a alanine to threonine substitution at position 2199 of SEQ ID NO: 2.

7. The recombinant polynucleotide of claim 6, wherein the encoded amino acid sequence further comprises a serine to proline substitution at position 2321 and a leucine to phenylalanine substitution at position 2889 of SEQ ID NO: 2.

8. The recombinant polynucleotide of claim 6, wherein said polynucleotide comprises a nucleotide sequence at least 97% identical to the entire sequence set forth in SEQ ID NO: 1, and wherein, in cases where the polynucleotide is RNA, the nucleotide "t" in said sequence is replaced with a "u".

9. A functional recombinant hepatitis C virus particle comprising the recombinant polynucleotide of claim 6.

10. An isolated cell to which the recombinant polynucleotide of claim 6 has been introduced and which produces a functional recombinant HCV.

\* \* \* \* \*

```
                        SEQUENCE LISTING

<160> NUMBER OF SEQ ID NOS: 8

<210> SEQ ID NO 1
<211> LENGTH: 9598
<212> TYPE: DNA
<213> ORGANISM: Hepatitis C virus
<220> FEATURE:
<221> NAME/KEY: 5'UTR
<222> LOCATION: (1)..(341)
<220> FEATURE:
<221> NAME/KEY: CDS
<222> LOCATION: (342)..(9374)
<220> FEATURE:
<221> NAME/KEY: misc_feature
<222> LOCATION: (342)..(914)
<223> OTHER INFORMATION: Core
<220> FEATURE:
<221> NAME/KEY: misc_feature
<222> LOCATION: (915)..(1490)
<223> OTHER INFORMATION: E1
<220> FEATURE:
<221> NAME/KEY: misc_feature
<222> LOCATION: (1491)..(2768)
<223> OTHER INFORMATION: E2
<220> FEATURE:
<221> NAME/KEY: misc_feature
<222> LOCATION: (2769)..(3419)
<223> OTHER INFORMATION: NS2
<220> FEATURE:
<221> NAME/KEY: misc_feature
<222> LOCATION: (3420)..(5312)
<223> OTHER INFORMATION: NS3
<220> FEATURE:
<221> NAME/KEY: misc_feature
<222> LOCATION: (5313)..(5474)
<223> OTHER INFORMATION: NS4A
<220> FEATURE:
<221> NAME/KEY: misc_feature
<222> LOCATION: (5475)..(6257)
<223> OTHER INFORMATION: NS4B
<220> FEATURE:
<221> NAME/KEY: misc_feature
<222> LOCATION: (6258)..(7601)
<223> OTHER INFORMATION: NS5A
<220> FEATURE:
<221> NAME/KEY: misc_feature
<222> LOCATION: (7602)..(9374)
<223> OTHER INFORMATION: NS5B
<220> FEATURE:
<221> NAME/KEY: 3'UTR
<222> LOCATION: (9375)..(9598)

<400> SEQUENCE: 1
gccagccccc tgatgggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac c atg agc acg aat cct     356
                                             Met Ser Thr Asn Pro
                                               1               5 aaa cct caa aga aaa acc aaa cgt aac acc aac cgt cgc cca cag gac       404
```

```
            Lys Pro Gln Arg Lys Thr Lys Arg Asn Thr Asn Arg Arg Pro Gln Asp
                         10                  15                  20 gtc aag ttc ccg ggt ggc ggt cag atc gtt ggt gga gtt tac ttg ttg              452
Val Lys Phe Pro Gly Gly Gly Gln Ile Val Gly Gly Val Tyr Leu Leu
             25                  30                  35 ccg cgc agg ggc cct aga ttg ggt gtg cgc gcg acg agg aag act tcc              500
Pro Arg Arg Gly Pro Arg Leu Gly Val Arg Ala Thr Arg Lys Thr Ser
         40                  45                  50 gag cgg tcg caa cct cga ggt aga cgt cag cct atc ccc aag gcg cgt              548
Glu Arg Ser Gln Pro Arg Gly Arg Arg Gln Pro Ile Pro Lys Ala Arg
 55                  60                  65 cgg ccc gag ggc agg acc tgg gct cag ccc ggg tac cct tgg ccc ctc              596
Arg Pro Glu Gly Arg Thr Trp Ala Gln Pro Gly Tyr Pro Trp Pro Leu
 70                  75                  80                  85 tat ggc aat gag ggc tgc ggg tgg gcg gga tgg ctc ctg tcc ccc cgt              644
Tyr Gly Asn Glu Gly Cys Gly Trp Ala Gly Trp Leu Leu Ser Pro Arg
             90                  95                 100 ggc tct cgg cct agc tgg ggc ccc aca gac ccc cgg cgc agg tca cgc              692
Gly Ser Arg Pro Ser Trp Gly Pro Thr Asp Pro Arg Arg Arg Ser Arg
        105                 110                 115 aat ttg ggt aag gtc atc gat acc ctc acg tgt ggc ttc gcc gac ctc              740
Asn Leu Gly Lys Val Ile Asp Thr Leu Thr Cys Gly Phe Ala Asp Leu
    120                 125                 130 atg ggg tac att ccg ctc gtc ggc gcc cct ctt ggg ggc gct gcc agg              788
Met Gly Tyr Ile Pro Leu Val Gly Ala Pro Leu Gly Gly Ala Ala Arg
135                 140                 145 gcc ctg gcg cat ggc gtc cgg gtt ctg gaa gac ggc gtg aac tat gca              836
Ala Leu Ala His Gly Val Arg Val Leu Glu Asp Gly Val Asn Tyr Ala
150                 155                 160                 165 aca ggg aac ctt cct ggt tgc tct ttc tct atc ttc ctt cta gcc ctg              884
Thr Gly Asn Leu Pro Gly Cys Ser Phe Ser Ile Phe Leu Leu Ala Leu
        170                 175                 180 ctc tct tgc ctg act gtg ccc gca tca gcc tac caa gta cgc aac tcc              932
Leu Ser Cys Leu Thr Val Pro Ala Ser Ala Tyr Gln Val Arg Asn Ser
            185                 190                 195 tcg ggc ctt tac cat gtc acc aat gat tgc cct aac tcg agt att gtg              980
Ser Gly Leu Tyr His Val Thr Asn Asp Cys Pro Asn Ser Ser Ile Val
        200                 205                 210 tac gag acg gcc gac acc att cta cac tct ccg ggg tgt gtt cct tgc             1028
Tyr Glu Thr Ala Asp Thr Ile Leu His Ser Pro Gly Cys Val Pro Cys
215                 220                 225 gtt cgc gag gat aac gcc tcg aga tgt tgg gtg ccg gtg gcc ccc aca             1076
Val Arg Glu Asp Asn Ala Ser Arg Cys Trp Val Pro Val Ala Pro Thr
230                 235                 240                 245 gtg gcc acc agg gac ggc aaa ctc ccc aca acg cag ctt cga cgt cac             1124
Val Ala Thr Arg Asp Gly Lys Leu Pro Thr Thr Gln Leu Arg Arg His
        250                 255                 260 atc gat ctg ctt gtc ggg agc gcc acc ctc tgc tcg gcc ctc tat gta             1172
Ile Asp Leu Leu Val Gly Ser Ala Thr Leu Cys Ser Ala Leu Tyr Val
            265                 270                 275 ggg gac ttg tgc ggg tcc gtc ttt ctt gtc agc caa ctg ttc act ttt             1220
Gly Asp Leu Cys Gly Ser Val Phe Leu Val Ser Gln Leu Phe Thr Phe
        280                 285                 290 tcc ccc agg cgc cac tgg aca acg caa gac tgc aac tgt tct atc tac             1268
Ser Pro Arg Arg His Trp Thr Thr Gln Asp Cys Asn Cys Ser Ile Tyr
295                 300                 305 ccc ggc cat ata acg ggt cac cgc atg gcg tgg gat atg atg atg aac             1316
Pro Gly His Ile Thr Gly His Arg Met Ala Trp Asp Met Met Met Asn
310                 315                 320                 325 tgg tcc cct acg gtc gcg ctg gta atg gct cag ctg ctc agg gtc cca             1364
```

```
Trp Ser Pro Thr Val Ala Leu Val Met Ala Gln Leu Leu Arg Val Pro
            330                 335                 340 caa gcc atc ttg gac atg atc gct ggt gct cac tgg gga gtc cta gcg    1412
Gln Ala Ile Leu Asp Met Ile Ala Gly Ala His Trp Gly Val Leu Ala
                345                 350                 355 ggc ata gcg tat ttc tcc atg gtg ggg aac tgg gcg aag gtt ctg gtg    1460
Gly Ile Ala Tyr Phe Ser Met Val Gly Asn Trp Ala Lys Val Leu Val
            360                 365                 370 gtg ctg ttg ctg ttt gcc ggc gtt gac gcg caa acc tac gtc acc ggg    1508
Val Leu Leu Leu Phe Ala Gly Val Asp Ala Gln Thr Tyr Val Thr Gly
        375                 380                 385 ggg agt gcc gct cgg ggc gcg tcc gga ctc gcc aac ctt ttt aca ccg    1556
Gly Ser Ala Ala Arg Gly Ala Ser Gly Leu Ala Asn Leu Phe Thr Pro
390                 395                 400                 405 ggc gcc aag cag gat atc cag ctg atc aac acc aat ggc agt tgg cac    1604
Gly Ala Lys Gln Asp Ile Gln Leu Ile Asn Thr Asn Gly Ser Trp His
                410                 415                 420 atc aac cgt acg gcc ttg aac tgt aat gcg agc ctt gac act ggt tgg    1652
Ile Asn Arg Thr Ala Leu Asn Cys Asn Ala Ser Leu Asp Thr Gly Trp
            425                 430                 435 gtc gca ggg ctc ttt tat tac cat aaa ttc aac tct tca ggt tgc cct    1700
Val Ala Gly Leu Phe Tyr Tyr His Lys Phe Asn Ser Ser Gly Cys Pro
        440                 445                 450 gag agg atg gcc agc tgc aaa ccc ctt gcc gat ttc gac cag ggc tgg    1748
Glu Arg Met Ala Ser Cys Lys Pro Leu Ala Asp Phe Asp Gln Gly Trp
455                 460                 465 ggc cct att cgc cac gcc aac gga agc ggc ccc gaa cat cga ccc tac    1796
Gly Pro Ile Arg His Ala Asn Gly Ser Gly Pro Glu His Arg Pro Tyr
470                 475                 480                 485 tgc tgg cac tac ccc cca aaa cct tgt ggt atc gtg tca gca cag act    1844
Cys Trp His Tyr Pro Pro Lys Pro Cys Gly Ile Val Ser Ala Gln Thr
                490                 495                 500 gta tgt ggc cca gtg tat tgc ttc acc ccc agc ccc gta gtg gtg gga    1892
Val Cys Gly Pro Val Tyr Cys Phe Thr Pro Ser Pro Val Val Val Gly
            505                 510                 515 acg acc aac cgg ttg ggc gtg ccc acc tac agt tgg ggc acc aat gat    1940
Thr Thr Asn Arg Leu Gly Val Pro Thr Tyr Ser Trp Gly Thr Asn Asp
        520                 525                 530 acg gac gtt ttc gtc ctt aat aac acc agg cca ccg ttg ggc aat tgg    1988
Thr Asp Val Phe Val Leu Asn Asn Thr Arg Pro Pro Leu Gly Asn Trp
535                 540                 545 ttc ggt tgc act tgg atg aac tca tct gga ttt acc aaa gtg tgc gga    2036
Phe Gly Cys Thr Trp Met Asn Ser Ser Gly Phe Thr Lys Val Cys Gly
550                 555                 560                 565 gcg cct cct tgt gtc atc gga gga gtg ggc aac aac acc ctg cac tgc    2084
Ala Pro Pro Cys Val Ile Gly Gly Val Gly Asn Asn Thr Leu His Cys
                570                 575                 580 ccc act gac tgt ttc cgc aag cat ccg gaa gcc acg tac tct cgg tgt    2132
Pro Thr Asp Cys Phe Arg Lys His Pro Glu Ala Thr Tyr Ser Arg Cys
            585                 590                 595 ggc tcc ggt ccc tgg atc acg ccc agg tgc ctg gtc cac tat cct tat    2180
Gly Ser Gly Pro Trp Ile Thr Pro Arg Cys Leu Val His Tyr Pro Tyr
        600                 605                 610 agg ctt tgg cat tat cct tgc acc gtc aac tac acc ctg ttc aaa gtc    2228
Arg Leu Trp His Tyr Pro Cys Thr Val Asn Tyr Thr Leu Phe Lys Val
615                 620                 625 agg atg tac gtg gga ggg gtc gag cac agg ctg gaa gtt gct tgc aac    2276
Arg Met Tyr Val Gly Gly Val Glu His Arg Leu Glu Val Ala Cys Asn
630                 635                 640                 645 tgg acg cgg ggc gag cgt tgt gat ctg gac gac agg gac agg tcc gag    2324
```

-continued

| | | |
|---|---|---|
| Trp Thr Arg Gly Glu Arg Cys Asp Leu Asp Asp Arg Asp Arg Ser Glu<br>                        650                    655                    660 | |
| ctc agc ccg ctg ctg ctg tcc acc aca cag tgg cag gtc ctc ccg tgt<br>Leu Ser Pro Leu Leu Leu Ser Thr Thr Gln Trp Gln Val Leu Pro Cys<br>                665                    670                    675 | 2372 |
| tct ttc acg acc ttg cca gcc ttg act acc ggc ctc atc cac ctc cac<br>Ser Phe Thr Thr Leu Pro Ala Leu Thr Thr Gly Leu Ile His Leu His<br>                680                    685                    690 | 2420 |
| cag aac atc gtg gac gtg caa tac ctg tac ggg gtg ggg tca agc att<br>Gln Asn Ile Val Asp Val Gln Tyr Leu Tyr Gly Val Gly Ser Ser Ile<br>        695                    700                    705 | 2468 |
| gtg tcc tgg gcc atc aag tgg gaa tac gtc atc ctt ctg ttc ctc ctg<br>Val Ser Trp Ala Ile Lys Trp Glu Tyr Val Ile Leu Leu Phe Leu Leu<br>710                    715                    720                    725 | 2516 |
| ctt gca gac gcg cgc atc tgc tcc tgc ttg tgg atg atg cta ctc ata<br>Leu Ala Asp Ala Arg Ile Cys Ser Cys Leu Trp Met Met Leu Leu Ile<br>                    730                    735                    740 | 2564 |
| tcc caa gcg gag gcg gct ttg gag aac ctt gtg tta ctc aat gca gcg<br>Ser Gln Ala Glu Ala Ala Leu Glu Asn Leu Val Leu Leu Asn Ala Ala<br>                745                    750                    755 | 2612 |
| tct ctg gcc ggg acg cac ggt ctt gcg tcc ttc ctc gtg ttc ttc tgc<br>Ser Leu Ala Gly Thr His Gly Leu Ala Ser Phe Leu Val Phe Phe Cys<br>            760                    765                    770 | 2660 |
| ttt gca tgg tat ctg aag ggt agg tgg gtg ccc gga gtg gcc tac gcc<br>Phe Ala Trp Tyr Leu Lys Gly Arg Trp Val Pro Gly Val Ala Tyr Ala<br>775                    780                    785 | 2708 |
| ttc tac ggg atg tgg cct ctc ctg ctc ctg ttg gcg ttg ccc cag<br>Phe Tyr Gly Met Trp Pro Leu Leu Leu Leu Leu Ala Leu Pro Gln<br>790                    795                  800                  805 | 2756 |
| cgg gca tac gcg ctg gac acg gag atg gcc gcg tcg tgt ggc ggc gtt<br>Arg Ala Tyr Ala Leu Asp Thr Glu Met Ala Ala Ser Cys Gly Gly Val<br>                    810                    815                    820 | 2804 |
| gtt ctt gtc ggg ttg atg gcg cta act ctg tca ccg tac tac aag agc<br>Val Leu Val Gly Leu Met Ala Leu Thr Leu Ser Pro Tyr Tyr Lys Ser<br>                825                    830                    835 | 2852 |
| tat atc agc tgg tgc tta tgg tgg ctt cag tac ttc cta act agg ata<br>Tyr Ile Ser Trp Cys Leu Trp Trp Leu Gln Tyr Phe Leu Thr Arg Ile<br>            840                    845                    850 | 2900 |
| gaa gcg cta ctg cac gtg tgg gtc ccc ccc ctc aat gtc cga gga ggg<br>Glu Ala Leu Leu His Val Trp Val Pro Pro Leu Asn Val Arg Gly Gly<br>855                    860                    865 | 2948 |
| cgc gac gct gtc atc ctg ctc acg tgt gtt gta cac ccg acc ttg gta<br>Arg Asp Ala Val Ile Leu Leu Thr Cys Val Val His Pro Thr Leu Val<br>870                    875                    880                    885 | 2996 |
| ttc gac atc acc aag cta cta ctg gcc gtc ttc gga ccc ctt tgg att<br>Phe Asp Ile Thr Lys Leu Leu Leu Ala Val Phe Gly Pro Leu Trp Ile<br>                    890                    895                    900 | 3044 |
| ctc caa acc agt ctg ctc aag gtg ccc tac ttc gtg cgc gtc caa ggc<br>Leu Gln Thr Ser Leu Leu Lys Val Pro Tyr Phe Val Arg Val Gln Gly<br>                905                    910                    915 | 3092 |
| ctt ctc cgg gcc tgc gcg cta gcg cgt aag gtg gcc gga ggc cat tac<br>Leu Leu Arg Ala Cys Ala Leu Ala Arg Lys Val Ala Gly Gly His Tyr<br>            920                    925                    930 | 3140 |
| gtg cag atg gtc atc atc aag ttg ggg gcg ctt act ggc acc tac atc<br>Val Gln Met Val Ile Ile Lys Leu Gly Ala Leu Thr Gly Thr Tyr Ile<br>935                    940                    945 | 3188 |
| tac aac cat ctc act cct ctc cgg gac tgg gcg cac aac ggc cta cga<br>Tyr Asn His Leu Thr Pro Leu Arg Asp Trp Ala His Asn Gly Leu Arg<br>950                    955                    960                    965 | 3236 |
| gat ctg gcc gtg gct gta gag cca gtc gtc ttt tcc cag atg gag acc | 3284 |

```
                    Asp Leu Ala Val Ala Val Glu Pro Val Val Phe Ser Gln Met Glu Thr
                                    970                 975                 980 aag ctc atc acg tgg ggg gcg gac acc gcc gcg tgc ggt gac atc atc              3332
Lys Leu Ile Thr Trp Gly Ala Asp Thr Ala Ala Cys Gly Asp Ile Ile
            985                 990                 995 aac ggc ctg cct gtc tct gcc cgt agg ggc caa gag ata ttg ctc                  3377
Asn Gly Leu Pro Val Ser Ala Arg Arg Gly Gln Glu Ile Leu Leu
        1000                1005                1010 gga ccg gcc gat gga atg gtc tct aag ggg tgg agg ttg ctg gcg                  3422
Gly Pro Ala Asp Gly Met Val Ser Lys Gly Trp Arg Leu Leu Ala
        1015                1020                1025 ccc atc acg gcg tat gcc cag cag aca agg ggc ctc ctg gga tgc                  3467
Pro Ile Thr Ala Tyr Ala Gln Gln Thr Arg Gly Leu Leu Gly Cys
        1030                1035                1040 ata att act agc ctg acc ggc cgg gac aaa aac cag gtg gag ggt                  3512
Ile Ile Thr Ser Leu Thr Gly Arg Asp Lys Asn Gln Val Glu Gly
        1045                1050                1055 gag gtc cag att gtg tca act gct gcc cag acc ttc ctg gca acc                  3557
Glu Val Gln Ile Val Ser Thr Ala Ala Gln Thr Phe Leu Ala Thr
        1060                1065                1070 tgc atc aac gga gtg tgc tgg act gtc tac cac ggg gcc gga aca                  3602
Cys Ile Asn Gly Val Cys Trp Thr Val Tyr His Gly Ala Gly Thr
        1075                1080                1085 agg acc atc gcg tca ccc aaa ggt ccc gtc atc cag atg tat act                  3647
Arg Thr Ile Ala Ser Pro Lys Gly Pro Val Ile Gln Met Tyr Thr
        1090                1095                1100 aat gta gac caa gac ctt gta ggc tgg ccc gct ccc caa ggt gcc                  3692
Asn Val Asp Gln Asp Leu Val Gly Trp Pro Ala Pro Gln Gly Ala
        1105                1110                1115 cgc tca ttg aca ccc tgc act tgc ggc tcc tcg gac ctt tac ttg                  3737
Arg Ser Leu Thr Pro Cys Thr Cys Gly Ser Ser Asp Leu Tyr Leu
        1120                1125                1130 gtc acg agg cac gcc gat gtc att ccc gtg cgc cgg cgg ggt gat                  3782
Val Thr Arg His Ala Asp Val Ile Pro Val Arg Arg Arg Gly Asp
        1135                1140                1145 agc agg ggc agc ctg ctc tcg ccc cgg cct atc tct tac ttg aaa                  3827
Ser Arg Gly Ser Leu Leu Ser Pro Arg Pro Ile Ser Tyr Leu Lys
        1150                1155                1160 ggc tct tcg ggg ggc cca ttg ctg tgc ccc gcg gga cac gcc gta                  3872
Gly Ser Ser Gly Gly Pro Leu Leu Cys Pro Ala Gly His Ala Val
        1165                1170                1175 ggc ata ttc agg gcc gcg gtg tgc acc cgt gga gtg gct aag gcg                  3917
Gly Ile Phe Arg Ala Ala Val Cys Thr Arg Gly Val Ala Lys Ala
        1180                1185                1190 gtg gac ttt atc ccc gta gag agt cta gag aca acc atg agg tcc                  3962
Val Asp Phe Ile Pro Val Glu Ser Leu Glu Thr Thr Met Arg Ser
        1195                1200                1205 ccg gtg ttc aca gac aac tcc tcc cca cca gca gtg ccc cag agc                  4007
Pro Val Phe Thr Asp Asn Ser Ser Pro Pro Ala Val Pro Gln Ser
        1210                1215                1220 ttc cag gtg gcc cac ctg cat gct ccc acc ggc agc ggt aag agt                  4052
Phe Gln Val Ala His Leu His Ala Pro Thr Gly Ser Gly Lys Ser
        1225                1230                1235 acc aag gtc ccg gcc gca tac gcg gct cag ggc tac aag gtg ctg                  4097
Thr Lys Val Pro Ala Ala Tyr Ala Ala Gln Gly Tyr Lys Val Leu
        1240                1245                1250 gtg ctc aac ccc tcc gtt gct gca aca ctg ggc ttt ggt gct tat                  4142
Val Leu Asn Pro Ser Val Ala Ala Thr Leu Gly Phe Gly Ala Tyr
        1255                1260                1265 atg tcc aag gcc cat ggg att gat cct aac atc agg act ggg gtg                  4187
```

```
Met Ser Lys Ala His Gly Ile Asp Pro Asn Ile Arg Thr Gly Val
        1270                1275                1280 agg aca atc act act ggc agc ccc atc acg tac tcc acc tac ggc         4232
Arg Thr Ile Thr Thr Gly Ser Pro Ile Thr Tyr Ser Thr Tyr Gly
        1285                1290                1295 aag ttc ctt gct gat ggc ggg tgc tcg ggg ggt gct tat gac ata         4277
Lys Phe Leu Ala Asp Gly Gly Cys Ser Gly Gly Ala Tyr Asp Ile
        1300                1305                1310 ata att tgt gac gag tgc cac tct acg gat gca aca tcc gtc ttg         4322
Ile Ile Cys Asp Glu Cys His Ser Thr Asp Ala Thr Ser Val Leu
        1315                1320                1325 ggc atc ggc act gtc ctt gac caa gca gag act gcg ggg gcg aga         4367
Gly Ile Gly Thr Val Leu Asp Gln Ala Glu Thr Ala Gly Ala Arg
        1330                1335                1340 ctg gtc gtg ctc gcc acc gct acc cct ccg ggc tct gtc act gtg         4412
Leu Val Val Leu Ala Thr Ala Thr Pro Pro Gly Ser Val Thr Val
        1345                1350                1355 ccc cat cct aac atc gag gag gtt gct ctg tcc acc acc gga gag         4457
Pro His Pro Asn Ile Glu Glu Val Ala Leu Ser Thr Thr Gly Glu
        1360                1365                1370 atc ccc ttt tac ggc aag gct atc ccc ctt gag gca atc aag ggg         4502
Ile Pro Phe Tyr Gly Lys Ala Ile Pro Leu Glu Ala Ile Lys Gly
        1375                1380                1385 ggg aga cat ctc atc ttc tgc cat tca aaa aag aag tgc gac gag         4547
Gly Arg His Leu Ile Phe Cys His Ser Lys Lys Lys Cys Asp Glu
        1390                1395                1400 ctc gct gca aag ctg gtc gcg atg ggc gtc aat gcc gtg gct tac         4592
Leu Ala Ala Lys Leu Val Ala Met Gly Val Asn Ala Val Ala Tyr
        1405                1410                1415 tac cgc ggc ctc gac gtg tcc gtc atc cca acc agt ggc gat gtt         4637
Tyr Arg Gly Leu Asp Val Ser Val Ile Pro Thr Ser Gly Asp Val
        1420                1425                1430 gtc gtc gtg gca act gat gcc ctc atg acc ggc tat acc ggc gac         4682
Val Val Val Ala Thr Asp Ala Leu Met Thr Gly Tyr Thr Gly Asp
        1435                1440                1445 ttt gac tcg gtg ata gac tgc aac acg tgt gtc acc cag aca gtc         4727
Phe Asp Ser Val Ile Asp Cys Asn Thr Cys Val Thr Gln Thr Val
        1450                1455                1460 gac ttc agc ctt gac cct acc ttc acc att gag aca acc acg ctc         4772
Asp Phe Ser Leu Asp Pro Thr Phe Thr Ile Glu Thr Thr Thr Leu
        1465                1470                1475 ccc cag gac gct gtc tcc cgc act caa cgt cgg ggc agg act ggc         4817
Pro Gln Asp Ala Val Ser Arg Thr Gln Arg Arg Gly Arg Thr Gly
        1480                1485                1490 agg ggg aag cca ggc atc tac aga ttt gtg gca ccg ggg gag cgc         4862
Arg Gly Lys Pro Gly Ile Tyr Arg Phe Val Ala Pro Gly Glu Arg
        1495                1500                1505 ccc tcc ggc atg ttt gac tcg tcc gtc ctc tgt gag tgc tat gac         4907
Pro Ser Gly Met Phe Asp Ser Ser Val Leu Cys Glu Cys Tyr Asp
        1510                1515                1520 gcg ggc tgt gct tgg tat gag ctc aca ccc gcc gag acc aca gtt         4952
Ala Gly Cys Ala Trp Tyr Glu Leu Thr Pro Ala Glu Thr Thr Val
        1525                1530                1535 agg cta cga gca tat atg aac acc ccg ggg ctc ccc gtg tgc caa         4997
Arg Leu Arg Ala Tyr Met Asn Thr Pro Gly Leu Pro Val Cys Gln
        1540                1545                1550 gac cat ctt gaa ttt tgg gag ggc gtc ttc acg ggt ctc acc cat         5042
Asp His Leu Glu Phe Trp Glu Gly Val Phe Thr Gly Leu Thr His
        1555                1560                1565 ata gac gcc cat ttc cta tcc cag aca aag cag agt ggg gaa aac         5087
```

-continued

| | | | | | | | | | | | | |
|---|---|---|---|---|---|---|---|---|---|---|---|---|
| Ile | Asp | Ala | His | Phe | Leu | Ser | Gln | Thr | Lys | Gln | Ser | Gly | Glu | Asn |
| | | 1570 | | | 1575 | | | | 1580 | | | |

```
ctt cct tac ctg gta gcg tac caa gcc acc gtg tgc gct agg gct    5132
Leu Pro Tyr Leu Val Ala Tyr Gln Ala Thr Val Cys Ala Arg Ala
        1585            1590            1595 cag gcc ccc ccc cca tcg tgg gac cag atg tgg aag tgc ttg atc    5177
Gln Ala Pro Pro Pro Ser Trp Asp Gln Met Trp Lys Cys Leu Ile
1600            1605            1610 cgc ctc aag ccc acc ctt cat ggg cca aca cct ctg cta tac aga    5222
Arg Leu Lys Pro Thr Leu His Gly Pro Thr Pro Leu Leu Tyr Arg
        1615            1620            1625 ctg ggc gct gtt cag aat gaa gtc acc ctg acg cac cca atc acc    5267
Leu Gly Ala Val Gln Asn Glu Val Thr Leu Thr His Pro Ile Thr
1630            1635            1640 aag tac atc atg aca tgc atg tcg gct gac ctg gag gtc gtc acg    5312
Lys Tyr Ile Met Thr Cys Met Ser Ala Asp Leu Glu Val Val Thr
        1645            1650            1655 agt acc tgg gtg ctc gtc ggc ggc gtc ctg gct gct ttg gcc gcg    5357
Ser Thr Trp Val Leu Val Gly Gly Val Leu Ala Ala Leu Ala Ala
1660            1665            1670 tat tgc cta tcc aca ggc tgc gtg gtc ata gta ggc agg att gtc    5402
Tyr Cys Leu Ser Thr Gly Cys Val Val Ile Val Gly Arg Ile Val
        1675            1680            1685 ttg tcc ggg aag ccg gct atc ata cct gac agg gaa gtc ctc tac    5447
Leu Ser Gly Lys Pro Ala Ile Ile Pro Asp Arg Glu Val Leu Tyr
1690            1695            1700 cgg gag ttc gat gag atg gaa gag tgc tct cag cac ttg ccg tac    5492
Arg Glu Phe Asp Glu Met Glu Glu Cys Ser Gln His Leu Pro Tyr
        1705            1710            1715 atc gag cag ggg atg atg ctc gcc gag cag ttc aag cag aag gcc    5537
Ile Glu Gln Gly Met Met Leu Ala Glu Gln Phe Lys Gln Lys Ala
1720            1725            1730 ctc ggc ctc ctg cag acc gcg tcc cgc cag gca gag gtc atc gcc    5582
Leu Gly Leu Leu Gln Thr Ala Ser Arg Gln Ala Glu Val Ile Ala
        1735            1740            1745 cct acc gtc caa acc aac tgg cag aga ctc gag gcc ttc tgg gcg    5627
Pro Thr Val Gln Thr Asn Trp Gln Arg Leu Glu Ala Phe Trp Ala
1750            1755            1760 aag cat atg tgg aac ttc atc agt ggg ata caa tat ctg gcg ggc    5672
Lys His Met Trp Asn Phe Ile Ser Gly Ile Gln Tyr Leu Ala Gly
        1765            1770            1775 ctg tca acg ttg cct ggt aat ccc gcc att gca tca ttg atg gct    5717
Leu Ser Thr Leu Pro Gly Asn Pro Ala Ile Ala Ser Leu Met Ala
1780            1785            1790 ttt aca gct gcc gtc acc agc cca cta acc acc ggc caa act ctc    5762
Phe Thr Ala Ala Val Thr Ser Pro Leu Thr Thr Gly Gln Thr Leu
        1795            1800            1805 ctc ttc aac att ttg ggg ggg tgg gtg gct gcc cag ctc gca gcc    5807
Leu Phe Asn Ile Leu Gly Gly Trp Val Ala Ala Gln Leu Ala Ala
1810            1815            1820 ccc ggt gcc gct acc gcc ttt gtg ggc gct ggc tta gcc ggc gcc    5852
Pro Gly Ala Ala Thr Ala Phe Val Gly Ala Gly Leu Ala Gly Ala
        1825            1830            1835 gcc atc ggc agt gtt gga ctg ggg aag gtc ctc gtg gac atc ctt    5897
Ala Ile Gly Ser Val Gly Leu Gly Lys Val Leu Val Asp Ile Leu
1840            1845            1850 gca ggg tat ggc gcg ggc gtg gcg gga gct ctt gta gca ttt aag    5942
Ala Gly Tyr Gly Ala Gly Val Ala Gly Ala Leu Val Ala Phe Lys
        1855            1860            1865 atc atg agc ggt gag gtt ccc tcc aca gag gac ctg gtc aat cta    5987
```

| | | | | | | | | | | | | |
|---|---|---|---|---|---|---|---|---|---|---|---|---|
| Ile | Met | Ser | Gly | Glu | Val | Pro | Ser | Thr | Glu | Asp | Leu | Val | Asn | Leu |
| | | 1870 | | | | 1875 | | | | 1880 | | |

| ctg | cct | gcc | atc | ctt | tcg | ccc | gga | gcc | ctt | gta | gtc | ggt | gtg | gtc | 6032 |
|---|---|---|---|---|---|---|---|---|---|---|---|---|---|---|---|
| Leu | Pro | Ala | Ile | Leu | Ser | Pro | Gly | Ala | Leu | Val | Val | Gly | Val | Val | |
| | | 1885 | | | | 1890 | | | | 1895 | | | | | |

| tgc | gca | gca | ata | cta | cgc | cgg | cac | gtt | ggc | ccg | ggc | gag | gga | gca | 6077 |
|---|---|---|---|---|---|---|---|---|---|---|---|---|---|---|---|
| Cys | Ala | Ala | Ile | Leu | Arg | Arg | His | Val | Gly | Pro | Gly | Glu | Gly | Ala | |
| | | 1900 | | | | 1905 | | | | 1910 | | | | | |

| gtg | cag | tgg | atg | aac | cgg | ttg | ata | gcc | ttc | gcc | tcc | cgg | ggg | aac | 6122 |
|---|---|---|---|---|---|---|---|---|---|---|---|---|---|---|---|
| Val | Gln | Trp | Met | Asn | Arg | Leu | Ile | Ala | Phe | Ala | Ser | Arg | Gly | Asn | |
| | | 1915 | | | | 1920 | | | | 1925 | | | | | |

| cac | gtt | tcc | ccc | acg | cac | tac | gtg | ccg | gag | agc | gat | gca | gct | gcc | 6167 |
|---|---|---|---|---|---|---|---|---|---|---|---|---|---|---|---|
| His | Val | Ser | Pro | Thr | His | Tyr | Val | Pro | Glu | Ser | Asp | Ala | Ala | Ala | |
| | | 1930 | | | | 1935 | | | | 1940 | | | | | |

| cgc | gtc | act | gcc | ata | ctc | agc | agc | ctc | act | gtg | acc | cag | ctc | ctg | 6212 |
|---|---|---|---|---|---|---|---|---|---|---|---|---|---|---|---|
| Arg | Val | Thr | Ala | Ile | Leu | Ser | Ser | Leu | Thr | Val | Thr | Gln | Leu | Leu | |
| | | 1945 | | | | 1950 | | | | 1955 | | | | | |

| agg | cga | cta | cac | cag | tgg | cta | agc | tcg | gag | tgt | acc | act | cca | tgc | 6257 |
|---|---|---|---|---|---|---|---|---|---|---|---|---|---|---|---|
| Arg | Arg | Leu | His | Gln | Trp | Leu | Ser | Ser | Glu | Cys | Thr | Thr | Pro | Cys | |
| | | 1960 | | | | 1965 | | | | 1970 | | | | | |

| tcc | ggt | tcc | tgg | cta | agg | gac | atc | tgg | gac | tgg | ata | tgc | gag | gtg | 6302 |
|---|---|---|---|---|---|---|---|---|---|---|---|---|---|---|---|
| Ser | Gly | Ser | Trp | Leu | Arg | Asp | Ile | Trp | Asp | Trp | Ile | Cys | Glu | Val | |
| | | 1975 | | | | 1980 | | | | 1985 | | | | | |

| ctg | agc | gat | ttt | aag | acc | tgg | ctg | aag | gcc | aag | ctc | atg | cca | caa | 6347 |
|---|---|---|---|---|---|---|---|---|---|---|---|---|---|---|---|
| Leu | Ser | Asp | Phe | Lys | Thr | Trp | Leu | Lys | Ala | Lys | Leu | Met | Pro | Gln | |
| | | 1990 | | | | 1995 | | | | 2000 | | | | | |

| ctg | cct | ggg | att | ccc | ttt | gtg | tcc | tgc | caa | cgc | ggg | tac | agg | ggg | 6392 |
|---|---|---|---|---|---|---|---|---|---|---|---|---|---|---|---|
| Leu | Pro | Gly | Ile | Pro | Phe | Val | Ser | Cys | Gln | Arg | Gly | Tyr | Arg | Gly | |
| | | 2005 | | | | 2010 | | | | 2015 | | | | | |

| gtc | tgg | cga | gga | gat | ggc | att | atg | cac | act | cgc | tgc | ccc | tgt | gga | 6437 |
|---|---|---|---|---|---|---|---|---|---|---|---|---|---|---|---|
| Val | Trp | Arg | Gly | Asp | Gly | Ile | Met | His | Thr | Arg | Cys | Pro | Cys | Gly | |
| | | 2020 | | | | 2025 | | | | 2030 | | | | | |

| gct | gag | atc | gcc | gga | cat | gtc | aag | aac | ggg | acg | atg | agg | atc | gtc | 6482 |
|---|---|---|---|---|---|---|---|---|---|---|---|---|---|---|---|
| Ala | Glu | Ile | Ala | Gly | His | Val | Lys | Asn | Gly | Thr | Met | Arg | Ile | Val | |
| | | 2035 | | | | 2040 | | | | 2045 | | | | | |

| ggt | cct | aag | acc | tgc | aga | aac | acg | tgg | agt | ggg | acc | ttc | ccc | atc | 6527 |
|---|---|---|---|---|---|---|---|---|---|---|---|---|---|---|---|
| Gly | Pro | Lys | Thr | Cys | Arg | Asn | Thr | Trp | Ser | Gly | Thr | Phe | Pro | Ile | |
| | | 2050 | | | | 2055 | | | | 2060 | | | | | |

| aac | gcc | tac | acc | acg | ggc | ccc | tgt | acc | ccc | ctt | cct | gcg | ccg | aac | 6572 |
|---|---|---|---|---|---|---|---|---|---|---|---|---|---|---|---|
| Asn | Ala | Tyr | Thr | Thr | Gly | Pro | Cys | Thr | Pro | Leu | Pro | Ala | Pro | Asn | |
| | | 2065 | | | | 2070 | | | | 2075 | | | | | |

| tat | acg | ttc | gcg | ctg | tgg | agg | gtg | tct | gcg | gag | gaa | tac | gtg | gaa | 6617 |
|---|---|---|---|---|---|---|---|---|---|---|---|---|---|---|---|
| Tyr | Thr | Phe | Ala | Leu | Trp | Arg | Val | Ser | Ala | Glu | Glu | Tyr | Val | Glu | |
| | | 2080 | | | | 2085 | | | | 2090 | | | | | |

| ata | agg | cag | gtg | ggg | gac | ttc | cac | tac | gtg | acg | ggc | atg | act | gct | 6662 |
|---|---|---|---|---|---|---|---|---|---|---|---|---|---|---|---|
| Ile | Arg | Gln | Val | Gly | Asp | Phe | His | Tyr | Val | Thr | Gly | Met | Thr | Ala | |
| | | 2095 | | | | 2100 | | | | 2105 | | | | | |

| gac | aac | ctt | aag | tgc | cca | tgc | cag | gtc | cca | tcg | ccc | gaa | ttt | ttc | 6707 |
|---|---|---|---|---|---|---|---|---|---|---|---|---|---|---|---|
| Asp | Asn | Leu | Lys | Cys | Pro | Cys | Gln | Val | Pro | Ser | Pro | Glu | Phe | Phe | |
| | | 2110 | | | | 2115 | | | | 2120 | | | | | |

| aca | gaa | ctg | gat | ggg | gtg | cgc | ctg | cat | agg | ttt | gcg | ccc | cct | tgc | 6752 |
|---|---|---|---|---|---|---|---|---|---|---|---|---|---|---|---|
| Thr | Glu | Leu | Asp | Gly | Val | Arg | Leu | His | Arg | Phe | Ala | Pro | Pro | Cys | |
| | | 2125 | | | | 2130 | | | | 2135 | | | | | |

| aag | ccc | ttg | cta | cga | gat | gag | gtg | tcg | ttc | aga | gta | gga | cta | cac | 6797 |
|---|---|---|---|---|---|---|---|---|---|---|---|---|---|---|---|
| Lys | Pro | Leu | Leu | Arg | Asp | Glu | Val | Ser | Phe | Arg | Val | Gly | Leu | His | |
| | | 2140 | | | | 2145 | | | | 2150 | | | | | |

| gac | tac | ccg | gtg | ggg | tcg | cag | tta | cct | tgc | gag | cct | gaa | ccg | gat | 6842 |
|---|---|---|---|---|---|---|---|---|---|---|---|---|---|---|---|
| Asp | Tyr | Pro | Val | Gly | Ser | Gln | Leu | Pro | Cys | Glu | Pro | Glu | Pro | Asp | |
| | | 2155 | | | | 2160 | | | | 2165 | | | | | |

| gtg | gcc | gta | ctg | acg | tcc | atg | ctc | acc | gat | ccc | tcc | cat | ata | acg | 6887 |
|---|---|---|---|---|---|---|---|---|---|---|---|---|---|---|---|

```
                    Val Ala Val Leu Thr Ser Met Leu Thr Asp Pro Ser His Ile Thr
                            2170                2175                2180 gca gag gcg gct ggg agg agg tta gca agg gga tcg ccc cct tct          6932
Ala Glu Ala Ala Gly Arg Arg Leu Ala Arg Gly Ser Pro Pro Ser
        2185                2190                2195 ctg gcc agc tcc tcg gcc agc cag ctg tcc gct cca tct ctc aaa          6977
Leu Ala Ser Ser Ser Ala Ser Gln Leu Ser Ala Pro Ser Leu Lys
        2200                2205                2210 gca act tgc acc acc aac cac gac tcc cct gac gcc gag ctc ata          7022
Ala Thr Cys Thr Thr Asn His Asp Ser Pro Asp Ala Glu Leu Ile
        2215                2220                2225 gag gct aac ctc ctg tgg agg cag gag atg ggc ggc aac atc acc          7067
Glu Ala Asn Leu Leu Trp Arg Gln Glu Met Gly Gly Asn Ile Thr
        2230                2235                2240 agg gtt gag tca gag aac aaa gtg gta gtc ctg gac tcc ttc gat          7112
Arg Val Glu Ser Glu Asn Lys Val Val Val Leu Asp Ser Phe Asp
        2245                2250                2255 ccg ctt gtg gca gaa gag gac gaa cgg gag atc tcc gtg gcc gca          7157
Pro Leu Val Ala Glu Glu Asp Glu Arg Glu Ile Ser Val Ala Ala
        2260                2265                2270 gag atc ctg cgg aag tct cgg aga ttc gct ccg gcc ctg ccc att          7202
Glu Ile Leu Arg Lys Ser Arg Arg Phe Ala Pro Ala Leu Pro Ile
        2275                2280                2285 tgg gca cgg ccg gac tac aac ccc ccg tta ctg gag acg tgg aaa          7247
Trp Ala Arg Pro Asp Tyr Asn Pro Pro Leu Leu Glu Thr Trp Lys
        2290                2295                2300 aag ccg gac tac gag cca cct gtg gtc cat ggc tgc ccg ctt cca          7292
Lys Pro Asp Tyr Glu Pro Pro Val Val His Gly Cys Pro Leu Pro
        2305                2310                2315 cct cca aag tcc cct cct gtg cct ccg ccc cgg aag aag cgg acg          7337
Pro Pro Lys Ser Pro Pro Val Pro Pro Pro Arg Lys Lys Arg Thr
        2320                2325                2330 gtg gtc ctc act gaa tca act gta tcc act gcc ttg gct gag ctt          7382
Val Val Leu Thr Glu Ser Thr Val Ser Thr Ala Leu Ala Glu Leu
        2335                2340                2345 gct acc aag agc ttt ggc agc tct tca act tcc ggt ata acg ggc          7427
Ala Thr Lys Ser Phe Gly Ser Ser Ser Thr Ser Gly Ile Thr Gly
        2350                2355                2360 gac aac acg aca gcg tcc tct gag ccc gcc ccc tct gtc tgc cct          7472
Asp Asn Thr Thr Ala Ser Ser Glu Pro Ala Pro Ser Val Cys Pro
        2365                2370                2375 cca gac tcc gac gct gag tcc tat tct tcc atg ccc ccc ctg gag          7517
Pro Asp Ser Asp Ala Glu Ser Tyr Ser Ser Met Pro Pro Leu Glu
        2380                2385                2390 ggg gag cct ggg gat ccg gat ctc agc gac ggg tca tgg tcg acg          7562
Gly Glu Pro Gly Asp Pro Asp Leu Ser Asp Gly Ser Trp Ser Thr
        2395                2400                2405 gtc agt agt ggg gct ggc acg gag gat gtc gtg tgt tca atg          7607
Val Ser Ser Gly Ala Gly Thr Glu Asp Val Val Cys Cys Ser Met
        2410                2415                2420 tcc tat tcc tgg aca ggc gca ctc atc acc ccg tgt gcc gcg gaa          7652
Ser Tyr Ser Trp Thr Gly Ala Leu Ile Thr Pro Cys Ala Ala Glu
        2425                2430                2435 gaa caa aaa ttg cct atc aac gca ctg agc aac tca tta ctg cgt          7697
Glu Gln Lys Leu Pro Ile Asn Ala Leu Ser Asn Ser Leu Leu Arg
        2440                2445                2450 cac cac aac ctc gtg tat tcc acc acc tca cgc agt gct tgc caa          7742
His His Asn Leu Val Tyr Ser Thr Thr Ser Arg Ser Ala Cys Gln
        2455                2460                2465 agg cag aag aaa gtc aca ttt gac aga ctg caa gtt ctg gac aac          7787
```

```
Arg Gln Lys Lys Val Thr Phe Asp Arg Leu Gln Val Leu Asp Asn
        2470            2475            2480 cac tac cag gac gtg ctc aag gag gtt aag gcg gcg gcg tca aaa      7832
His Tyr Gln Asp Val Leu Lys Glu Val Lys Ala Ala Ala Ser Lys
        2485            2490            2495 gtg aag gct aac ttg cta tcc gta gag gaa gct tgc agc ctg acg      7877
Val Lys Ala Asn Leu Leu Ser Val Glu Glu Ala Cys Ser Leu Thr
        2500            2505            2510 ccc cca cat tca gcc aga tca aaa ttt ggc tat ggg gca aaa gac      7922
Pro Pro His Ser Ala Arg Ser Lys Phe Gly Tyr Gly Ala Lys Asp
        2515            2520            2525 gtc cgt tgc cat gcc aga aag gcc gta aac cac atc aac tcc gtg      7967
Val Arg Cys His Ala Arg Lys Ala Val Asn His Ile Asn Ser Val
        2530            2535            2540 tgg aaa gac ctt ctg gaa gac agt gtt aca cca ata gac aca acc      8012
Trp Lys Asp Leu Leu Glu Asp Ser Val Thr Pro Ile Asp Thr Thr
        2545            2550            2555 atc atg gct aag aac gaa gtt ttc tgc gtt cag cct gag aag ggg      8057
Ile Met Ala Lys Asn Glu Val Phe Cys Val Gln Pro Glu Lys Gly
        2560            2565            2570 ggt cgt aag cca gct cgt ctc atc gtg tac cct gac ctg ggt gtg      8102
Gly Arg Lys Pro Ala Arg Leu Ile Val Tyr Pro Asp Leu Gly Val
        2575            2580            2585 cgc gtg tgc gag aaa atg gcc ctg tac gac gtg gta aaa aaa ctg      8147
Arg Val Cys Glu Lys Met Ala Leu Tyr Asp Val Val Lys Lys Leu
        2590            2595            2600 ccc ctg gcc gtg atg gga agc tcc tac gga ttc cag tac tca cca      8192
Pro Leu Ala Val Met Gly Ser Ser Tyr Gly Phe Gln Tyr Ser Pro
        2605            2610            2615 gga cag cgg gtt gaa ttc ctc gtg caa gcg tgg aag tcc aag ggg      8237
Gly Gln Arg Val Glu Phe Leu Val Gln Ala Trp Lys Ser Lys Gly
        2620            2625            2630 acc cca atg ggg ttc tcg tat gat acc cgc tgc ttt gac tct aca      8282
Thr Pro Met Gly Phe Ser Tyr Asp Thr Arg Cys Phe Asp Ser Thr
        2635            2640            2645 gtc act gag agc gat atc cgt acg gag gag gca atc tac cag tgt      8327
Val Thr Glu Ser Asp Ile Arg Thr Glu Glu Ala Ile Tyr Gln Cys
        2650            2655            2660 tgt gac ctg gac ccc caa gcc cgc gtg gcc atc aag tcc ctc acc      8372
Cys Asp Leu Asp Pro Gln Ala Arg Val Ala Ile Lys Ser Leu Thr
        2665            2670            2675 gag agg ctt tat gtc ggg ggt cct ctt acc aat tca agg ggg gaa      8417
Glu Arg Leu Tyr Val Gly Gly Pro Leu Thr Asn Ser Arg Gly Glu
        2680            2685            2690 aac tgc ggc tat cgc agg tgc cgc gca agc ggc gta ctg aca act      8462
Asn Cys Gly Tyr Arg Arg Cys Arg Ala Ser Gly Val Leu Thr Thr
        2695            2700            2705 agc tgt ggt aac acc ctc act tgc tac atc aag gcc cga gca gcc      8507
Ser Cys Gly Asn Thr Leu Thr Cys Tyr Ile Lys Ala Arg Ala Ala
        2710            2715            2720 tgt cga gcc gca ggg ctc cgg gac tgc acc atg ctc gtg tgt ggc      8552
Cys Arg Ala Ala Gly Leu Arg Asp Cys Thr Met Leu Val Cys Gly
        2725            2730            2735 gac gac tta gtc gtt atc tgt gaa agc cag ggg gtc caa gag gat      8597
Asp Asp Leu Val Val Ile Cys Glu Ser Gln Gly Val Gln Glu Asp
        2740            2745            2750 aca gcg agc ctg aga gcc ttc acg gag gct atg acc agg tac tcc      8642
Thr Ala Ser Leu Arg Ala Phe Thr Glu Ala Met Thr Arg Tyr Ser
        2755            2760            2765 gct ccc ccc ggg gac ccc ccc caa cca gaa tac gac ttg gag ctc      8687
```

```
                Ala Pro Pro Gly Asp Pro Pro Gln Pro Glu Tyr Asp Leu Glu Leu
                        2770            2775            2780 ata aca tcg tgc tcc tct aac gtg tca gtc gcc cac gac gac act             8732
Ile Thr Ser Cys Ser Ser Asn Val Ser Val Ala His Asp Asp Thr
            2785            2790            2795 gga aag agg gtc tat tac ctt acc cgt gac cct aca act ccc ctc             8777
Gly Lys Arg Val Tyr Tyr Leu Thr Arg Asp Pro Thr Thr Pro Leu
            2800            2805            2810 gcg aga gcc gcg tgg gag aca gca aga cac act cca gtc aat tcc             8822
Ala Arg Ala Ala Trp Glu Thr Ala Arg His Thr Pro Val Asn Ser
            2815            2820            2825 tgg cta ggc aac ata atc atg ttt gcc ccc aca ttg tgg gtg aga             8867
Trp Leu Gly Asn Ile Ile Met Phe Ala Pro Thr Leu Trp Val Arg
            2830            2835            2840 atg ata ctg ctg ccc cac ttc ttc agt gtc ctc atg gcc agg gac             8912
Met Ile Leu Leu Pro His Phe Phe Ser Val Leu Met Ala Arg Asp
            2845            2850            2855 caa ctt gaa cag gcc ctt gat tgc gaa atc tac gga gcc tgc tac             8957
Gln Leu Glu Gln Ala Leu Asp Cys Glu Ile Tyr Gly Ala Cys Tyr
            2860            2865            2870 tcc ata gaa cca ctg gac cta cct cca atc att caa aga ctc cat             9002
Ser Ile Glu Pro Leu Asp Leu Pro Pro Ile Ile Gln Arg Leu His
            2875            2880            2885 ggc ctt agc gca ttt tca ctc cac agt tac tct cca ggt gaa atc             9047
Gly Leu Ser Ala Phe Ser Leu His Ser Tyr Ser Pro Gly Glu Ile
            2890            2895            2900 aat agg gtg gcc gca tgc ctc aga aaa ctt ggg gtc ccg ccc ttg             9092
Asn Arg Val Ala Ala Cys Leu Arg Lys Leu Gly Val Pro Pro Leu
            2905            2910            2915 cga gct tgg aga cac cgg gcc cgg agc atc cgc gct aag ctt ctg             9137
Arg Ala Trp Arg His Arg Ala Arg Ser Ile Arg Ala Lys Leu Leu
            2920            2925            2930 tcc aga gga ggc agg gct gcc acg tgt ggc aag tac ctc ttc aat             9182
Ser Arg Gly Gly Arg Ala Ala Thr Cys Gly Lys Tyr Leu Phe Asn
            2935            2940            2945 tgg gca gta aga aca aag ctc aaa ctc act cca ata gcg gcc gct             9227
Trp Ala Val Arg Thr Lys Leu Lys Leu Thr Pro Ile Ala Ala Ala
            2950            2955            2960 agc cag ctg gac ttg tcc ggt tgg ttc acg gct ggc tac agc ggg             9272
Ser Gln Leu Asp Leu Ser Gly Trp Phe Thr Ala Gly Tyr Ser Gly
            2965            2970            2975 gga gac att tat cac agc gtg tct cgt gcc cgg ccc cgc tgg ttc             9317
Gly Asp Ile Tyr His Ser Val Ser Arg Ala Arg Pro Arg Trp Phe
            2980            2985            2990 tgg ttt tgc cta ctc ctg ctt gct gca ggg gta ggc atc tac ctc             9362
Trp Phe Cys Leu Leu Leu Leu Ala Ala Gly Val Gly Ile Tyr Leu
            2995            3000            3005 ctc ccc aac cga tgaaggttgg ggtaaacact ccggcctctt aggccattcc             9414
Leu Pro Asn Arg
            3010 tgttttttt tttttttct ttgttttt ttgtttttt tttttttt cctttctttt              9474 tttttttt tcctttcttc tttaatggtg gctccatctt agcccctagtc acggctagct        9534 gtgaaaggtc cgtgagccgc atgactgcag agagtgctga tactggcctc tctgcagatc      9594
atgt                                                                    9598

<210> SEQ ID NO 2
<211> LENGTH: 3011
<212> TYPE: PRT
<213> ORGANISM: Hepatitis C virus
```

```
<400> SEQUENCE: 2

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
210                 215                 220

Gly Cys Val Pro Cys Val Arg Glu Asp Asn Ala Ser Arg Cys Trp Val
225                 230                 235                 240

Pro Val Ala Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Ser
        275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Val Ala Leu Val Met Ala Gln
                325                 330                 335

Leu Leu Arg Val Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Gln
370                 375                 380

Thr Tyr Val Thr Gly Gly Ser Ala Ala Arg Gly Ala Ser Gly Leu Ala
385                 390                 395                 400

Asn Leu Phe Thr Pro Gly Ala Lys Gln Asp Ile Gln Leu Ile Asn Thr
            405                 410                 415
```

Asn Gly Ser Trp His Ile Asn Arg Thr Ala Leu Asn Cys Asn Ala Ser
            420                 425                 430

Leu Asp Thr Gly Trp Val Ala Gly Leu Phe Tyr Tyr His Lys Phe Asn
            435                 440                 445

Ser Ser Gly Cys Pro Glu Arg Met Ala Ser Cys Lys Pro Leu Ala Asp
            450                 455                 460

Phe Asp Gln Gly Trp Gly Pro Ile Arg His Ala Asn Gly Ser Gly Pro
465                 470                 475                 480

Glu His Arg Pro Tyr Cys Trp His Tyr Pro Pro Lys Pro Cys Gly Ile
            485                 490                 495

Val Ser Ala Gln Thr Val Cys Gly Pro Val Tyr Cys Phe Thr Pro Ser
            500                 505                 510

Pro Val Val Val Gly Thr Thr Asn Arg Leu Gly Val Pro Thr Tyr Ser
            515                 520                 525

Trp Gly Thr Asn Asp Thr Asp Val Phe Val Leu Asn Asn Thr Arg Pro
530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Val Gly Asn
            565                 570                 575

Asn Thr Leu His Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
            595                 600                 605

Val His Tyr Pro Tyr Arg Leu Trp His Tyr Pro Cys Thr Val Asn Tyr
            610                 615                 620

Thr Leu Phe Lys Val Arg Met Tyr Val Gly Gly Val Glu His Arg Leu
625                 630                 635                 640

Glu Val Ala Cys Asn Trp Thr Arg Gly Glu Arg Cys Asp Leu Asp Asp
                        645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Thr Thr Gly
            675                 680                 685

Leu Ile His Leu His Gln Asn Ile Val Asp Val Gln Tyr Leu Tyr Gly
            690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                        725                 730                 735

Met Met Leu Leu Ile Ser Gln Ala Glu Ala Ala Leu Glu Asn Leu Val
            740                 745                 750

Leu Leu Asn Ala Ala Ser Leu Ala Gly Thr His Gly Leu Ala Ser Phe
            755                 760                 765

Leu Val Phe Phe Cys Phe Ala Trp Tyr Leu Lys Gly Arg Trp Val Pro
            770                 775                 780

Gly Val Ala Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Met Ala Ala
            805                 810                 815

Ser Cys Gly Gly Val Val Leu Val Gly Leu Met Ala Leu Thr Leu Ser
            820                 825                 830

Pro Tyr Tyr Lys Ser Tyr Ile Ser Trp Cys Leu Trp Trp Leu Gln Tyr

-continued

```
            835                 840                 845
Phe Leu Thr Arg Ile Glu Ala Leu Leu His Val Trp Val Pro Pro Leu
850                 855                 860

Asn Val Arg Gly Gly Arg Asp Ala Val Ile Leu Leu Thr Cys Val Val
865                 870                 875                 880

His Pro Thr Leu Val Phe Asp Ile Thr Lys Leu Leu Ala Val Phe
                    885                 890                 895

Gly Pro Leu Trp Ile Leu Gln Thr Ser Leu Leu Lys Val Pro Tyr Phe
                    900                 905                 910

Val Arg Val Gln Gly Leu Leu Arg Ala Cys Ala Leu Ala Arg Lys Val
                    915                 920                 925

Ala Gly Gly His Tyr Val Gln Met Val Ile Ile Lys Leu Gly Ala Leu
930                 935                 940

Thr Gly Thr Tyr Ile Tyr Asn His Leu Thr Pro Leu Arg Asp Trp Ala
945                 950                 955                 960

His Asn Gly Leu Arg Asp Leu Ala Val Ala Val Glu Pro Val Val Phe
                    965                 970                 975

Ser Gln Met Glu Thr Lys Leu Ile Thr Trp Gly Ala Asp Thr Ala Ala
                    980                 985                 990

Cys Gly Asp Ile Ile Asn Gly Leu  Pro Val Ser Ala Arg  Arg Gly Gln
                    995                 1000                1005

Glu Ile  Leu Leu Gly Pro Ala  Asp Gly Met Val Ser  Lys Gly Trp
    1010                1015                1020

Arg Leu  Leu Ala Pro Ile Thr  Ala Tyr Ala Gln Gln  Thr Arg Gly
    1025                1030                1035

Leu Leu  Gly Cys Ile Ile Thr  Ser Leu Thr Gly Arg  Asp Lys Asn
    1040                1045                1050

Gln Val  Glu Gly Glu Val Gln  Ile Val Ser Thr Ala  Ala Gln Thr
    1055                1060                1065

Phe Leu  Ala Thr Cys Ile Asn  Gly Val Cys Trp Thr  Val Tyr His
    1070                1075                1080

Gly Ala  Gly Thr Arg Thr Ile  Ala Ser Pro Lys Gly  Pro Val Ile
    1085                1090                1095

Gln Met  Tyr Thr Asn Val Asp  Gln Asp Leu Val Gly  Trp Pro Ala
    1100                1105                1110

Pro Gln  Gly Ala Arg Ser Leu  Thr Pro Cys Thr Cys  Gly Ser Ser
    1115                1120                1125

Asp Leu  Tyr Leu Val Thr Arg  His Ala Asp Val Ile  Pro Val Arg
    1130                1135                1140

Arg Arg  Gly Asp Ser Arg Gly  Ser Leu Leu Ser Pro  Arg Pro Ile
    1145                1150                1155

Ser Tyr  Leu Lys Gly Ser Ser  Gly Gly Pro Leu Leu  Cys Pro Ala
    1160                1165                1170

Gly His  Ala Val Gly Ile Phe  Arg Ala Ala Val Cys  Thr Arg Gly
    1175                1180                1185

Val Ala  Lys Ala Val Asp Phe  Ile Pro Val Glu Ser  Leu Glu Thr
    1190                1195                1200

Thr Met  Arg Ser Pro Val Phe  Thr Asp Asn Ser Ser  Pro Pro Ala
    1205                1210                1215

Val Pro  Gln Ser Phe Gln Val  Ala His Leu His Ala  Pro Thr Gly
    1220                1225                1230

Ser Gly  Lys Ser Thr Lys Val  Pro Ala Ala Tyr Ala  Ala Gln Gly
    1235                1240                1245
```

-continued

| | | | | | | | | | |
|---|---|---|---|---|---|---|---|---|---|
| Tyr | Lys | Val | Leu | Val | Leu | Asn | Pro | Ser | Val | Ala | Ala | Thr | Leu | Gly |
| | 1250 | | | | 1255 | | | | 1260 | | | | | |
| Phe | Gly | Ala | Tyr | Met | Ser | Lys | Ala | His | Gly | Ile | Asp | Pro | Asn | Ile |
| 1265 | | | | | 1270 | | | | | 1275 | | | | |
| Arg | Thr | Gly | Val | Arg | Thr | Ile | Thr | Thr | Gly | Ser | Pro | Ile | Thr | Tyr |
| | 1280 | | | | | 1285 | | | | | 1290 | | | |
| Ser | Thr | Tyr | Gly | Lys | Phe | Leu | Ala | Asp | Gly | Gly | Cys | Ser | Gly | Gly |
| 1295 | | | | | 1300 | | | | | 1305 | | | | |
| Ala | Tyr | Asp | Ile | Ile | Ile | Cys | Asp | Glu | Cys | His | Ser | Thr | Asp | Ala |
| 1310 | | | | | 1315 | | | | | 1320 | | | | |
| Thr | Ser | Val | Leu | Gly | Ile | Gly | Thr | Val | Leu | Asp | Gln | Ala | Glu | Thr |
| | 1325 | | | | | 1330 | | | | | 1335 | | | |
| Ala | Gly | Ala | Arg | Leu | Val | Val | Leu | Ala | Thr | Ala | Thr | Pro | Pro | Gly |
| | 1340 | | | | | 1345 | | | | | 1350 | | | |
| Ser | Val | Thr | Val | Pro | His | Pro | Asn | Ile | Glu | Glu | Val | Ala | Leu | Ser |
| | 1355 | | | | | 1360 | | | | | 1365 | | | |
| Thr | Thr | Gly | Glu | Ile | Pro | Phe | Tyr | Gly | Lys | Ala | Ile | Pro | Leu | Glu |
| | 1370 | | | | | 1375 | | | | | 1380 | | | |
| Ala | Ile | Lys | Gly | Gly | Arg | His | Leu | Ile | Phe | Cys | His | Ser | Lys | Lys |
| 1385 | | | | | 1390 | | | | | 1395 | | | | |
| Lys | Cys | Asp | Glu | Leu | Ala | Ala | Lys | Leu | Val | Ala | Met | Gly | Val | Asn |
| 1400 | | | | | 1405 | | | | | 1410 | | | | |
| Ala | Val | Ala | Tyr | Tyr | Arg | Gly | Leu | Asp | Val | Ser | Val | Ile | Pro | Thr |
| 1415 | | | | | 1420 | | | | | 1425 | | | | |
| Ser | Gly | Asp | Val | Val | Val | Ala | Thr | Asp | Ala | Leu | Met | Thr | Gly | |
| 1430 | | | | | 1435 | | | | | 1440 | | | | |
| Tyr | Thr | Gly | Asp | Phe | Asp | Ser | Val | Ile | Asp | Cys | Asn | Thr | Cys | Val |
| 1445 | | | | | 1450 | | | | | 1455 | | | | |
| Thr | Gln | Thr | Val | Asp | Phe | Ser | Leu | Asp | Pro | Thr | Phe | Thr | Ile | Glu |
| 1460 | | | | | 1465 | | | | | 1470 | | | | |
| Thr | Thr | Thr | Leu | Pro | Gln | Asp | Ala | Val | Ser | Arg | Thr | Gln | Arg | Arg |
| 1475 | | | | | 1480 | | | | | 1485 | | | | |
| Gly | Arg | Thr | Gly | Arg | Gly | Lys | Pro | Gly | Ile | Tyr | Arg | Phe | Val | Ala |
| | 1490 | | | | | 1495 | | | | | 1500 | | | |
| Pro | Gly | Glu | Arg | Pro | Ser | Gly | Met | Phe | Asp | Ser | Ser | Val | Leu | Cys |
| | 1505 | | | | | 1510 | | | | | 1515 | | | |
| Glu | Cys | Tyr | Asp | Ala | Gly | Cys | Ala | Trp | Tyr | Glu | Leu | Thr | Pro | Ala |
| | 1520 | | | | | 1525 | | | | | 1530 | | | |
| Glu | Thr | Thr | Val | Arg | Leu | Arg | Ala | Tyr | Met | Asn | Thr | Pro | Gly | Leu |
| | 1535 | | | | | 1540 | | | | | 1545 | | | |
| Pro | Val | Cys | Gln | Asp | His | Leu | Glu | Phe | Trp | Glu | Gly | Val | Phe | Thr |
| | 1550 | | | | | 1555 | | | | | 1560 | | | |
| Gly | Leu | Thr | His | Ile | Asp | Ala | His | Phe | Leu | Ser | Gln | Thr | Lys | Gln |
| | 1565 | | | | | 1570 | | | | | 1575 | | | |
| Ser | Gly | Glu | Asn | Leu | Pro | Tyr | Leu | Val | Ala | Tyr | Gln | Ala | Thr | Val |
| | 1580 | | | | | 1585 | | | | | 1590 | | | |
| Cys | Ala | Arg | Ala | Gln | Ala | Pro | Pro | Pro | Ser | Trp | Asp | Gln | Met | Trp |
| 1595 | | | | | 1600 | | | | | 1605 | | | | |
| Lys | Cys | Leu | Ile | Arg | Leu | Lys | Pro | Thr | Leu | His | Gly | Pro | Thr | Pro |
| 1610 | | | | | 1615 | | | | | 1620 | | | | |
| Leu | Leu | Tyr | Arg | Leu | Gly | Ala | Val | Gln | Asn | Glu | Val | Thr | Leu | Thr |
| | 1625 | | | | | 1630 | | | | | 1635 | | | |
| His | Pro | Ile | Thr | Lys | Tyr | Ile | Met | Thr | Cys | Met | Ser | Ala | Asp | Leu |
| 1640 | | | | | 1645 | | | | | 1650 | | | | |

```
Glu Val Val Thr Ser Thr Trp Val Leu Val Gly Gly Val Leu Ala
    1655            1660            1665

Ala Leu Ala Ala Tyr Cys Leu Ser Thr Gly Cys Val Val Ile Val
    1670            1675            1680

Gly Arg Ile Val Leu Ser Gly Lys Pro Ala Ile Ile Pro Asp Arg
    1685            1690            1695

Glu Val Leu Tyr Arg Glu Phe Asp Glu Met Glu Glu Cys Ser Gln
    1700            1705            1710

His Leu Pro Tyr Ile Glu Gln Gly Met Met Leu Ala Glu Gln Phe
    1715            1720            1725

Lys Gln Lys Ala Leu Gly Leu Leu Gln Thr Ala Ser Arg Gln Ala
    1730            1735            1740

Glu Val Ile Ala Pro Thr Val Gln Thr Asn Trp Gln Arg Leu Glu
    1745            1750            1755

Ala Phe Trp Ala Lys His Met Trp Asn Phe Ile Ser Gly Ile Gln
    1760            1765            1770

Tyr Leu Ala Gly Leu Ser Thr Leu Pro Gly Asn Pro Ala Ile Ala
    1775            1780            1785

Ser Leu Met Ala Phe Thr Ala Ala Val Thr Ser Pro Leu Thr Thr
    1790            1795            1800

Gly Gln Thr Leu Leu Phe Asn Ile Leu Gly Gly Trp Val Ala Ala
    1805            1810            1815

Gln Leu Ala Ala Pro Gly Ala Ala Thr Ala Phe Val Gly Ala Gly
    1820            1825            1830

Leu Ala Gly Ala Ala Ile Gly Ser Val Gly Leu Gly Lys Val Leu
    1835            1840            1845

Val Asp Ile Leu Ala Gly Tyr Gly Ala Gly Val Ala Gly Ala Leu
    1850            1855            1860

Val Ala Phe Lys Ile Met Ser Gly Glu Val Pro Ser Thr Glu Asp
    1865            1870            1875

Leu Val Asn Leu Leu Pro Ala Ile Leu Ser Pro Gly Ala Leu Val
    1880            1885            1890

Val Gly Val Val Cys Ala Ala Ile Leu Arg Arg His Val Gly Pro
    1895            1900            1905

Gly Glu Gly Ala Val Gln Trp Met Asn Arg Leu Ile Ala Phe Ala
    1910            1915            1920

Ser Arg Gly Asn His Val Ser Pro Thr His Tyr Val Pro Glu Ser
    1925            1930            1935

Asp Ala Ala Ala Arg Val Thr Ala Ile Leu Ser Ser Leu Thr Val
    1940            1945            1950

Thr Gln Leu Leu Arg Arg Leu His Gln Trp Leu Ser Ser Glu Cys
    1955            1960            1965

Thr Thr Pro Cys Ser Gly Ser Trp Leu Arg Asp Ile Trp Asp Trp
    1970            1975            1980

Ile Cys Glu Val Leu Ser Asp Phe Lys Thr Trp Leu Lys Ala Lys
    1985            1990            1995

Leu Met Pro Gln Leu Pro Gly Ile Pro Phe Val Ser Cys Gln Arg
    2000            2005            2010

Gly Tyr Arg Gly Val Trp Arg Gly Asp Gly Ile Met His Thr Arg
    2015            2020            2025

Cys Pro Cys Gly Ala Glu Ile Ala Gly His Val Lys Asn Gly Thr
    2030            2035            2040

Met Arg Ile Val Gly Pro Lys Thr Cys Arg Asn Thr Trp Ser Gly
```

-continued

```
              2045                2050                2055

Thr  Phe  Pro  Ile  Asn  Ala  Tyr  Thr  Thr  Gly  Pro  Cys  Thr  Pro  Leu
     2060                2065                2070

Pro  Ala  Pro  Asn  Tyr  Thr  Phe  Ala  Leu  Trp  Arg  Val  Ser  Ala  Glu
     2075                2080                2085

Glu  Tyr  Val  Glu  Ile  Arg  Gln  Val  Gly  Asp  Phe  His  Tyr  Val  Thr
     2090                2095                2100

Gly  Met  Thr  Ala  Asp  Asn  Leu  Lys  Cys  Pro  Cys  Gln  Val  Pro  Ser
     2105                2110                2115

Pro  Glu  Phe  Phe  Thr  Glu  Leu  Asp  Gly  Val  Arg  Leu  His  Arg  Phe
     2120                2125                2130

Ala  Pro  Pro  Cys  Lys  Pro  Leu  Leu  Arg  Asp  Glu  Val  Ser  Phe  Arg
     2135                2140                2145

Val  Gly  Leu  His  Asp  Tyr  Pro  Val  Gly  Ser  Gln  Leu  Pro  Cys  Glu
     2150                2155                2160

Pro  Glu  Pro  Asp  Val  Ala  Val  Leu  Thr  Ser  Met  Leu  Thr  Asp  Pro
     2165                2170                2175

Ser  His  Ile  Thr  Ala  Glu  Ala  Ala  Gly  Arg  Arg  Leu  Ala  Arg  Gly
     2180                2185                2190

Ser  Pro  Pro  Ser  Leu  Ala  Ser  Ser  Ala  Ser  Gln  Leu  Ser  Ala
     2195                2200                2205

Pro  Ser  Leu  Lys  Ala  Thr  Cys  Thr  Thr  Asn  His  Asp  Ser  Pro  Asp
     2210                2215                2220

Ala  Glu  Leu  Ile  Glu  Ala  Asn  Leu  Leu  Trp  Arg  Gln  Glu  Met  Gly
     2225                2230                2235

Gly  Asn  Ile  Thr  Arg  Val  Glu  Ser  Glu  Asn  Lys  Val  Val  Val  Leu
     2240                2245                2250

Asp  Ser  Phe  Asp  Pro  Leu  Val  Ala  Glu  Glu  Asp  Glu  Arg  Glu  Ile
     2255                2260                2265

Ser  Val  Ala  Ala  Glu  Ile  Leu  Arg  Lys  Ser  Arg  Arg  Phe  Ala  Pro
     2270                2275                2280

Ala  Leu  Pro  Ile  Trp  Ala  Arg  Pro  Asp  Tyr  Asn  Pro  Pro  Leu  Leu
     2285                2290                2295

Glu  Thr  Trp  Lys  Lys  Pro  Asp  Tyr  Glu  Pro  Pro  Val  Val  His  Gly
     2300                2305                2310

Cys  Pro  Leu  Pro  Pro  Pro  Lys  Ser  Pro  Pro  Val  Pro  Pro  Pro  Arg
     2315                2320                2325

Lys  Lys  Arg  Thr  Val  Val  Leu  Thr  Glu  Ser  Thr  Val  Ser  Thr  Ala
     2330                2335                2340

Leu  Ala  Glu  Leu  Ala  Thr  Lys  Ser  Phe  Gly  Ser  Ser  Ser  Thr  Ser
     2345                2350                2355

Gly  Ile  Thr  Gly  Asp  Asn  Thr  Thr  Ala  Ser  Ser  Glu  Pro  Ala  Pro
     2360                2365                2370

Ser  Val  Cys  Pro  Pro  Asp  Ser  Asp  Ala  Glu  Ser  Tyr  Ser  Ser  Met
     2375                2380                2385

Pro  Pro  Leu  Glu  Gly  Glu  Pro  Gly  Asp  Pro  Asp  Leu  Ser  Asp  Gly
     2390                2395                2400

Ser  Trp  Ser  Thr  Val  Ser  Ser  Gly  Ala  Gly  Thr  Glu  Asp  Val  Val
     2405                2410                2415

Cys  Cys  Ser  Met  Ser  Tyr  Ser  Trp  Thr  Gly  Ala  Leu  Ile  Thr  Pro
     2420                2425                2430

Cys  Ala  Ala  Glu  Glu  Gln  Lys  Leu  Pro  Ile  Asn  Ala  Leu  Ser  Asn
     2435                2440                2445
```

-continued

```
Ser Leu Leu Arg His His Asn Leu Val Tyr Ser Thr Thr Ser Arg
2450                2455                2460

Ser Ala Cys Gln Arg Gln Lys Lys Val Thr Phe Asp Arg Leu Gln
2465                2470                2475

Val Leu Asp Asn His Tyr Gln Asp Val Leu Lys Glu Val Lys Ala
2480                2485                2490

Ala Ala Ser Lys Val Lys Ala Asn Leu Leu Ser Val Glu Glu Ala
2495                2500                2505

Cys Ser Leu Thr Pro Pro His Ser Ala Arg Ser Lys Phe Gly Tyr
2510                2515                2520

Gly Ala Lys Asp Val Arg Cys His Ala Arg Lys Ala Val Asn His
2525                2530                2535

Ile Asn Ser Val Trp Lys Asp Leu Leu Glu Asp Ser Val Thr Pro
2540                2545                2550

Ile Asp Thr Thr Ile Met Ala Lys Asn Glu Val Phe Cys Val Gln
2555                2560                2565

Pro Glu Lys Gly Gly Arg Lys Pro Ala Arg Leu Ile Val Tyr Pro
2570                2575                2580

Asp Leu Gly Val Arg Val Cys Glu Lys Met Ala Leu Tyr Asp Val
2585                2590                2595

Val Lys Lys Leu Pro Leu Ala Val Met Gly Ser Ser Tyr Gly Phe
2600                2605                2610

Gln Tyr Ser Pro Gly Gln Arg Val Glu Phe Leu Val Gln Ala Trp
2615                2620                2625

Lys Ser Lys Gly Thr Pro Met Gly Phe Ser Tyr Asp Thr Arg Cys
2630                2635                2640

Phe Asp Ser Thr Val Thr Glu Ser Asp Ile Arg Thr Glu Glu Ala
2645                2650                2655

Ile Tyr Gln Cys Cys Asp Leu Asp Pro Gln Ala Arg Val Ala Ile
2660                2665                2670

Lys Ser Leu Thr Glu Arg Leu Tyr Val Gly Gly Pro Leu Thr Asn
2675                2680                2685

Ser Arg Gly Glu Asn Cys Gly Tyr Arg Arg Cys Arg Ala Ser Gly
2690                2695                2700

Val Leu Thr Thr Ser Cys Gly Asn Thr Leu Thr Cys Tyr Ile Lys
2705                2710                2715

Ala Arg Ala Ala Cys Arg Ala Ala Gly Leu Arg Asp Cys Thr Met
2720                2725                2730

Leu Val Cys Gly Asp Asp Leu Val Val Ile Cys Glu Ser Gln Gly
2735                2740                2745

Val Gln Glu Asp Thr Ala Ser Leu Arg Ala Phe Thr Glu Ala Met
2750                2755                2760

Thr Arg Tyr Ser Ala Pro Pro Gly Asp Pro Pro Gln Pro Glu Tyr
2765                2770                2775

Asp Leu Glu Leu Ile Thr Ser Cys Ser Ser Asn Val Ser Val Ala
2780                2785                2790

His Asp Asp Thr Gly Lys Arg Val Tyr Tyr Leu Thr Arg Asp Pro
2795                2800                2805

Thr Thr Pro Leu Ala Arg Ala Ala Trp Glu Thr Ala Arg His Thr
2810                2815                2820

Pro Val Asn Ser Trp Leu Gly Asn Ile Ile Met Phe Ala Pro Thr
2825                2830                2835

Leu Trp Val Arg Met Ile Leu Leu Pro His Phe Phe Ser Val Leu
2840                2845                2850
```

```
Met Ala Arg Asp Gln Leu Glu Gln Ala Leu Asp Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Ile Arg
    2915                2920                2925

Ala Lys Leu Leu Ser Arg Gly Gly Arg Ala Ala Thr Cys Gly Lys
    2930                2935                2940

Tyr Leu Phe Asn Trp Ala Val Arg Thr Lys Leu Lys Leu Thr Pro
    2945                2950                2955

Ile Ala Ala Ala Ser Gln Leu Asp Leu Ser Gly Trp Phe Thr Ala
    2960                2965                2970

Gly Tyr Ser Gly Gly Asp Ile Tyr His Ser Val Ser Arg Ala Arg
    2975                2980                2985

Pro Arg Trp Phe Trp Phe Cys Leu Leu Leu Leu Ala Ala Gly Val
    2990                2995                3000

Gly Ile Tyr Leu Leu Pro Asn Arg
    3005                3010

<210> SEQ ID NO 3
<211> LENGTH: 7946
<212> TYPE: DNA
<213> ORGANISM: Artificial Sequence
<220> FEATURE:
<223> OTHER INFORMATION: Description of Artificial Sequence: Synthetic
      replicon polynucleotide
<220> FEATURE:
<221> NAME/KEY: CDS
<222> LOCATION: (342)..(1181)
<220> FEATURE:
<221> NAME/KEY: CDS
<222> LOCATION: (1765)..(7722)

<400> SEQUENCE: 3
gccagccccc tgatggggc gacactccac catgaatcac tcccctgtga ggaactactg      60
tcttcacgca gaaagcgtct agccatggcg ttagtatgag tgtcgtgcag cctccaggac    120 ccccctccc gggagagcca tagtggtctg cggaaccggt gagtacaccg gaattgccag    180
gacgaccggg tcctttcttg gatcaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac c atg agc acg aat cct    356
                                              Met Ser Thr Asn Pro
                                                1               5 aaa cct caa aga aaa acc aaa cgt aac acc aac atg atc gaa caa gat      404
Lys Pro Gln Arg Lys Thr Lys Arg Asn Thr Asn Met Ile Glu Gln Asp
            10                  15                  20 gga ttg cac gca ggt tct ccg gcc gct tgg gtg gag agg cta ttc ggc      452
Gly Leu His Ala Gly Ser Pro Ala Ala Trp Val Glu Arg Leu Phe Gly
        25                  30                  35 tat gac tgg gca caa cag aca atc ggc tgc tct gat gcc gcc gtg ttc      500
Tyr Asp Trp Ala Gln Gln Thr Ile Gly Cys Ser Asp Ala Ala Val Phe
    40                  45                  50 cgg ctg tca gcg cag ggg cgc ccg gtt ctt ttt gtc aag acc gac ctg      548
Arg Leu Ser Ala Gln Gly Arg Pro Val Leu Phe Val Lys Thr Asp Leu
55                  60                  65
```

```
tcc ggt gcc ctg aat gaa ctg cag gac gag gca gcg cgg cta tcg tgg      596
Ser Gly Ala Leu Asn Glu Leu Gln Asp Glu Ala Ala Arg Leu Ser Trp
 70              75                  80                  85 ctg gcc acg acg ggc gtt cct tgc gca gct gtg ctc gac gtt gtc act      644
Leu Ala Thr Thr Gly Val Pro Cys Ala Ala Val Leu Asp Val Val Thr
             90                  95                 100 gaa gcg gga agg gac tgg ctg cta ttg ggc gaa gtg ccg ggg cag gat      692
Glu Ala Gly Arg Asp Trp Leu Leu Leu Gly Glu Val Pro Gly Gln Asp
                105                 110                 115 ctc ctg tca tct cac ctt gct cct gcc gag aaa gta tcc atc atg gct      740
Leu Leu Ser Ser His Leu Ala Pro Ala Glu Lys Val Ser Ile Met Ala
        120                 125                 130 gat gca atg cgg cgg ctg cat acg ctt gat ccg gct acc tgc cca ttc      788
Asp Ala Met Arg Arg Leu His Thr Leu Asp Pro Ala Thr Cys Pro Phe
    135                 140                 145 gac cac caa gcg aaa cat cgc atc gag cga gca cgt act cgg atg gaa      836
Asp His Gln Ala Lys His Arg Ile Glu Arg Ala Arg Thr Arg Met Glu
150                 155                 160                 165 gcc ggt ctt gtc gat cag gat gat ctg gac gaa gag cat cag ggg ctc      884
Ala Gly Leu Val Asp Gln Asp Asp Leu Asp Glu Glu His Gln Gly Leu
                170                 175                 180 gcg cca gcc gaa ctg ttc gcc agg ctc aag gcg cgc atg ccc gac ggc      932
Ala Pro Ala Glu Leu Phe Ala Arg Leu Lys Ala Arg Met Pro Asp Gly
            185                 190                 195 gag gat ctc gtc gtg acc cat ggc gat gcc tgc ttg ccg aat atc atg      980
Glu Asp Leu Val Val Thr His Gly Asp Ala Cys Leu Pro Asn Ile Met
        200                 205                 210 gtg gaa aat ggc cgc ttt tct gga ttc atc gac tgt ggc cgg ctg ggt     1028
Val Glu Asn Gly Arg Phe Ser Gly Phe Ile Asp Cys Gly Arg Leu Gly
    215                 220                 225 gtg gcg gac cgc tat cag gac ata gcg ttg gct acc cgt gat att gct     1076
Val Ala Asp Arg Tyr Gln Asp Ile Ala Leu Ala Thr Arg Asp Ile Ala
230                 235                 240                 245 gaa gag ctt ggc ggc gaa tgg gct gac cgc ttc ctc gtg ctt tac ggt     1124
Glu Glu Leu Gly Gly Glu Trp Ala Asp Arg Phe Leu Val Leu Tyr Gly
                250                 255                 260 atc gcc gct ccc gat tcg cag cgc atc gcc ttc tat cgc ctt ctt gac     1172
Ile Ala Ala Pro Asp Ser Gln Arg Ile Ala Phe Tyr Arg Leu Leu Asp
            265                 270                 275 gag ttc ttc tgagtttaaa ccctctccct ccccccccc taacgttact              1221
Glu Phe Phe
        280 ggccgaagcc gcttggaata aggccggtgt gcgtttgtct atatgttatt ttccaccata   1281 ttgccgtctt ttggcaatgt gagggcccgg aaacctggcc ctgtcttctt gacgagcatt   1341 cctagggtc tttcccctct cgccaaagga atgcaaggtc tgttgaatgt cgtgaaggaa    1401 gcagttcctc tggaagcttc ttgaagacaa acaacgtctg tagcgaccct ttgcaggcag   1461 cggaaccccc cacctggcga caggtgcctc tgcggccaaa agccacgtgt ataagataca   1521 cctgcaaagg cggcacaacc ccagtgccac gttgtgagtt ggatagttgt ggaaagagtc   1581 aaatggctct cctcaagcgt attcaacaag gggctgaagg atgcccagaa ggtaccccat   1641 tgtatgggat ctgatctggg gcctcggtgc acatgcttta catgtgttta gtcgaggtta   1701 aaaaacgtct aggcccccg aaccacgggg acgtggtttt cctttgaaaa acacgataat    1761 acc atg gcg ccc atc acg gcg tat gcc cag cag aca agg ggc ctc ctg    1809
    Met Ala Pro Ile Thr Ala Tyr Ala Gln Gln Thr Arg Gly Leu Leu
                285                 290                 295 gga tgc ata att act agc ctg acc ggc cgg gac aaa aac cag gtg gag    1857
```

-continued

| | | |
|---|---|---|
| Gly Cys Ile Ile Thr Ser Leu Thr Gly Arg Asp Lys Asn Gln Val Glu<br>300 305 310 | | |
| ggt gag gtc cag att gtg tca act gct gcc cag acc ttc ctg gca acc<br>Gly Glu Val Gln Ile Val Ser Thr Ala Ala Gln Thr Phe Leu Ala Thr<br>315 320 325 | 1905 | |
| tgc atc aac gga gtg tgc tgg act gtc tac cac ggg gcc gga aca agg<br>Cys Ile Asn Gly Val Cys Trp Thr Val Tyr His Gly Ala Gly Thr Arg<br>330 335 340 | 1953 | |
| acc atc gcg tca ccc aaa ggt ccc gtc atc cag atg tat act aat gta<br>Thr Ile Ala Ser Pro Lys Gly Pro Val Ile Gln Met Tyr Thr Asn Val<br>345 350 355 | 2001 | |
| gac caa gac ctt gta ggc tgg ccc gct ccc caa ggt gcc cgc tca ttg<br>Asp Gln Asp Leu Val Gly Trp Pro Ala Pro Gln Gly Ala Arg Ser Leu<br>360 365 370 375 | 2049 | |
| aca ccc tgc act tgc ggc tcc tcg gac ctt tac ttg gtc acg agg cac<br>Thr Pro Cys Thr Cys Gly Ser Ser Asp Leu Tyr Leu Val Thr Arg His<br>380 385 390 | 2097 | |
| gcc gat gtc att ccc gtg cgc cgg cgg ggt gat agc agg ggc agc ctg<br>Ala Asp Val Ile Pro Val Arg Arg Arg Gly Asp Ser Arg Gly Ser Leu<br>395 400 405 | 2145 | |
| ctc tcg ccc cgg cct atc tct tac ttg aaa ggc tct tcg ggg ggc cca<br>Leu Ser Pro Arg Pro Ile Ser Tyr Leu Lys Gly Ser Ser Gly Gly Pro<br>410 415 420 | 2193 | |
| ttg ctg tgc ccc gcg gga cac gcc gta ggc ata ttc agg gcc gcg gtg<br>Leu Leu Cys Pro Ala Gly His Ala Val Gly Ile Phe Arg Ala Ala Val<br>425 430 435 | 2241 | |
| tgc acc cgt gga gtg gct aag gcg gtg gac ttt atc ccc gta gag agc<br>Cys Thr Arg Gly Val Ala Lys Ala Val Asp Phe Ile Pro Val Glu Ser<br>440 445 450 455 | 2289 | |
| cta gag aca acc atg agg tcc ccg gtg ttc aca gac aac tcc tcc cca<br>Leu Glu Thr Thr Met Arg Ser Pro Val Phe Thr Asp Asn Ser Ser Pro<br>460 465 470 | 2337 | |
| cca gca gtg ccc cag agc ttc cag gtg gcc cac ctg cat gct ccc acc<br>Pro Ala Val Pro Gln Ser Phe Gln Val Ala His Leu His Ala Pro Thr<br>475 480 485 | 2385 | |
| ggc agc ggt aag agt acc aag gtc ccg gcc gca tac gcg gct cag ggc<br>Gly Ser Gly Lys Ser Thr Lys Val Pro Ala Ala Tyr Ala Ala Gln Gly<br>490 495 500 | 2433 | |
| tac aag gtg ctg gtg ctc aac ccc tcc gtt gct gca aca ctg ggc ttt<br>Tyr Lys Val Leu Val Leu Asn Pro Ser Val Ala Ala Thr Leu Gly Phe<br>505 510 515 | 2481 | |
| ggt gct tat atg tcc aag gcc cat ggg att gat cct aac atc agg act<br>Gly Ala Tyr Met Ser Lys Ala His Gly Ile Asp Pro Asn Ile Arg Thr<br>520 525 530 535 | 2529 | |
| ggg gtg agg aca atc act act ggc agc ccc atc acg tac tcc acc tac<br>Gly Val Arg Thr Ile Thr Thr Gly Ser Pro Ile Thr Tyr Ser Thr Tyr<br>540 545 550 | 2577 | |
| ggc aag ttc ctt gct gat ggc ggg tgc tcg ggg ggt gct tat gac ata<br>Gly Lys Phe Leu Ala Asp Gly Gly Cys Ser Gly Gly Ala Tyr Asp Ile<br>555 560 565 | 2625 | |
| ata att tgt gac gag tgc cac tct acg gat gca aca tcc gtc ttg ggc<br>Ile Ile Cys Asp Glu Cys His Ser Thr Asp Ala Thr Ser Val Leu Gly<br>570 575 580 | 2673 | |
| atc ggc act gtc ctt gac caa gca gag act gcg ggg gcg aga ctg gtc<br>Ile Gly Thr Val Leu Asp Gln Ala Glu Thr Ala Gly Ala Arg Leu Val<br>585 590 595 | 2721 | |
| gtg ctc gcc acc gct acc cct ccg ggc tct gtc act gtg ccc cat cct<br>Val Leu Ala Thr Ala Thr Pro Pro Gly Ser Val Thr Val Pro His Pro<br>600 605 610 615 | 2769 | |
| aac atc gag gag gtt gct ctg tcc acc acc gga gag atc ccc ttt tac<br> | 2817 | |

-continued

| | | | | | | | | | | | | | | |
|---|---|---|---|---|---|---|---|---|---|---|---|---|---|---|
| Asn | Ile | Glu | Glu | Val | Ala | Leu | Ser | Thr | Thr | Gly | Ile | Pro | Phe | Tyr |
| | | | 620 | | | | 625 | | | | | 630 | | |

```
ggc aag gct atc ccc ctt gag gca atc aag ggg ggg aga cat ctc atc      2865
Gly Lys Ala Ile Pro Leu Glu Ala Ile Lys Gly Gly Arg His Leu Ile
            635                 640                 645 ttc tgc cat tca aaa aag aag tgc gac gag ctc gct gca aag ctg gtc      2913
Phe Cys His Ser Lys Lys Lys Cys Asp Glu Leu Ala Ala Lys Leu Val
            650                 655                 660 gcg atg ggc gtc aat gcc gtg gct tac tac cgc ggc ctc gac gtg tcc      2961
Ala Met Gly Val Asn Ala Val Ala Tyr Tyr Arg Gly Leu Asp Val Ser
            665                 670                 675 gtc atc cca acc agt ggc gat gtt gtc gtc gtg gca act gat gcc ctc      3009
Val Ile Pro Thr Ser Gly Asp Val Val Val Val Ala Thr Asp Ala Leu
680                 685                 690                 695 atg acc ggc tat acc ggc gac ttt gac tcg gtg ata gac tgc aac acg      3057
Met Thr Gly Tyr Thr Gly Asp Phe Asp Ser Val Ile Asp Cys Asn Thr
                700                 705                 710 tgt gtc acc cag aca gtc gac ttc agc ctt gac cct acc ttc acc att      3105
Cys Val Thr Gln Thr Val Asp Phe Ser Leu Asp Pro Thr Phe Thr Ile
            715                 720                 725 gag aca acc acg ctc ccc cag gac gct gtc tcc cgc act caa cgt cgg      3153
Glu Thr Thr Thr Leu Pro Gln Asp Ala Val Ser Arg Thr Gln Arg Arg
            730                 735                 740 ggc agg act ggc agg ggg aag cca ggc atc tac aga ttt gtg gca ccg      3201
Gly Arg Thr Gly Arg Gly Lys Pro Gly Ile Tyr Arg Phe Val Ala Pro
745                 750                 755 ggg gag cgc ccc tcc ggc atg ttt gac tcg tcc gtc ctc tgt gag tgc      3249
Gly Glu Arg Pro Ser Gly Met Phe Asp Ser Ser Val Leu Cys Glu Cys
760                 765                 770                 775 tat gac gcg ggc tgt gct tgg tat gag ctc aca ccc gcc gag acc aca      3297
Tyr Asp Ala Gly Cys Ala Trp Tyr Glu Leu Thr Pro Ala Glu Thr Thr
                780                 785                 790 gtt agg cta cga gca tat atg aac acc ccg ggg ctc ccc gtg tgc caa      3345
Val Arg Leu Arg Ala Tyr Met Asn Thr Pro Gly Leu Pro Val Cys Gln
            795                 800                 805 gac cat ctt gaa ttt tgg gag ggc gtc ttc acg ggt ctc acc cat ata      3393
Asp His Leu Glu Phe Trp Glu Gly Val Phe Thr Gly Leu Thr His Ile
            810                 815                 820 gac gcc cat ttc cta tcc cag aca aag cag agt ggg gaa aac ctt cct      3441
Asp Ala His Phe Leu Ser Gln Thr Lys Gln Ser Gly Glu Asn Leu Pro
825                 830                 835 tac ctg gta gcg tac caa gcc acc gtg tgc gct agg gct cag gcc ccc      3489
Tyr Leu Val Ala Tyr Gln Ala Thr Val Cys Ala Arg Ala Gln Ala Pro
840                 845                 850                 855 ccc cca tcg tgg gac cag atg tgg aag tgc ttg atc cgc ctc aag ccc      3537
Pro Pro Ser Trp Asp Gln Met Trp Lys Cys Leu Ile Arg Leu Lys Pro
                860                 865                 870 acc ctt cat ggg cca aca cct ctg cta tac aga ctg ggc gct gtt cag      3585
Thr Leu His Gly Pro Thr Pro Leu Leu Tyr Arg Leu Gly Ala Val Gln
            875                 880                 885 aat gaa gtc acc ctg acg cac cca atc acc aag tac atc atg aca tgc      3633
Asn Glu Val Thr Leu Thr His Pro Ile Thr Lys Tyr Ile Met Thr Cys
            890                 895                 900 atg tcg gct gac ctg gag gtc gtc acg agt acc tgg gtg ctc gtc ggc      3681
Met Ser Ala Asp Leu Glu Val Val Thr Ser Thr Trp Val Leu Val Gly
905                 910                 915 ggc gtc ctg gct gct ttg gcc gcg tat tgc cta tcc aca ggc tgc gtg      3729
Gly Val Leu Ala Ala Leu Ala Ala Tyr Cys Leu Ser Thr Gly Cys Val
920                 925                 930                 935 gtc ata gta ggc agg att gtc ttg tcc ggg aag ccg gct atc ata cct      3777
```

|  |  |  |
|---|---|---|
| Val Ile Val Gly Arg Ile Val Leu Ser Gly Lys Pro Ala Ile Ile Pro<br>                         940                   945               950 | |
| gac agg gaa gtc ctc tac cgg gag ttc gat gag atg gaa gag tgc tct<br>Asp Arg Glu Val Leu Tyr Arg Glu Phe Asp Glu Met Glu Glu Cys Ser<br>          955                   960                   965 | 3825 |
| cag cac ttg ccg tac atc gag cag ggg atg atg ctc gcc gag cag ttc<br>Gln His Leu Pro Tyr Ile Glu Gln Gly Met Met Leu Ala Glu Gln Phe<br>    970                   975                   980 | 3873 |
| aag cag aag gcc ctc ggc ctc ctg cag acc gcg tcc cgc cag gca gag<br>Lys Gln Lys Ala Leu Gly Leu Leu Gln Thr Ala Ser Arg Gln Ala Glu<br>        985                   990                   995 | 3921 |
| gtc atc gcc cct acc gtc caa acc aac tgg cag aga ctc gag gcc<br>Val Ile Ala Pro Thr Val Gln Thr Asn Trp Gln Arg Leu Glu Ala<br>1000                  1005                  1010 | 3966 |
| ttc tgg gcg aag cat atg tgg aac ttc atc agt gga ata caa tat<br>Phe Trp Ala Lys His Met Trp Asn Phe Ile Ser Gly Ile Gln Tyr<br>1015                  1020                  1025 | 4011 |
| ctg gcg ggc ctg tca acg ttg cct ggt aat ccc gcc att gca tca<br>Leu Ala Gly Leu Ser Thr Leu Pro Gly Asn Pro Ala Ile Ala Ser<br>1030                  1035                  1040 | 4056 |
| ttg atg gct ttt aca gct gcc gtc acc agc cca cta acc acc ggc<br>Leu Met Ala Phe Thr Ala Ala Val Thr Ser Pro Leu Thr Thr Gly<br>1045                  1050                  1055 | 4101 |
| caa act ctc ctc ttc aac att ttg ggg ggg tgg gtg gct gcc cag<br>Gln Thr Leu Leu Phe Asn Ile Leu Gly Gly Trp Val Ala Ala Gln<br>1060                  1065                  1070 | 4146 |
| ctc gca gcc ccc ggt gcc gct acc gcc ttt gtg ggc gct ggc tta<br>Leu Ala Ala Pro Gly Ala Ala Thr Ala Phe Val Gly Ala Gly Leu<br>1075                  1080                  1085 | 4191 |
| gcc ggc gcc gcc atc ggc agt gtt gga ctg ggg aag gtc ctc gtg<br>Ala Gly Ala Ala Ile Gly Ser Val Gly Leu Gly Lys Val Leu Val<br>1090                  1095                  1100 | 4236 |
| gac atc ctt gca ggg tat ggc gcg ggc gtg gcg gga gct ctt gta<br>Asp Ile Leu Ala Gly Tyr Gly Ala Gly Val Ala Gly Ala Leu Val<br>1105                  1110                  1115 | 4281 |
| gca ttt aag atc atg agc ggt gag gtt ccc tcc aca gag gac ctg<br>Ala Phe Lys Ile Met Ser Gly Glu Val Pro Ser Thr Glu Asp Leu<br>1120                  1125                  1130 | 4326 |
| gtc aat cta ctg cct gcc atc ctt tcg ccc gga gcc ctt gta gtc<br>Val Asn Leu Leu Pro Ala Ile Leu Ser Pro Gly Ala Leu Val Val<br>1135                  1140                  1145 | 4371 |
| ggt gtg gtc tgc gca gca ata cta cgc cgg cac gtt ggc ccg ggc<br>Gly Val Val Cys Ala Ala Ile Leu Arg Arg His Val Gly Pro Gly<br>1150                  1155                  1160 | 4416 |
| gag gga gca gtg cag tgg atg aac cgg ttg ata gcc ttc gcc tcc<br>Glu Gly Ala Val Gln Trp Met Asn Arg Leu Ile Ala Phe Ala Ser<br>1165                  1170                  1175 | 4461 |
| cgg ggg aac cac gtt tcc ccc acg cac tac gtg ccg gag agc gat<br>Arg Gly Asn His Val Ser Pro Thr His Tyr Val Pro Glu Ser Asp<br>1180                  1185                  1190 | 4506 |
| gca gct gcc cgc gtc act gcc ata ctc agc agc ctc act gtg acc<br>Ala Ala Ala Arg Val Thr Ala Ile Leu Ser Ser Leu Thr Val Thr<br>1195                  1200                  1205 | 4551 |
| cag ctc ctg agg cga cta cac cag tgg cta agc tcg gag tgt acc<br>Gln Leu Leu Arg Arg Leu His Gln Trp Leu Ser Ser Glu Cys Thr<br>1210                  1215                  1220 | 4596 |
| act cca tgc tcc ggt tcc tgg cta agg gac atc tgg gac tgg ata<br>Thr Pro Cys Ser Gly Ser Trp Leu Arg Asp Ile Trp Asp Trp Ile<br>1225                  1230                  1235 | 4641 |
| tgc gag gtg ctg agc gat ttt aag acc tgg ctg aag gcc aag ctc | 4686 |

| | | | | | | | | | | | | |
|---|---|---|---|---|---|---|---|---|---|---|---|---|
| Cys | Glu | Val | Leu | Ser | Asp | Phe | Lys | Thr | Trp | Leu | Lys | Ala Lys Leu |
| 1240 | | | | 1245 | | | | | 1250 | | | |

| atg | cca | caa | ctg | cct | ggg | att | ccc | ttt | gtg | tcc | tgc | caa | cgc | ggg | | 4731 |
|---|---|---|---|---|---|---|---|---|---|---|---|---|---|---|---|---|
| Met | Pro | Gln | Leu | Pro | Gly | Ile | Pro | Phe | Val | Ser | Cys | Gln | Arg | Gly | | |
| 1255 | | | | 1260 | | | | | 1265 | | | | | | | |

| tac | agg | ggg | gtc | tgg | cga | gga | gat | ggc | att | atg | cac | act | cgc | tgc | | 4776 |
|---|---|---|---|---|---|---|---|---|---|---|---|---|---|---|---|---|
| Tyr | Arg | Gly | Val | Trp | Arg | Gly | Asp | Gly | Ile | Met | His | Thr | Arg | Cys | | |
| 1270 | | | | 1275 | | | | | 1280 | | | | | | | |

| ccc | tgt | gga | gct | gag | atc | gcc | gga | cat | gtc | aag | aac | ggg | acg | atg | | 4821 |
|---|---|---|---|---|---|---|---|---|---|---|---|---|---|---|---|---|
| Pro | Cys | Gly | Ala | Glu | Ile | Ala | Gly | His | Val | Lys | Asn | Gly | Thr | Met | | |
| 1285 | | | | 1290 | | | | | 1295 | | | | | | | |

| agg | atc | gtc | ggt | cct | aag | acc | tgc | aga | aac | acg | tgg | agt | ggg | acc | | 4866 |
|---|---|---|---|---|---|---|---|---|---|---|---|---|---|---|---|---|
| Arg | Ile | Val | Gly | Pro | Lys | Thr | Cys | Arg | Asn | Thr | Trp | Ser | Gly | Thr | | |
| 1300 | | | | 1305 | | | | | 1310 | | | | | | | |

| ttc | ccc | atc | aac | gcc | tac | acc | acg | ggc | ccc | tgt | acc | ccc | ctt | cct | | 4911 |
|---|---|---|---|---|---|---|---|---|---|---|---|---|---|---|---|---|
| Phe | Pro | Ile | Asn | Ala | Tyr | Thr | Thr | Gly | Pro | Cys | Thr | Pro | Leu | Pro | | |
| 1315 | | | | 1320 | | | | | 1325 | | | | | | | |

| gcg | ccg | aac | tat | acg | ttc | gcg | ctg | tgg | agg | gtg | tct | gcg | gag | gaa | | 4956 |
|---|---|---|---|---|---|---|---|---|---|---|---|---|---|---|---|---|
| Ala | Pro | Asn | Tyr | Thr | Phe | Ala | Leu | Trp | Arg | Val | Ser | Ala | Glu | Glu | | |
| 1330 | | | | 1335 | | | | | 1340 | | | | | | | |

| tac | gtg | gaa | ata | agg | cag | gtg | ggg | gac | ttc | cac | tac | gtg | acg | ggc | | 5001 |
|---|---|---|---|---|---|---|---|---|---|---|---|---|---|---|---|---|
| Tyr | Val | Glu | Ile | Arg | Gln | Val | Gly | Asp | Phe | His | Tyr | Val | Thr | Gly | | |
| 1345 | | | | 1350 | | | | | 1355 | | | | | | | |

| atg | act | gct | gac | aac | ctt | aag | tgc | cca | tgc | cag | gtc | cca | tcg | ccc | | 5046 |
|---|---|---|---|---|---|---|---|---|---|---|---|---|---|---|---|---|
| Met | Thr | Ala | Asp | Asn | Leu | Lys | Cys | Pro | Cys | Gln | Val | Pro | Ser | Pro | | |
| 1360 | | | | 1365 | | | | | 1370 | | | | | | | |

| gaa | ttt | ttc | aca | gaa | ctg | gat | ggg | gtg | cgc | ctg | cat | agg | ttt | gcg | | 5091 |
|---|---|---|---|---|---|---|---|---|---|---|---|---|---|---|---|---|
| Glu | Phe | Phe | Thr | Glu | Leu | Asp | Gly | Val | Arg | Leu | His | Arg | Phe | Ala | | |
| 1375 | | | | 1380 | | | | | 1385 | | | | | | | |

| ccc | cct | tgc | aag | ccc | ttg | cta | cga | gat | gag | gtg | tcg | ttc | aga | gta | | 5136 |
|---|---|---|---|---|---|---|---|---|---|---|---|---|---|---|---|---|
| Pro | Pro | Cys | Lys | Pro | Leu | Leu | Arg | Asp | Glu | Val | Ser | Phe | Arg | Val | | |
| 1390 | | | | 1395 | | | | | 1400 | | | | | | | |

| gga | cta | cac | gac | tac | ccg | gtg | ggg | tcg | cag | tta | cct | tgc | gag | cct | | 5181 |
|---|---|---|---|---|---|---|---|---|---|---|---|---|---|---|---|---|
| Gly | Leu | His | Asp | Tyr | Pro | Val | Gly | Ser | Gln | Leu | Pro | Cys | Glu | Pro | | |
| 1405 | | | | 1410 | | | | | 1415 | | | | | | | |

| gaa | ccg | gat | gtg | gcc | gta | ctg | acg | tcc | atg | ctc | acc | gat | ccc | tcc | | 5226 |
|---|---|---|---|---|---|---|---|---|---|---|---|---|---|---|---|---|
| Glu | Pro | Asp | Val | Ala | Val | Leu | Thr | Ser | Met | Leu | Thr | Asp | Pro | Ser | | |
| 1420 | | | | 1425 | | | | | 1430 | | | | | | | |

| cat | ata | acg | gca | gag | gcg | gct | ggg | agg | agg | tta | gca | agg | gga | tcg | | 5271 |
|---|---|---|---|---|---|---|---|---|---|---|---|---|---|---|---|---|
| His | Ile | Thr | Ala | Glu | Ala | Ala | Gly | Arg | Arg | Leu | Ala | Arg | Gly | Ser | | |
| 1435 | | | | 1440 | | | | | 1445 | | | | | | | |

| ccc | cct | tct | ctg | gcc | agc | tcc | tcg | gcc | agc | cag | ctg | tcc | gct | cca | | 5316 |
|---|---|---|---|---|---|---|---|---|---|---|---|---|---|---|---|---|
| Pro | Pro | Ser | Leu | Ala | Ser | Ser | Ser | Ala | Ser | Gln | Leu | Ser | Ala | Pro | | |
| 1450 | | | | 1455 | | | | | 1460 | | | | | | | |

| tct | ctc | aaa | gca | act | tgc | acc | acc | aac | cac | gac | tcc | cct | gac | gcc | | 5361 |
|---|---|---|---|---|---|---|---|---|---|---|---|---|---|---|---|---|
| Ser | Leu | Lys | Ala | Thr | Cys | Thr | Thr | Asn | His | Asp | Ser | Pro | Asp | Ala | | |
| 1465 | | | | 1470 | | | | | 1475 | | | | | | | |

| gag | ctc | ata | gag | gct | aac | ctc | ctg | tgg | agg | cag | gag | atg | ggc | ggc | | 5406 |
|---|---|---|---|---|---|---|---|---|---|---|---|---|---|---|---|---|
| Glu | Leu | Ile | Glu | Ala | Asn | Leu | Leu | Trp | Arg | Gln | Glu | Met | Gly | Gly | | |
| 1480 | | | | 1485 | | | | | 1490 | | | | | | | |

| aac | atc | acc | agg | gtt | gag | tca | gag | aac | aaa | gtg | gta | gtc | ctg | gac | | 5451 |
|---|---|---|---|---|---|---|---|---|---|---|---|---|---|---|---|---|
| Asn | Ile | Thr | Arg | Val | Glu | Ser | Glu | Asn | Lys | Val | Val | Val | Leu | Asp | | |
| 1495 | | | | 1500 | | | | | 1505 | | | | | | | |

| tcc | ttc | gat | ccg | ctt | gtg | gca | gaa | gag | gac | gaa | cgg | gag | atc | tcc | | 5496 |
|---|---|---|---|---|---|---|---|---|---|---|---|---|---|---|---|---|
| Ser | Phe | Asp | Pro | Leu | Val | Ala | Glu | Glu | Asp | Glu | Arg | Glu | Ile | Ser | | |
| 1510 | | | | 1515 | | | | | 1520 | | | | | | | |

| gtg | gcc | gca | gag | atc | ctg | cgg | aag | tct | cgg | aga | ttc | gct | ccg | gcc | | 5541 |
|---|---|---|---|---|---|---|---|---|---|---|---|---|---|---|---|---|
| Val | Ala | Ala | Glu | Ile | Leu | Arg | Lys | Ser | Arg | Arg | Phe | Ala | Pro | Ala | | |
| 1525 | | | | 1530 | | | | | 1535 | | | | | | | |

| ctg | ccc | att | tgg | gca | cgg | ccg | gac | tac | aac | ccc | ccg | tta | ctg | gag | | 5586 |
|---|---|---|---|---|---|---|---|---|---|---|---|---|---|---|---|---|

```
Leu Pro Ile Trp Ala Arg Pro Asp Tyr Asn Pro Pro Leu Leu Glu
1540                1545                1550 acg tgg aaa aag ccg gac tac gag cca cct gtg gtc cat ggc tgc        5631
Thr Trp Lys Lys Pro Asp Tyr Glu Pro Pro Val Val His Gly Cys
1555                1560                1565 ccg ctt cca cct cca aag tcc cct cct gtg cct ccg ccc cgg aag        5676
Pro Leu Pro Pro Pro Lys Ser Pro Pro Val Pro Pro Pro Arg Lys
1570                1575                1580 aag cgg acg gtg gtc ctc act gaa tca act gta tcc act gcc ttg        5721
Lys Arg Thr Val Val Leu Thr Glu Ser Thr Val Ser Thr Ala Leu
1585                1590                1595 gct gag ctt gct acc aag agc ttt ggc agc tct tca act tcc ggt        5766
Ala Glu Leu Ala Thr Lys Ser Phe Gly Ser Ser Ser Thr Ser Gly
1600                1605                1610 ata acg ggc gac aac acg aca gcg tcc tct gag ccc gcc ccc tct        5811
Ile Thr Gly Asp Asn Thr Thr Ala Ser Ser Glu Pro Ala Pro Ser
1615                1620                1625 gtc tgc cct cca gac tcc gac gct gag tcc tat tct tcc atg ccc        5856
Val Cys Pro Pro Asp Ser Asp Ala Glu Ser Tyr Ser Ser Met Pro
1630                1635                1640 ccc ctg gag ggg gag cct ggg gat ccg gat ctc agc gac ggg tca        5901
Pro Leu Glu Gly Glu Pro Gly Asp Pro Asp Leu Ser Asp Gly Ser
1645                1650                1655 tgg tcg acg gtc agt agt ggg gct ggc acg gag gat gtc gtg tgt        5946
Trp Ser Thr Val Ser Ser Gly Ala Gly Thr Glu Asp Val Val Cys
1660                1665                1670 tgc tca atg tcc tat tcc tgg aca ggc gca ctc atc acc ccg tgt        5991
Cys Ser Met Ser Tyr Ser Trp Thr Gly Ala Leu Ile Thr Pro Cys
1675                1680                1685 gcc gcg gaa gaa caa aaa ttg cct atc aac gca ctg agc aac tca        6036
Ala Ala Glu Glu Gln Lys Leu Pro Ile Asn Ala Leu Ser Asn Ser
1690                1695                1700 tta ctg cgt cac cac aac ctc gtg tat tcc acc acc tca cgc agt        6081
Leu Leu Arg His His Asn Leu Val Tyr Ser Thr Thr Ser Arg Ser
1705                1710                1715 gct tgc caa agg cag aag aaa gtc aca ttt gac aga ctg caa gtt        6126
Ala Cys Gln Arg Gln Lys Lys Val Thr Phe Asp Arg Leu Gln Val
1720                1725                1730 ctg gac aac cac tac cag gac gtg ctc aag gag gtt aag gcg gcg        6171
Leu Asp Asn His Tyr Gln Asp Val Leu Lys Glu Val Lys Ala Ala
1735                1740                1745 gcg tca aaa gtg aag gct aac ttg cta tcc gta gag gaa gct tgc        6216
Ala Ser Lys Val Lys Ala Asn Leu Leu Ser Val Glu Glu Ala Cys
1750                1755                1760 agc ctg acg ccc cca cat tca gcc aga tca aaa ttt ggc tat ggg        6261
Ser Leu Thr Pro Pro His Ser Ala Arg Ser Lys Phe Gly Tyr Gly
1765                1770                1775 gca aaa gac gtc cgt tgc cat gcc aga aag gcc gta aac cac atc        6306
Ala Lys Asp Val Arg Cys His Ala Arg Lys Ala Val Asn His Ile
1780                1785                1790 aac tcc gtg tgg aaa gac ctt ctg gaa gac agt gtt aca cca ata        6351
Asn Ser Val Trp Lys Asp Leu Leu Glu Asp Ser Val Thr Pro Ile
1795                1800                1805 gac aca acc atc atg gct aag aac gaa gtt ttc tgc gtt cag cct        6396
Asp Thr Thr Ile Met Ala Lys Asn Glu Val Phe Cys Val Gln Pro
1810                1815                1820 gag aag ggg ggt cgt aag cca gct cgt ctc atc gtg tac cct gac        6441
Glu Lys Gly Gly Arg Lys Pro Ala Arg Leu Ile Val Tyr Pro Asp
1825                1830                1835 ctg ggt gtg cgc gtg tgc gag aaa atg gcc ctg tac gac gtg gta        6486
```

```
Leu Gly Val Arg Val Cys Glu Lys Met Ala Leu Tyr Asp Val Val
1840                1845                1850 aaa aaa ctc ccc ctg gcc gtg atg gga agc tcc tac gga ttc cag         6531
Lys Lys Leu Pro Leu Ala Val Met Gly Ser Ser Tyr Gly Phe Gln
1855                1860                1865 tac tca cca gga cag cgg gtt gaa ttc ctc gtg caa gcg tgg aag         6576
Tyr Ser Pro Gly Gln Arg Val Glu Phe Leu Val Gln Ala Trp Lys
1870                1875                1880 tcc aag ggg acc cca atg ggg ttc tcg tat gat acc cgc tgc ttt         6621
Ser Lys Gly Thr Pro Met Gly Phe Ser Tyr Asp Thr Arg Cys Phe
1885                1890                1895 gac tct aca gtc act gag agc gat atc cgt acg gag gag gca atc         6666
Asp Ser Thr Val Thr Glu Ser Asp Ile Arg Thr Glu Glu Ala Ile
1900                1905                1910 tac cag tgt tgt gac ctg gac ccc caa gcc cgc gtg gcc atc aag         6711
Tyr Gln Cys Cys Asp Leu Asp Pro Gln Ala Arg Val Ala Ile Lys
1915                1920                1925 tcc ctc acc gag agg ctt tat gtc ggg ggt cct ctt acc aat tca         6756
Ser Leu Thr Glu Arg Leu Tyr Val Gly Gly Pro Leu Thr Asn Ser
1930                1935                1940 agg ggg gaa aac tgc ggc tat cgc agg tgc cgc gca agc ggc gta         6801
Arg Gly Glu Asn Cys Gly Tyr Arg Arg Cys Arg Ala Ser Gly Val
1945                1950                1955 ctg aca act agc tgt ggt aac acc ctc act tgc tac atc aag gcc         6846
Leu Thr Thr Ser Cys Gly Asn Thr Leu Thr Cys Tyr Ile Lys Ala
1960                1965                1970 cga gca gcc tgt cga gcc gca ggg ctc cgg gac tgc acc atg ctc         6891
Arg Ala Ala Cys Arg Ala Ala Gly Leu Arg Asp Cys Thr Met Leu
1975                1980                1985 gtg tgt ggc gac gac tta gtc gtt atc tgt gaa agc cag ggg gtc         6936
Val Cys Gly Asp Asp Leu Val Val Ile Cys Glu Ser Gln Gly Val
1990                1995                2000 caa gag gat aca gcg agc ctg aga gcc ttc acg gag gct atg acc         6981
Gln Glu Asp Thr Ala Ser Leu Arg Ala Phe Thr Glu Ala Met Thr
2005                2010                2015 agg tac tcc gct ccc ccc ggg gac ccc ccc caa cca gaa tac gac         7026
Arg Tyr Ser Ala Pro Pro Gly Asp Pro Pro Gln Pro Glu Tyr Asp
2020                2025                2030 ttg gag ctc ata aca tcg tgc tcc tct aac gtg tca gtc gcc cac         7071
Leu Glu Leu Ile Thr Ser Cys Ser Ser Asn Val Ser Val Ala His
2035                2040                2045 gac gac act gga aag agg gtc tat tac ctt acc cgt gac cct aca         7116
Asp Asp Thr Gly Lys Arg Val Tyr Tyr Leu Thr Arg Asp Pro Thr
2050                2055                2060 act ccc ctc gcg aga gcc gcg tgg gag aca gca aga cac act cca         7161
Thr Pro Leu Ala Arg Ala Ala Trp Glu Thr Ala Arg His Thr Pro
2065                2070                2075 gtc aat tcc tgg cta ggc aac ata atc atg ttt gcc ccc aca ttg         7206
Val Asn Ser Trp Leu Gly Asn Ile Ile Met Phe Ala Pro Thr Leu
2080                2085                2090 tgg gtg aga atg ata ctg ctg ccc cac ttc ttc agt gtc ctc atg         7251
Trp Val Arg Met Ile Leu Leu Pro His Phe Phe Ser Val Leu Met
2095                2100                2105 gcc agg gac caa ctt gaa cag gcc ctt gat tgc gaa atc tac gga         7296
Ala Arg Asp Gln Leu Glu Gln Ala Leu Asp Cys Glu Ile Tyr Gly
2110                2115                2120 gcc tgc tac tcc ata gaa cca ctg gac cta cct cca atc att caa         7341
Ala Cys Tyr Ser Ile Glu Pro Leu Asp Leu Pro Pro Ile Ile Gln
2125                2130                2135 aga ctc cat ggc ctt agc gca ttt tca ctc cac agt tac tct cca         7386
```

```
Arg Leu His Gly Leu Ser Ala Phe Ser Leu His Ser Tyr Ser Pro
2140                2145                2150 ggt gaa atc aat agg gtg gcc gca tgc ctc aga aaa ctt ggg gtc      7431
Gly Glu Ile Asn Arg Val Ala Ala Cys Leu Arg Lys Leu Gly Val
2155                2160                2165 ccg ccc ttg cga gct tgg aga cac cgg gcc cgg agc atc cgc gct      7476
Pro Pro Leu Arg Ala Trp Arg His Arg Ala Arg Ser Ile Arg Ala
2170                2175                2180 aag ctt ctg tcc aga gga ggc agg gct gcc acg tgt ggc aag tac      7521
Lys Leu Leu Ser Arg Gly Gly Arg Ala Ala Thr Cys Gly Lys Tyr
2185                2190                2195 ctc ttc aat tgg gca gta aga aca aag ctc aaa ctc act cca ata      7566
Leu Phe Asn Trp Ala Val Arg Thr Lys Leu Lys Leu Thr Pro Ile
2200                2205                2210 gcg gcc gct agc cag ctg gac ttg tcc ggt tgg ttc acg gct ggc      7611
Ala Ala Ala Ser Gln Leu Asp Leu Ser Gly Trp Phe Thr Ala Gly
2215                2220                2225 tac agc ggg gga gac att tat cac agc gtg tct cgt gcc cgg ccc      7656
Tyr Ser Gly Gly Asp Ile Tyr His Ser Val Ser Arg Ala Arg Pro
2230                2235                2240 cgc tgg ttc tgg ttt tgc cta ctc ctg ctt gct gca ggg gta ggc      7701
Arg Trp Phe Trp Phe Cys Leu Leu Leu Ala Ala Gly Val Gly
2245                2250                2255 atc tac ctc ctc ccc aac cga tgaaggttgg ggtaaacact ccggcctctt    7752
Ile Tyr Leu Leu Pro Asn Arg
2260                2265 aggccattcc tgttttttt tttttttct tttgtttttt ttgtttttt ttttttttt    7812 cctttctttt tttttttt tcctttcttc tttaatggtg gctccatctt agccctagtc  7872
acggctagct gtgaaaggtc cgtgagccgc atgactgcag agagctga tactggcctc  7932 tctgcagatc atgt                                                   7946

<210> SEQ ID NO 4
<211> LENGTH: 280
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Met Ser Thr Asn Pro Lys Pro Gln Arg Lys Thr Lys Arg Asn Thr Asn
1               5                   10                  15

Met Ile Glu Gln Asp Gly Leu His Ala Gly Ser Pro Ala Ala Trp Val
            20                  25                  30

Glu Arg Leu Phe Gly Tyr Asp Trp Ala Gln Gln Thr Ile Gly Cys Ser
        35                  40                  45

Asp Ala Ala Val Phe Arg Leu Ser Ala Gln Gly Arg Pro Val Leu Phe
    50                  55                  60

Val Lys Thr Asp Leu Ser Gly Ala Leu Asn Glu Leu Gln Asp Glu Ala
65                  70                  75                  80

Ala Arg Leu Ser Trp Leu Ala Thr Thr Gly Val Pro Cys Ala Ala Val
                85                  90                  95

Leu Asp Val Val Thr Glu Ala Gly Arg Asp Trp Leu Leu Leu Gly Glu
            100                 105                 110

Val Pro Gly Gln Asp Leu Leu Ser Ser His Leu Ala Pro Ala Glu Lys
        115                 120                 125

Val Ser Ile Met Ala Asp Ala Met Arg Arg Leu His Thr Leu Asp Pro
    130                 135                 140
```

```
Ala Thr Cys Pro Phe Asp His Gln Ala Lys His Arg Ile Glu Arg Ala
145                 150                 155                 160

Arg Thr Arg Met Glu Ala Gly Leu Val Asp Gln Asp Leu Asp Glu
                165                 170                 175

Glu His Gln Gly Leu Ala Pro Ala Glu Leu Phe Ala Arg Leu Lys Ala
            180                 185                 190

Arg Met Pro Asp Gly Glu Asp Leu Val Val Thr His Gly Asp Ala Cys
        195                 200                 205

Leu Pro Asn Ile Met Val Glu Asn Gly Arg Phe Ser Gly Phe Ile Asp
    210                 215                 220

Cys Gly Arg Leu Gly Val Ala Asp Arg Tyr Gln Asp Ile Ala Leu Ala
225                 230                 235                 240

Thr Arg Asp Ile Ala Glu Glu Leu Gly Gly Trp Ala Asp Arg Phe
                245                 250                 255

Leu Val Leu Tyr Gly Ile Ala Ala Pro Asp Ser Gln Arg Ile Ala Phe
            260                 265                 270

Tyr Arg Leu Leu Asp Glu Phe Phe
        275                 280

<210> SEQ ID NO 5
<211> LENGTH: 1986
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Thr Asp Asn Ser Ser Pro Pro
            180                 185                 190

Ala Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220
```

-continued

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
            245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Val Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Met Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
                405                 410                 415

Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Ile Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val

-continued

```
                    645                 650                 655
    Ile Val Gly Arg Ile Val Leu Ser Gly Lys Pro Ala Ile Ile Pro Asp
                660                 665                 670
    Arg Glu Val Leu Tyr Arg Glu Phe Asp Glu Met Glu Glu Cys Ser Gln
                675                 680                 685
    His Leu Pro Tyr Ile Glu Gln Gly Met Met Leu Ala Glu Gln Phe Lys
                690                 695                 700
    Gln Lys Ala Leu Gly Leu Gln Thr Ala Ser Arg Gln Ala Glu Val
    705                 710                 715                 720
    Ile Ala Pro Thr Val Gln Thr Asn Trp Gln Arg Leu Glu Ala Phe Trp
                    725                 730                 735
    Ala Lys His Met Trp Asn Phe Ile Ser Gly Ile Gln Tyr Leu Ala Gly
                740                 745                 750
    Leu Ser Thr Leu Pro Gly Asn Pro Ala Ile Ala Ser Leu Met Ala Phe
                755                 760                 765
    Thr Ala Ala Val Thr Ser Pro Leu Thr Thr Gly Gln Thr Leu Leu Phe
                770                 775                 780
    Asn Ile Leu Gly Gly Trp Val Ala Ala Gln Leu Ala Ala Pro Gly Ala
    785                 790                 795                 800
    Ala Thr Ala Phe Val Gly Ala Gly Leu Ala Gly Ala Ala Ile Gly Ser
                    805                 810                 815
    Val Gly Leu Gly Lys Val Leu Val Asp Ile Leu Ala Gly Tyr Gly Ala
                820                 825                 830
    Gly Val Ala Gly Ala Leu Val Ala Phe Lys Ile Met Ser Gly Glu Val
                835                 840                 845
    Pro Ser Thr Glu Asp Leu Val Asn Leu Leu Pro Ala Ile Leu Ser Pro
                850                 855                 860
    Gly Ala Leu Val Val Gly Val Val Cys Ala Ala Ile Leu Arg Arg His
    865                 870                 875                 880
    Val Gly Pro Gly Glu Gly Ala Val Gln Trp Met Asn Arg Leu Ile Ala
                    885                 890                 895
    Phe Ala Ser Arg Gly Asn His Val Ser Pro Thr His Tyr Val Pro Glu
                900                 905                 910
    Ser Asp Ala Ala Ala Arg Val Thr Ala Ile Leu Ser Ser Leu Thr Val
                915                 920                 925
    Thr Gln Leu Leu Arg Arg Leu His Gln Trp Leu Ser Ser Glu Cys Thr
                930                 935                 940
    Thr Pro Cys Ser Gly Ser Trp Leu Arg Asp Ile Trp Asp Trp Ile Cys
    945                 950                 955                 960
    Glu Val Leu Ser Asp Phe Lys Thr Trp Leu Lys Ala Lys Leu Met Pro
                    965                 970                 975
    Gln Leu Pro Gly Ile Pro Phe Val Ser Cys Gln Arg Gly Tyr Arg Gly
                980                 985                 990
    Val Trp Arg Gly Asp Gly Ile Met His Thr Arg Cys Pro Cys Gly Ala
                995                 1000                1005
    Glu Ile Ala Gly His Val Lys Asn Gly Thr Met Arg Ile Val Gly
                1010                1015                1020
    Pro Lys Thr Cys Arg Asn Thr Trp Ser Gly Thr Phe Pro Ile Asn
                1025                1030                1035
    Ala Tyr Thr Thr Gly Pro Cys Thr Pro Leu Pro Ala Pro Asn Tyr
                1040                1045                1050
    Thr Phe Ala Leu Trp Arg Val Ser Ala Glu Glu Tyr Val Glu Ile
                1055                1060                1065
```

-continued

Arg Gln Val Gly Asp Phe His Tyr Val Thr Gly Met Thr Ala Asp
1070                    1075                1080

Asn Leu Lys Cys Pro Cys Gln Val Pro Ser Pro Glu Phe Phe Thr
1085                    1090                1095

Glu Leu Asp Gly Val Arg Leu His Arg Phe Ala Pro Pro Cys Lys
1100                    1105                1110

Pro Leu Leu Arg Asp Glu Val Ser Phe Arg Val Gly Leu His Asp
1115                    1120                1125

Tyr Pro Val Gly Ser Gln Leu Pro Cys Glu Pro Glu Pro Asp Val
1130                    1135                1140

Ala Val Leu Thr Ser Met Leu Thr Asp Pro Ser His Ile Thr Ala
1145                    1150                1155

Glu Ala Ala Gly Arg Arg Leu Ala Arg Gly Ser Pro Pro Ser Leu
1160                    1165                1170

Ala Ser Ser Ser Ala Ser Gln Leu Ser Ala Pro Ser Leu Lys Ala
1175                    1180                1185

Thr Cys Thr Thr Asn His Asp Ser Pro Asp Ala Glu Leu Ile Glu
1190                    1195                1200

Ala Asn Leu Leu Trp Arg Gln Glu Met Gly Gly Asn Ile Thr Arg
1205                    1210                1215

Val Glu Ser Glu Asn Lys Val Val Leu Asp Ser Phe Asp Pro
1220                    1225                1230

Leu Val Ala Glu Glu Asp Glu Arg Glu Ile Ser Val Ala Ala Glu
1235                    1240                1245

Ile Leu Arg Lys Ser Arg Arg Phe Ala Pro Ala Leu Pro Ile Trp
1250                    1255                1260

Ala Arg Pro Asp Tyr Asn Pro Pro Leu Leu Glu Thr Trp Lys Lys
1265                    1270                1275

Pro Asp Tyr Glu Pro Pro Val Val His Gly Cys Pro Leu Pro Pro
1280                    1285                1290

Pro Lys Ser Pro Pro Val Pro Pro Arg Lys Lys Arg Thr Val
1295                    1300                1305

Val Leu Thr Glu Ser Thr Val Ser Thr Ala Leu Ala Glu Leu Ala
1310                    1315                1320

Thr Lys Ser Phe Gly Ser Ser Ser Thr Ser Gly Ile Thr Gly Asp
1325                    1330                1335

Asn Thr Thr Ala Ser Ser Glu Pro Ala Pro Ser Val Cys Pro Pro
1340                    1345                1350

Asp Ser Asp Ala Glu Ser Tyr Ser Ser Met Pro Pro Leu Glu Gly
1355                    1360                1365

Glu Pro Gly Asp Pro Asp Leu Ser Asp Gly Ser Trp Ser Thr Val
1370                    1375                1380

Ser Ser Gly Ala Gly Thr Glu Asp Val Val Cys Cys Ser Met Ser
1385                    1390                1395

Tyr Ser Trp Thr Gly Ala Leu Ile Thr Pro Cys Ala Ala Glu Glu
1400                    1405                1410

Gln Lys Leu Pro Ile Asn Ala Leu Ser Asn Ser Leu Leu Arg His
1415                    1420                1425

His Asn Leu Val Tyr Ser Thr Thr Ser Arg Ser Ala Cys Gln Arg
1430                    1435                1440

Gln Lys Lys Val Thr Phe Asp Arg Leu Gln Val Leu Asp Asn His
1445                    1450                1455

Tyr Gln Asp Val Leu Lys Glu Val Lys Ala Ala Ala Ser Lys Val
1460                    1465                1470

```
Lys Ala Asn Leu Leu Ser Val Glu Glu Ala Cys Ser Leu Thr Pro
    1475                1480                1485

Pro His Ser Ala Arg Ser Lys Phe Gly Tyr Gly Ala Lys Asp Val
    1490                1495                1500

Arg Cys His Ala Arg Lys Ala Val Asn His Ile Asn Ser Val Trp
    1505                1510                1515

Lys Asp Leu Leu Glu Asp Ser Val Thr Pro Ile Asp Thr Thr Ile
    1520                1525                1530

Met Ala Lys Asn Glu Val Phe Cys Val Gln Pro Glu Lys Gly Gly
    1535                1540                1545

Arg Lys Pro Ala Arg Leu Ile Val Tyr Pro Asp Leu Gly Val Arg
    1550                1555                1560

Val Cys Glu Lys Met Ala Leu Tyr Asp Val Val Lys Lys Leu Pro
    1565                1570                1575

Leu Ala Val Met Gly Ser Ser Tyr Gly Phe Gln Tyr Ser Pro Gly
    1580                1585                1590

Gln Arg Val Glu Phe Leu Val Gln Ala Trp Lys Ser Lys Gly Thr
    1595                1600                1605

Pro Met Gly Phe Ser Tyr Asp Thr Arg Cys Phe Asp Ser Thr Val
    1610                1615                1620

Thr Glu Ser Asp Ile Arg Thr Glu Glu Ala Ile Tyr Gln Cys Cys
    1625                1630                1635

Asp Leu Asp Pro Gln Ala Arg Val Ala Ile Lys Ser Leu Thr Glu
    1640                1645                1650

Arg Leu Tyr Val Gly Gly Pro Leu Thr Asn Ser Arg Gly Glu Asn
    1655                1660                1665

Cys Gly Tyr Arg Arg Cys Arg Ala Ser Gly Val Leu Thr Thr Ser
    1670                1675                1680

Cys Gly Asn Thr Leu Thr Cys Tyr Ile Lys Ala Arg Ala Ala Cys
    1685                1690                1695

Arg Ala Ala Gly Leu Arg Asp Cys Thr Met Leu Val Cys Gly Asp
    1700                1705                1710

Asp Leu Val Val Ile Cys Glu Ser Gln Gly Val Gln Glu Asp Thr
    1715                1720                1725

Ala Ser Leu Arg Ala Phe Thr Glu Ala Met Thr Arg Tyr Ser Ala
    1730                1735                1740

Pro Pro Gly Asp Pro Pro Gln Pro Glu Tyr Asp Leu Glu Leu Ile
    1745                1750                1755

Thr Ser Cys Ser Ser Asn Val Ser Val Ala His Asp Asp Thr Gly
    1760                1765                1770

Lys Arg Val Tyr Tyr Leu Thr Arg Asp Pro Thr Thr Pro Leu Ala
    1775                1780                1785

Arg Ala Ala Trp Glu Thr Ala Arg His Thr Pro Val Asn Ser Trp
    1790                1795                1800

Leu Gly Asn Ile Ile Met Phe Ala Pro Thr Leu Trp Val Arg Met
    1805                1810                1815

Ile Leu Leu Pro His Phe Phe Ser Val Leu Met Ala Arg Asp Gln
    1820                1825                1830

Leu Glu Gln Ala Leu Asp Cys Glu Ile Tyr Gly Ala Cys Tyr Ser
    1835                1840                1845

Ile Glu Pro Leu Asp Leu Pro Pro Ile Ile Gln Arg Leu His Gly
    1850                1855                1860

Leu Ser Ala Phe Ser Leu His Ser Tyr Ser Pro Gly Glu Ile Asn
```

```
                    1865                1870                1875

Arg Val Ala Ala Cys Leu Arg Lys Leu Gly Val Pro Pro Leu Arg
    1880            1885                1890

Ala Trp Arg His Arg Ala Arg Ser Ile Arg Ala Lys Leu Leu Ser
    1895            1900                1905

Arg Gly Gly Arg Ala Ala Thr Cys Gly Lys Tyr Leu Phe Asn Trp
    1910            1915                1920

Ala Val Arg Thr Lys Leu Lys Leu Thr Pro Ile Ala Ala Ala Ser
    1925            1930                1935

Gln Leu Asp Leu Ser Gly Trp Phe Thr Ala Gly Tyr Ser Gly Gly
    1940            1945                1950

Asp Ile Tyr His Ser Val Ser Arg Ala Arg Pro Arg Trp Phe Trp
    1955            1960                1965

Phe Cys Leu Leu Leu Leu Ala Ala Gly Val Gly Ile Tyr Leu Leu
    1970            1975                1980

Pro Asn Arg
    1985

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgggagagcc atagtgg                                                      17

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agtaccacaa ggcctttcg                                                    19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
ctgcggaacc ggtgagtaca c                                                 21
```